United States Patent [19]

Monteleone et al.

[11] Patent Number: 5,610,133

[45] Date of Patent: Mar. 11, 1997

[54] ALKYL-SUBSTITUTED-$C_1$-$C_3$ ALKOXY-$C_6$-CYCLOALIPHATIC COMPOUNDS, ORGANOLEPTIC USES THEREOF AND PROCESSES FOR PREPARING SAME

[75] Inventors: Michael G. Monteleone, Hazlet; Richard A. Weiss, Pine Brook; Marc D. Evans, South Orange; Marie R. Hanna, Keyport, all of N.J.

[73] Assignee: International Flavors & Fragrances Inc., New York, N.Y.

[21] Appl. No.: 647,330

[22] Filed: May 9, 1996

Related U.S. Application Data

[63] Continuation-in-part of Ser. No. 522,122, Aug. 12, 1995, Pat. No. 5,543,398.

[51] Int. Cl.$^6$ .................................................. A61K 7/46
[52] U.S. Cl. ........................... 512/20; 512/23; 568/579; 568/658
[58] Field of Search .................... 568/658, 579; 512/20, 23

[56] References Cited

U.S. PATENT DOCUMENTS

| | | | |
|---|---|---|---|
| 5,403,805 | 4/1995 | Gubitosa et al. | 502/185 |
| 5,426,216 | 6/1995 | Genet et al. | 562/450 |
| 5,462,923 | 10/1995 | Monteleone et al. | 512/19 |

FOREIGN PATENT DOCUMENTS

| | | | |
|---|---|---|---|
| 544110A1 | 6/1993 | European Pat. Off. | C07C 35/08 |
| 0616994 | 9/1994 | European Pat. Off. | C07C 41/28 |

OTHER PUBLICATIONS

Eliel and Krishnamurthy, *Chemical Abstracts*, vol. 63, 1965, 3011g (abstract of J. Org. Chem. 30(3), pp. 848–854, 1965).

Faillebin, *Beilstein* E II 6; H7,3 (abstract of Ann. chim. 4, 156–82, 410–96 (1925).

Kameoka, et a, *Chemical Abstract*, vol. 108, 1988, No. 108:62302g (abstract of Kameoka, et al, Nippon Nogei Kagaku Kaishi 1987, 61(9), 1119–21 (Japan).

BASF AG, abstract of published and examined Japanese Application No. JP 95/051523-B2, published in the *Derwent Chemical Patents Index Alerting Abstracts Bulletin*, Section "E General Chemicals", week 9527, 1990.

Becker, et al, *Perfumer & Flavorist*, vol. 15, Nov./Dec. 1990, entitled: "The Relation of Structure and Odor in Substituted Cyclohexanols" (article at pp. 29–33 and front cover).

*Primary Examiner*—James H. Reamer
*Attorney, Agent, or Firm*—Arthur L. Liberman

[57] ABSTRACT

Described are compounds defined according to the structure:

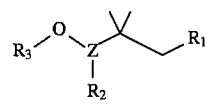

wherein Z represents meta or para cyclohexylene or meta or para phenylene and wherein $R_1$ and $R_2$ are the same or different methyl or hydrogen; and wherein $R_3$ represents $C_1$–$C_3$ alkyl; and wherein the moiety:

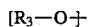

is ortho with respect to $R_2$ and para or meta with respect to the moiety:

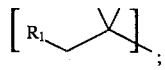

with the proviso that the sum of the number of carbon atoms in $R_1$, $R_2$ and $R_3$ is 3 or 4; and uses thereof in augmenting or enhancing the aroma of perfume compositions, colognes and perfumed articles including but not limited to solid or liquid anionic, cationic, nonionic or zwitterionic detergents, fabric softener compositions, fabric softener articles and hair preparations; as well as processes for preparing alkyl-substituted-$C_1$–$C_3$ alkoxy-$C_6$-cycloaliphatic compounds.

18 Claims, 54 Drawing Sheets

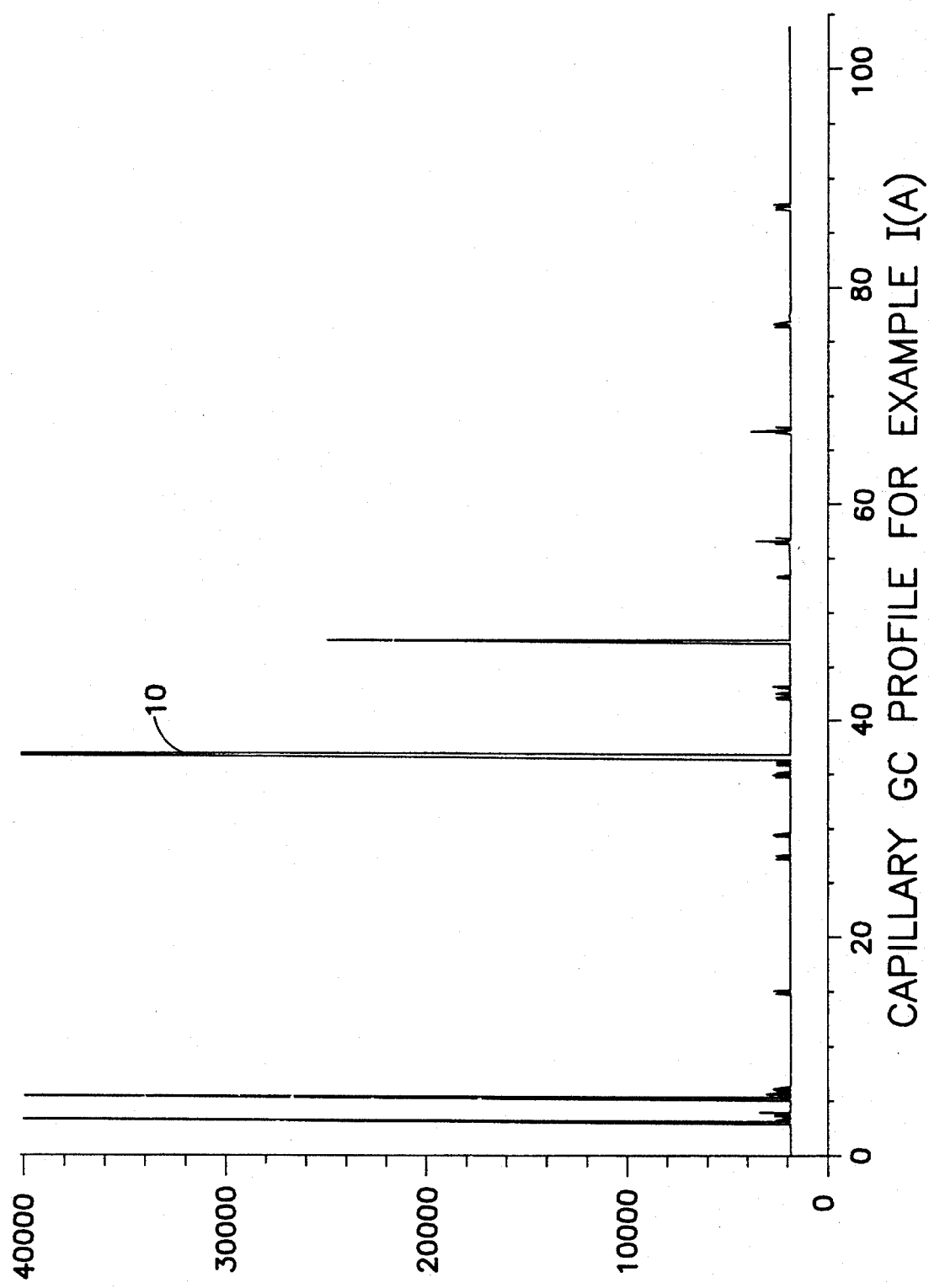

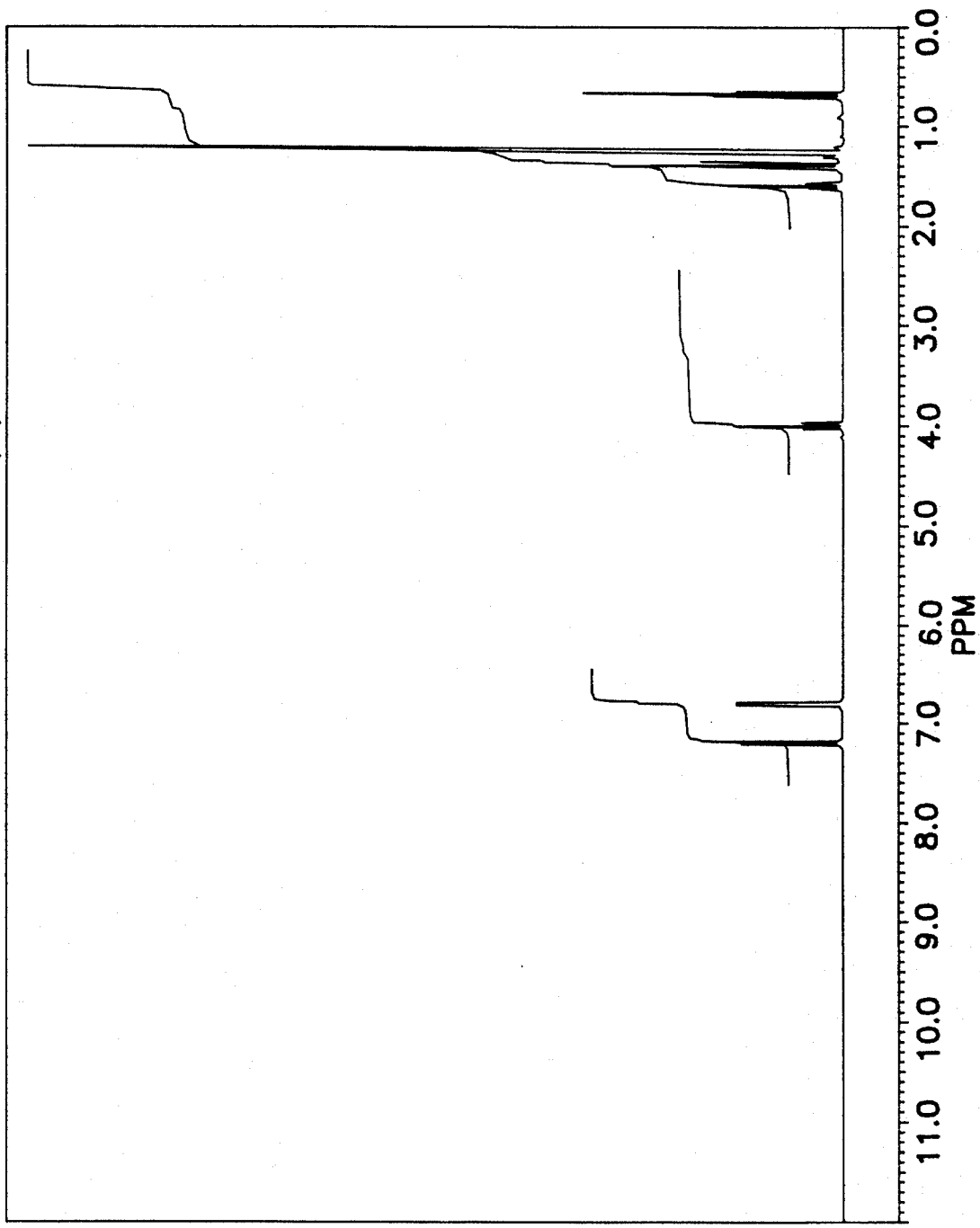

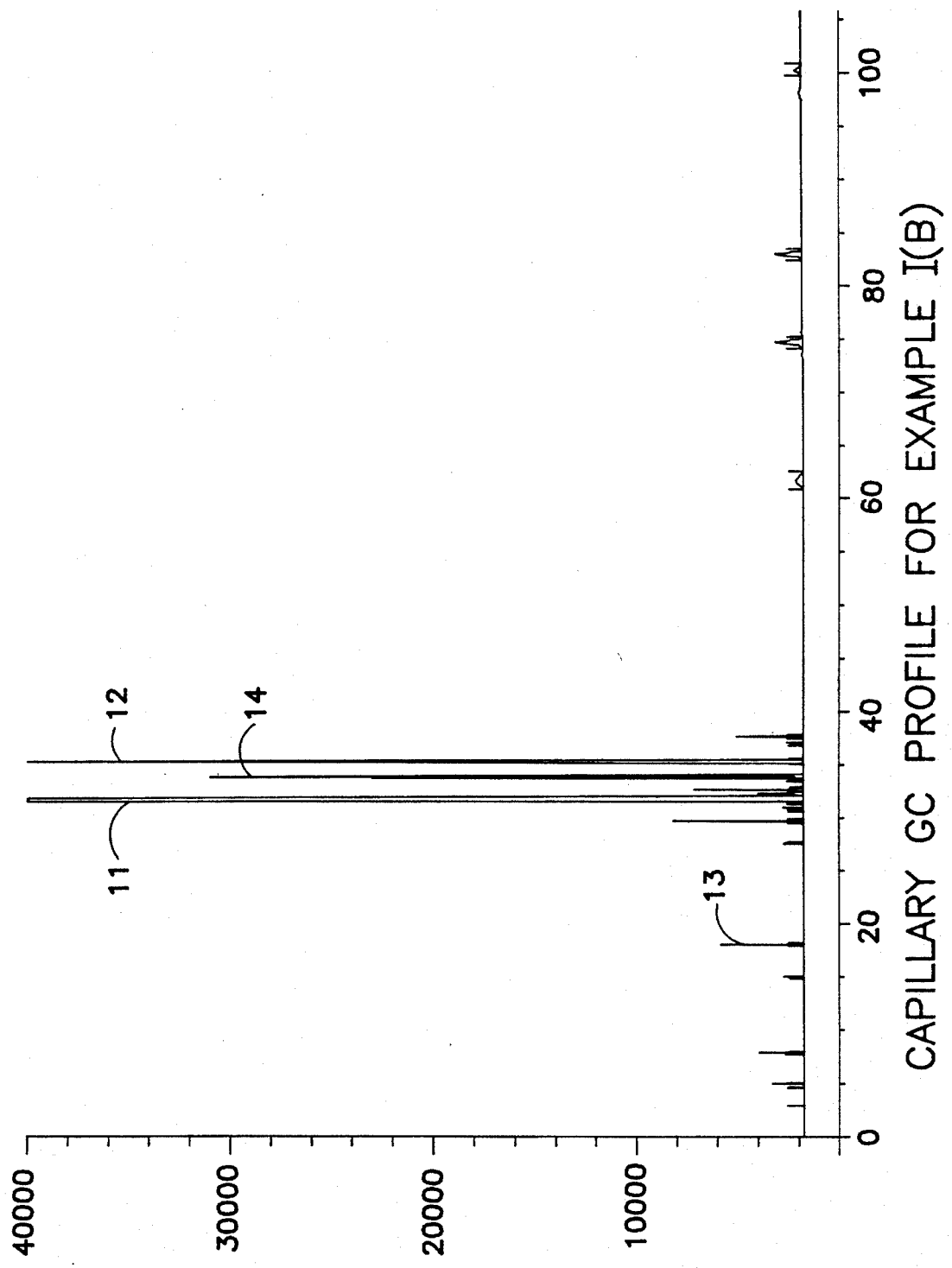

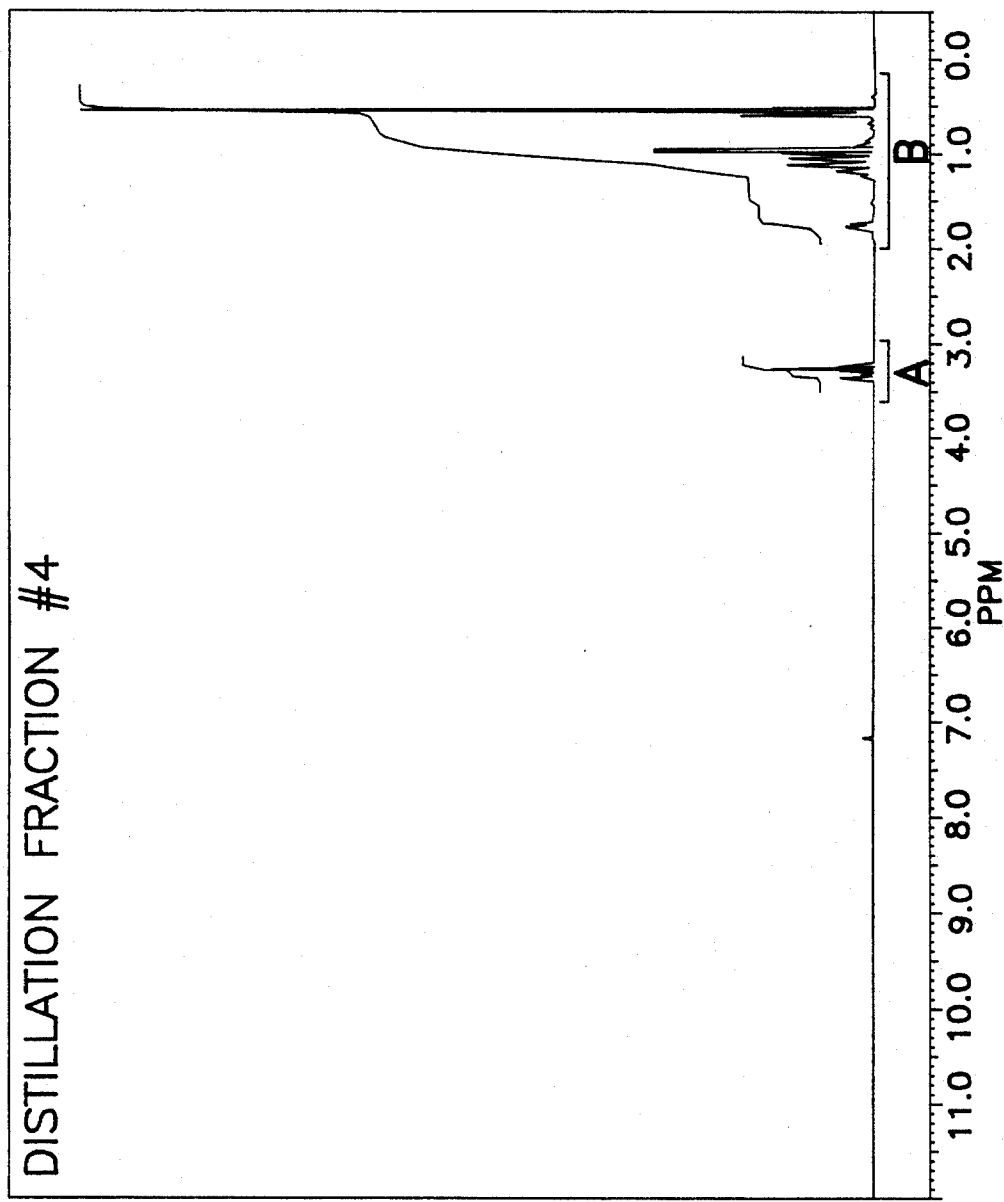

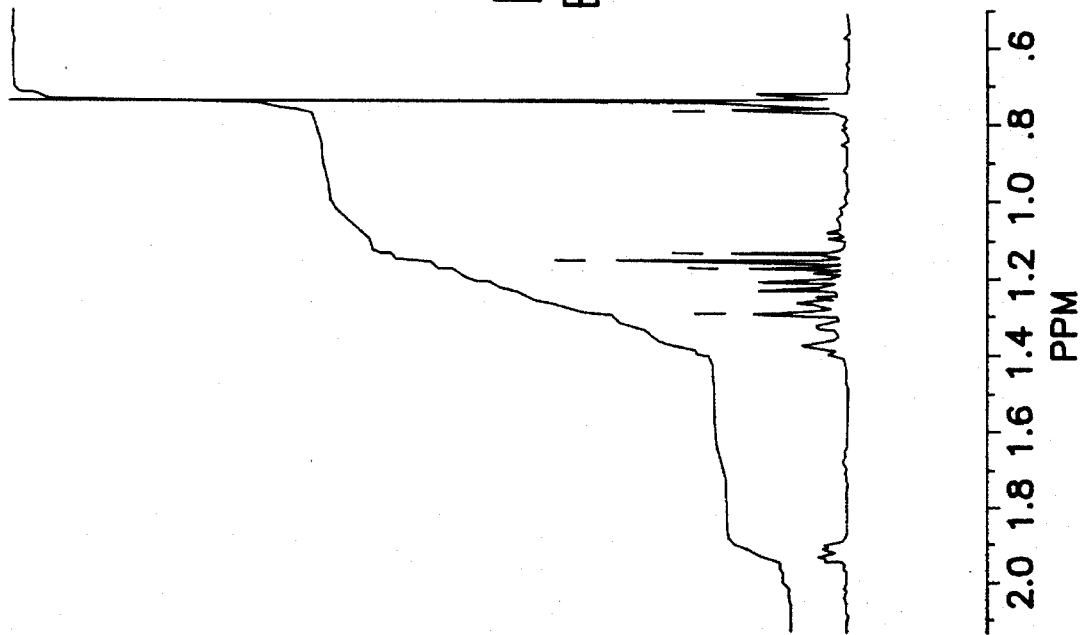
FIG.4(B) EXAMPLE I(B)
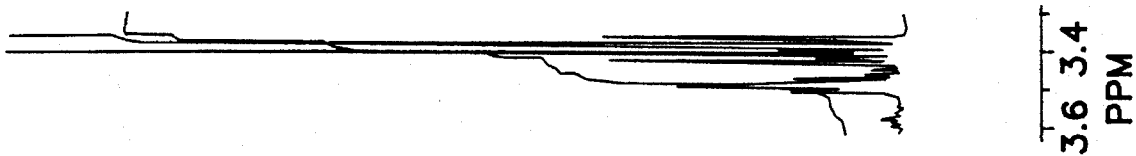
FIG.4(A) EXAMPLE I(B)

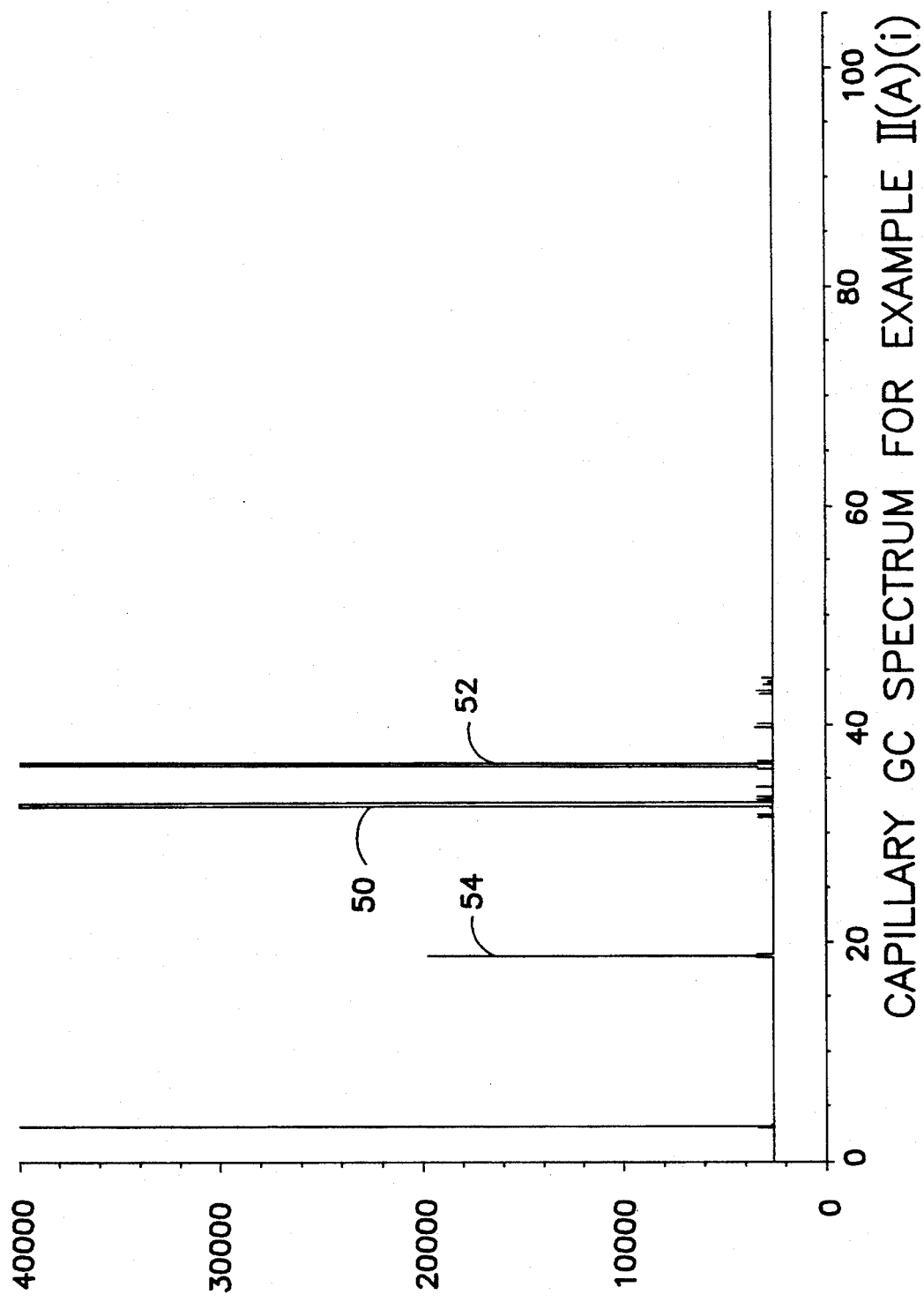

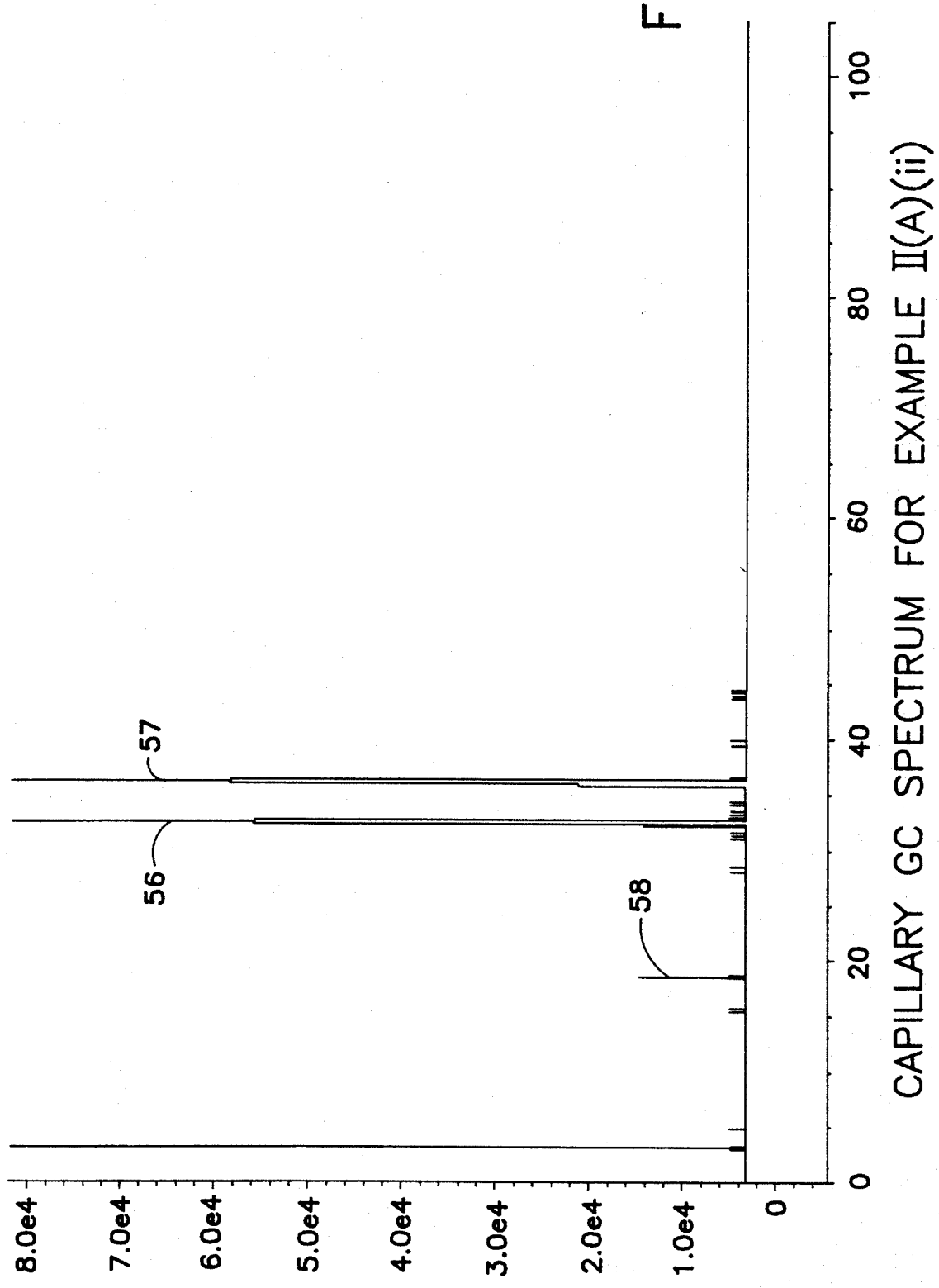

GLC PROFILE FOR EXAMPLE II(A)(iii)

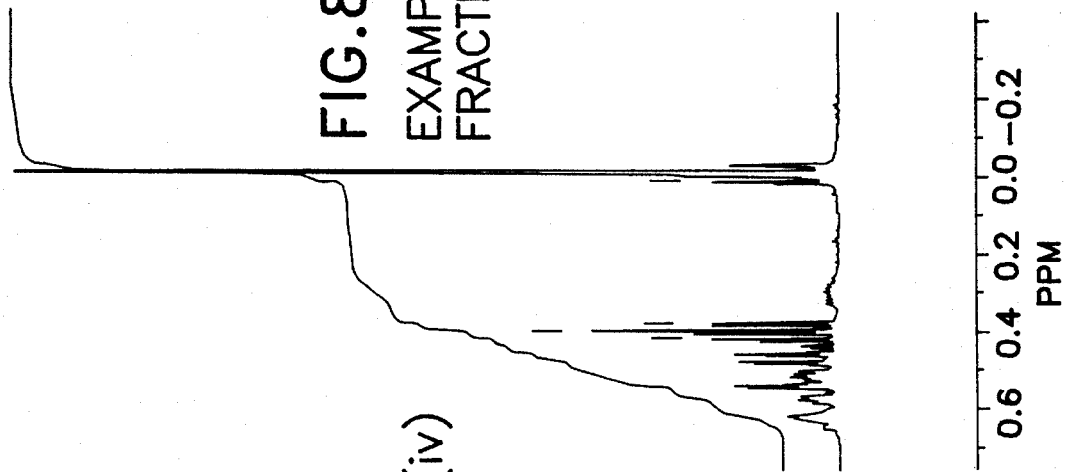
FIG.8(A) EXAMPLE II(A)(iv) FRACTION #9
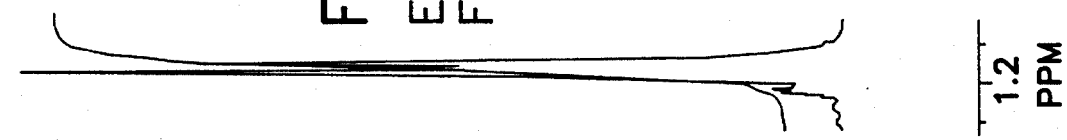
FIG.8(B) EXAMPLE II(A)(iv) FRACTION #9
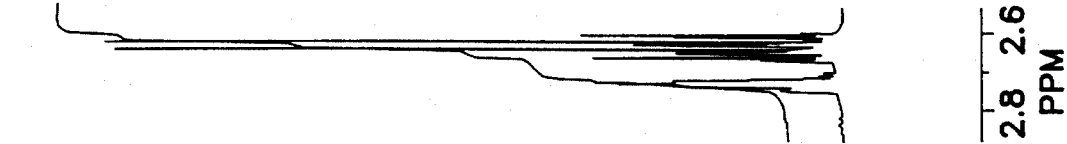
FIG.8(C) EXAMPLE II(A)(iv) FRACTION #9

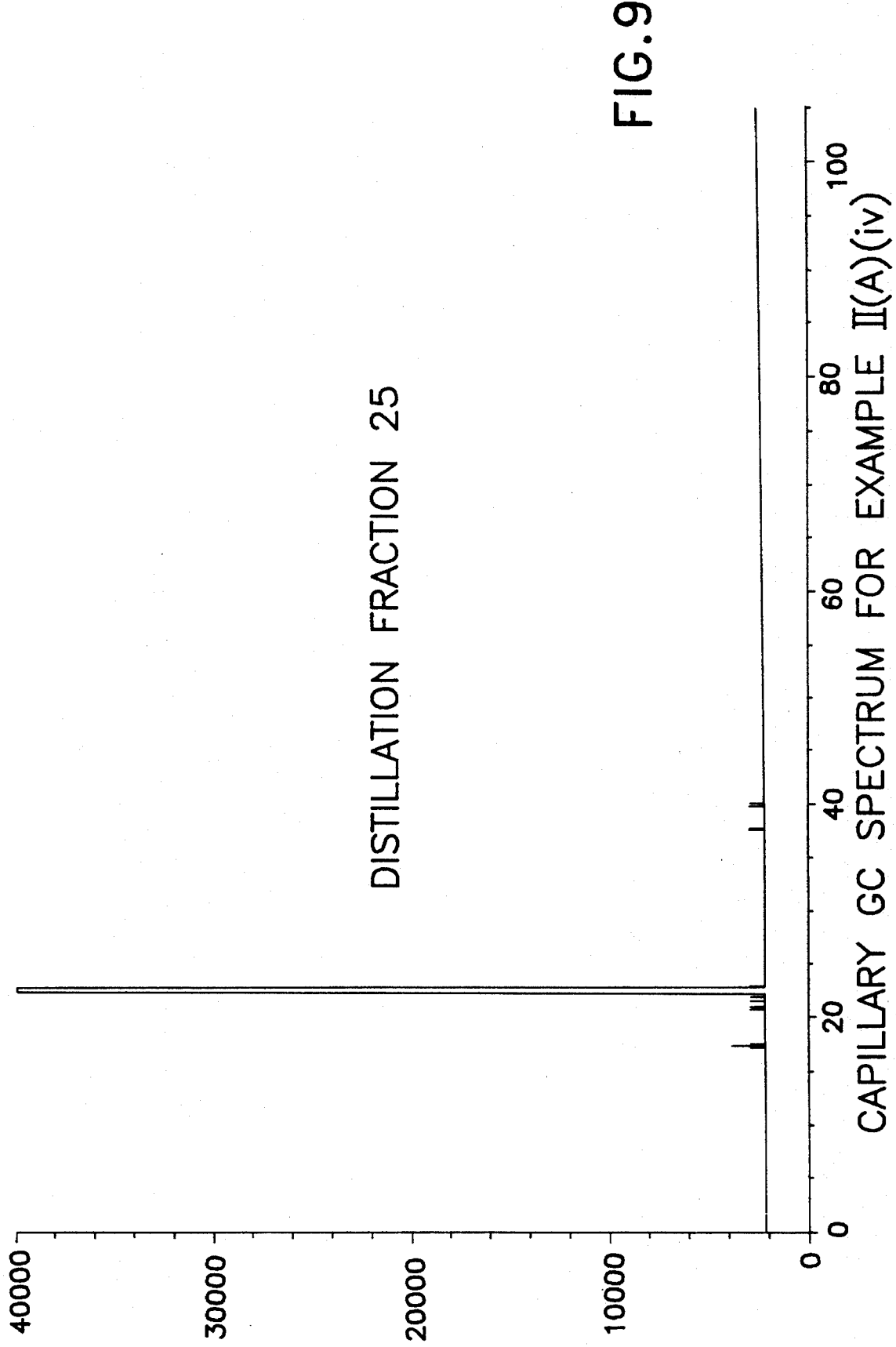

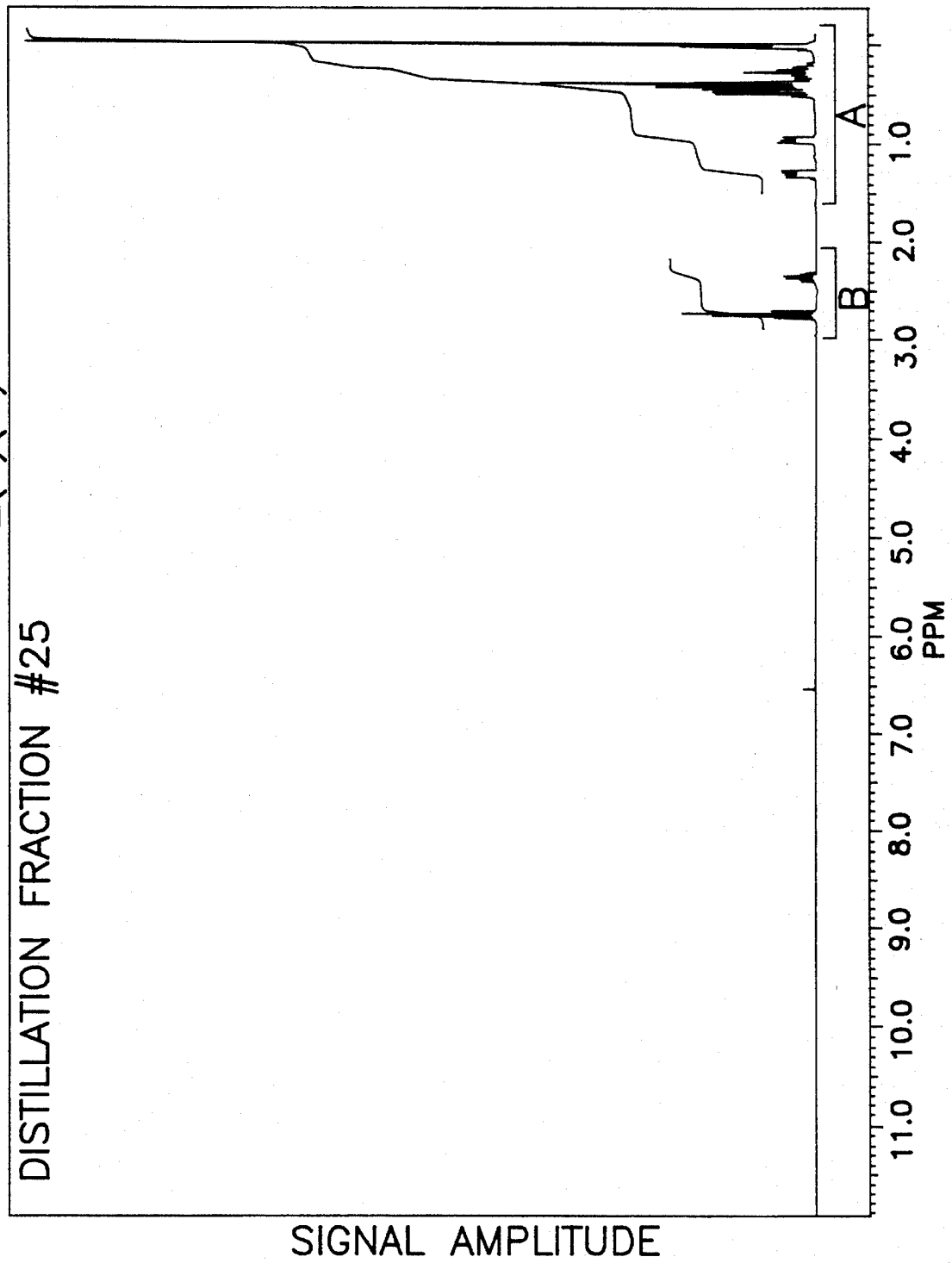

GLC PROFILE FOR EXAMPLE III(A)

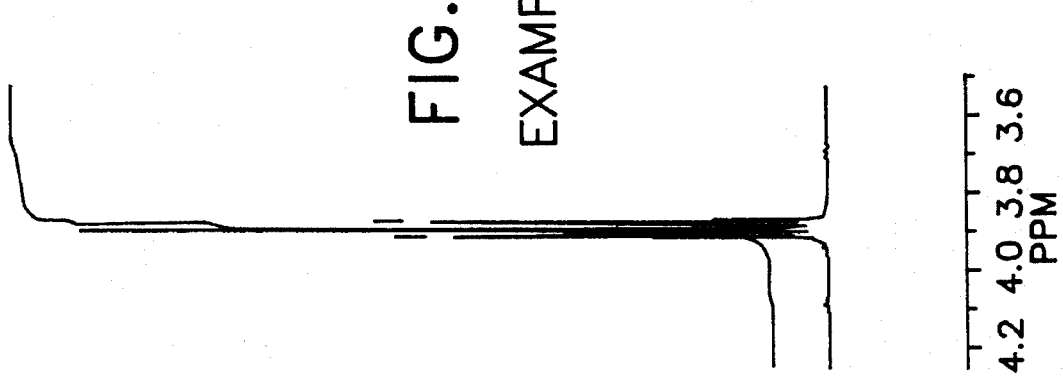
FIG.13(B) EXAMPLE III(A)
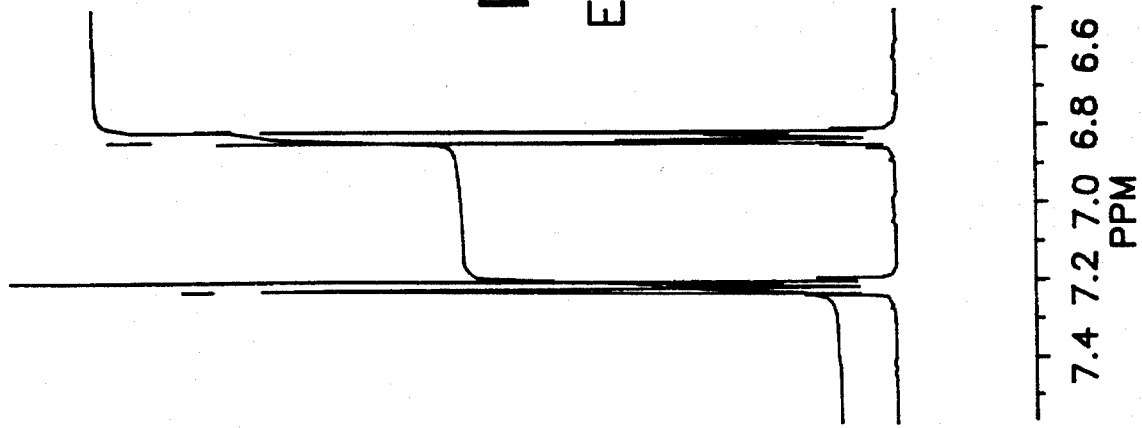
FIG.13(C) EXAMPLE III(A)

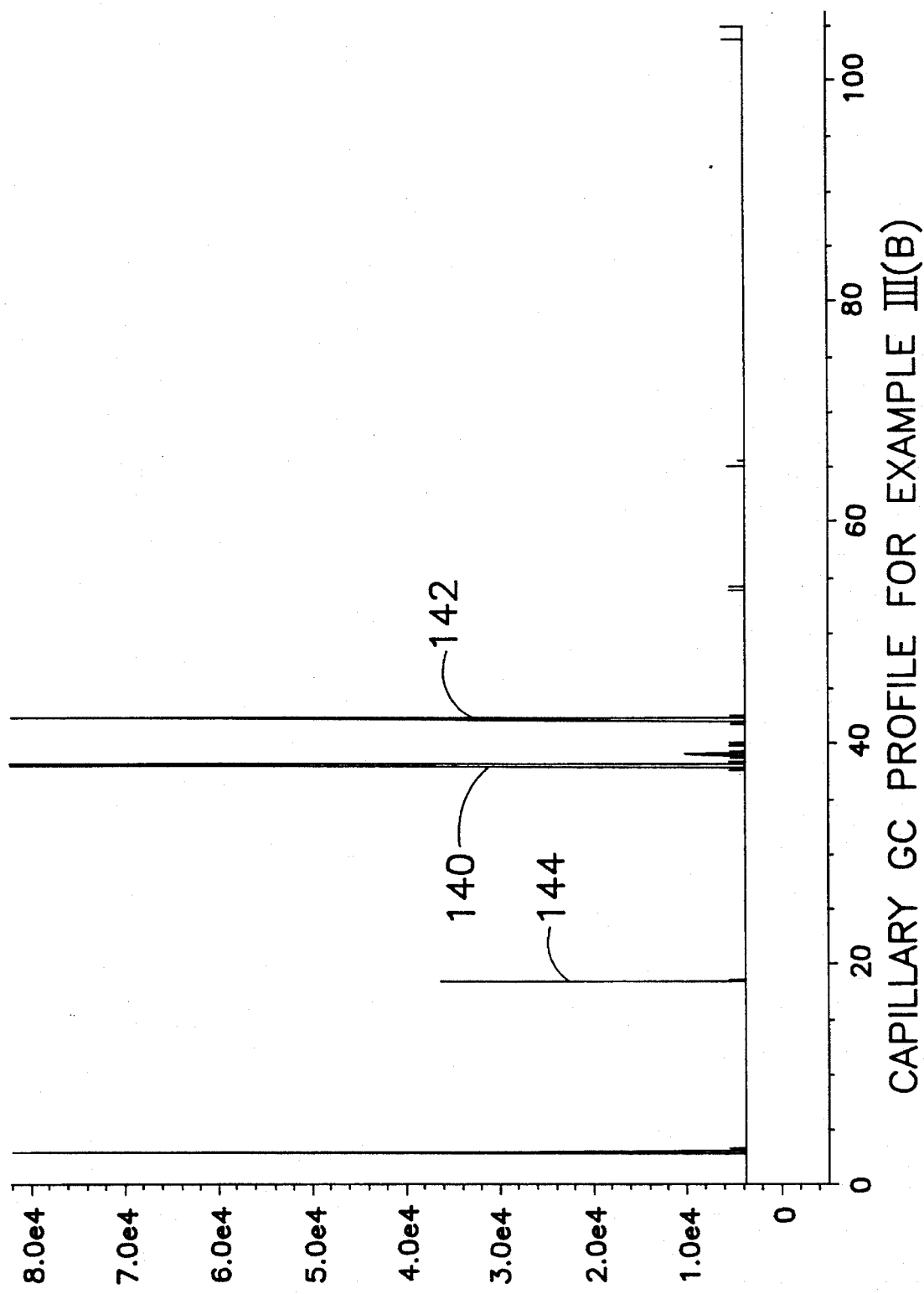

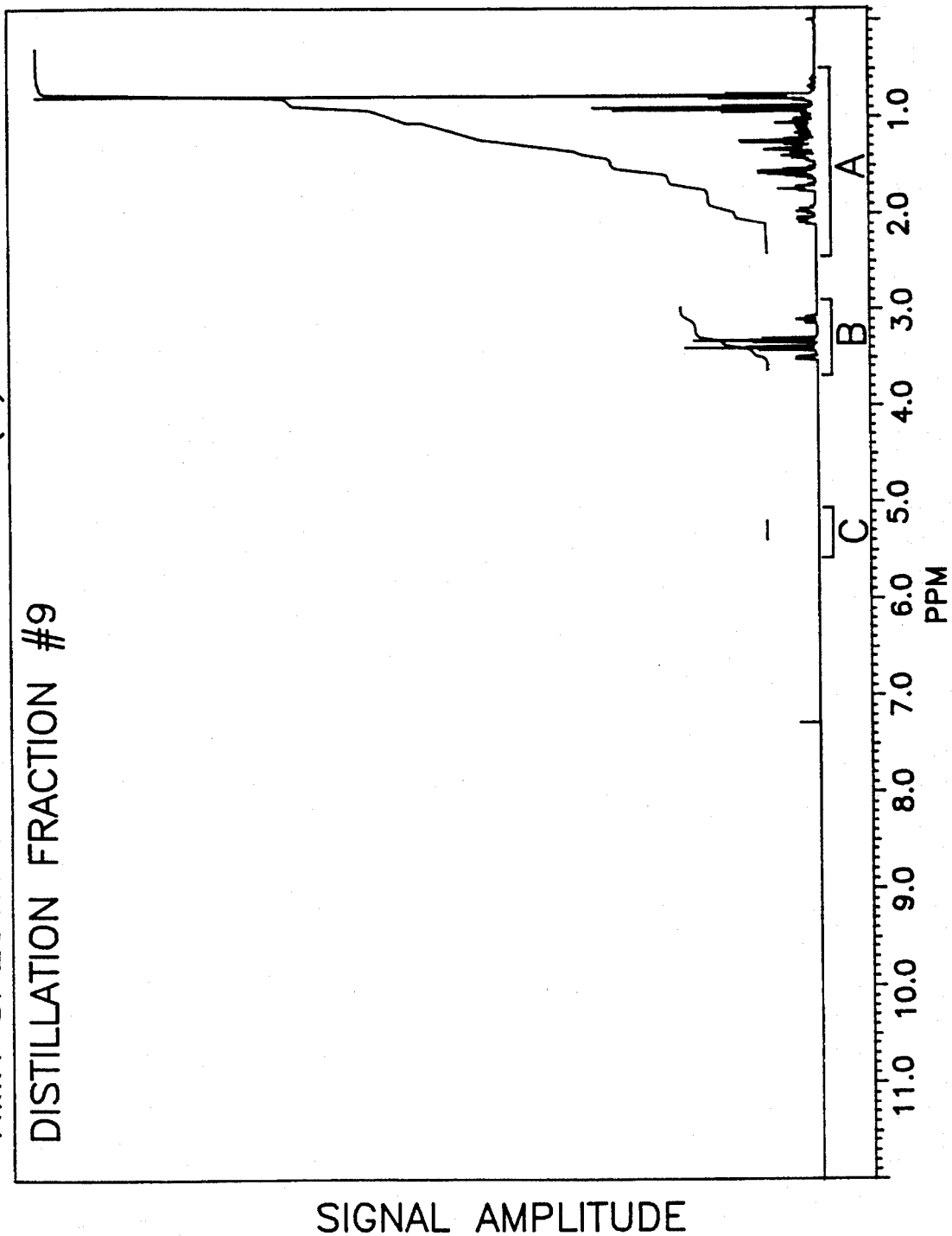

EXAMPLE III(B)
FRACTION #9

EXAMPLE III(B)
FRACTION #9

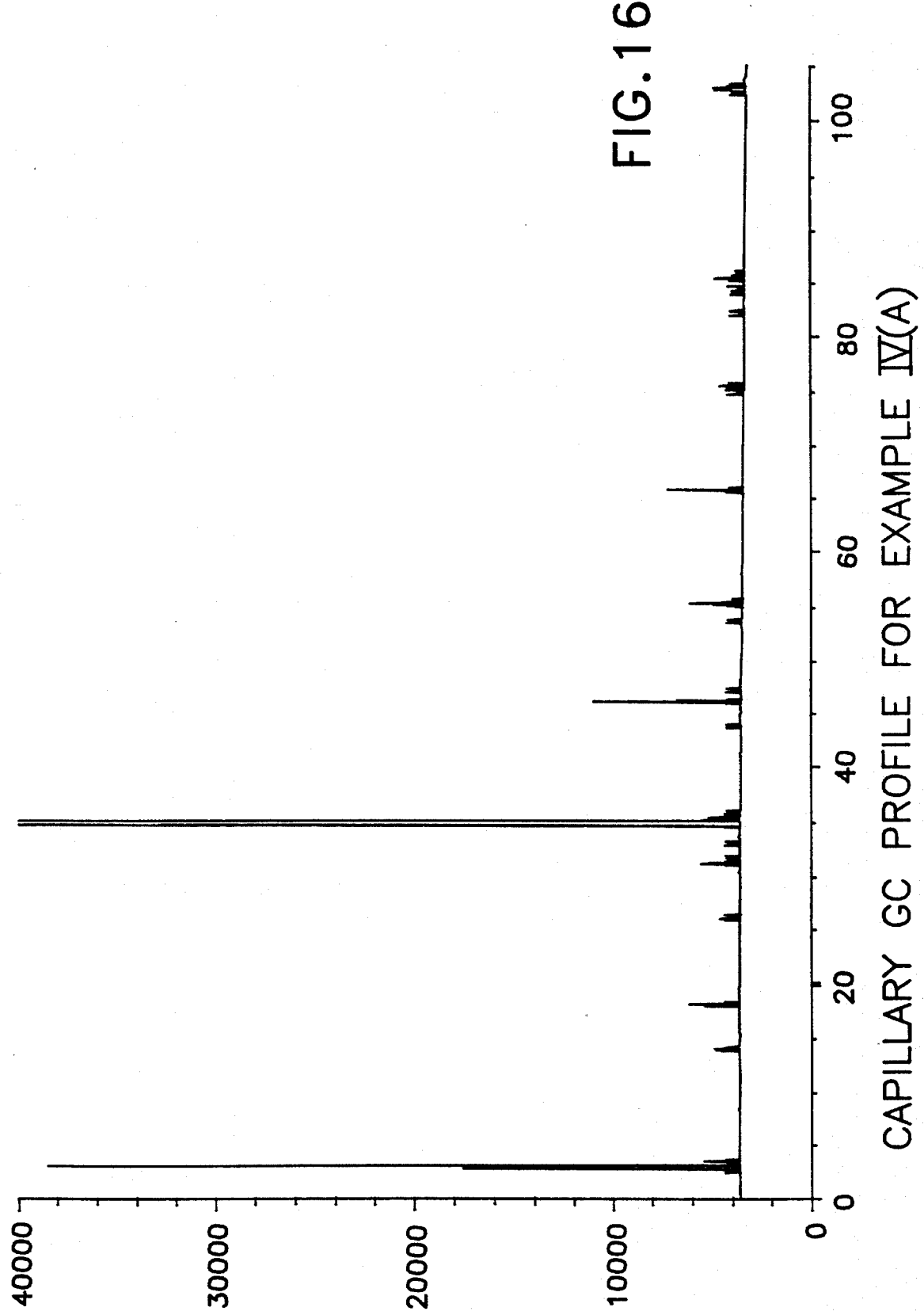
FIG. 16 CAPILLARY GC PROFILE FOR EXAMPLE IV(A)

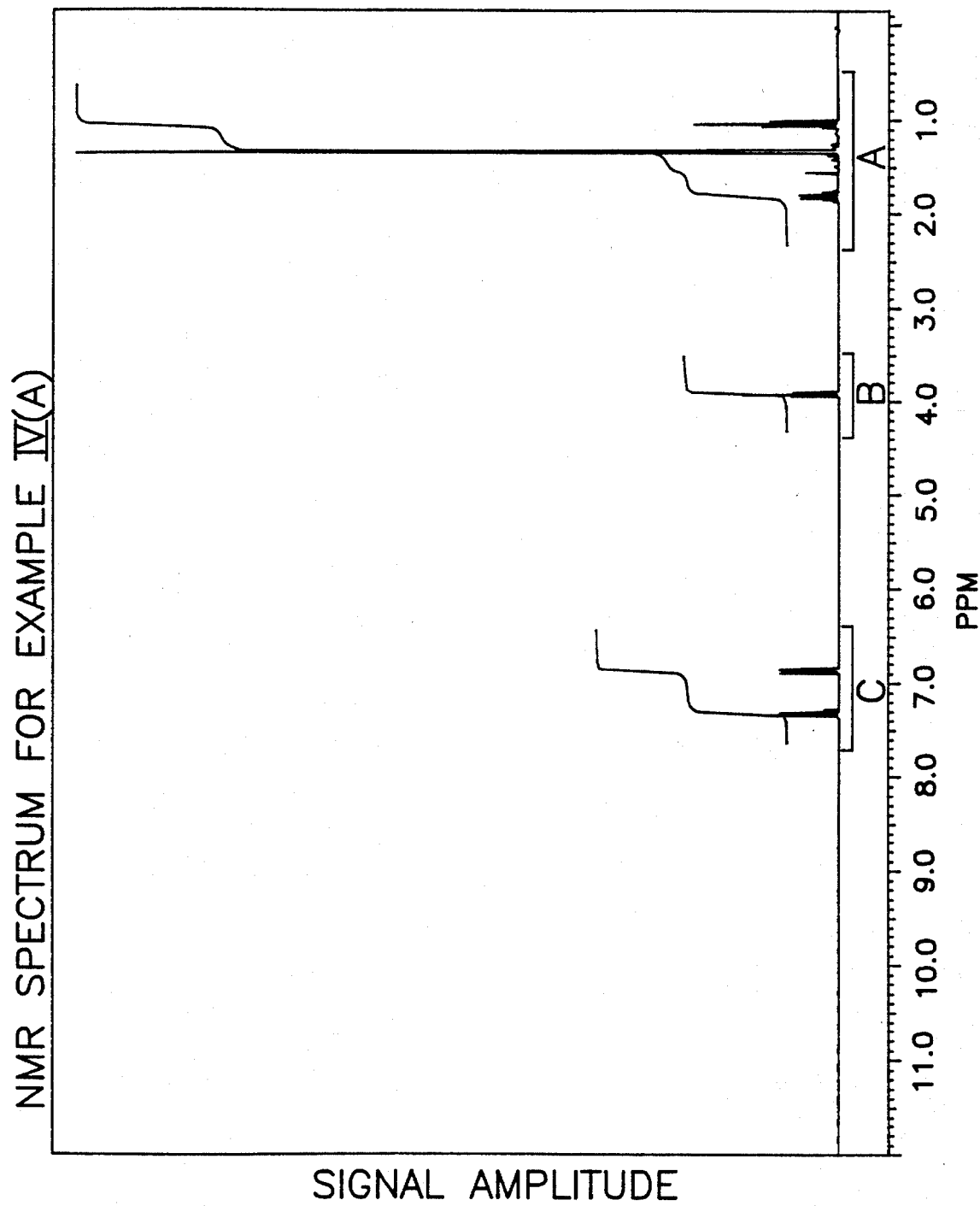

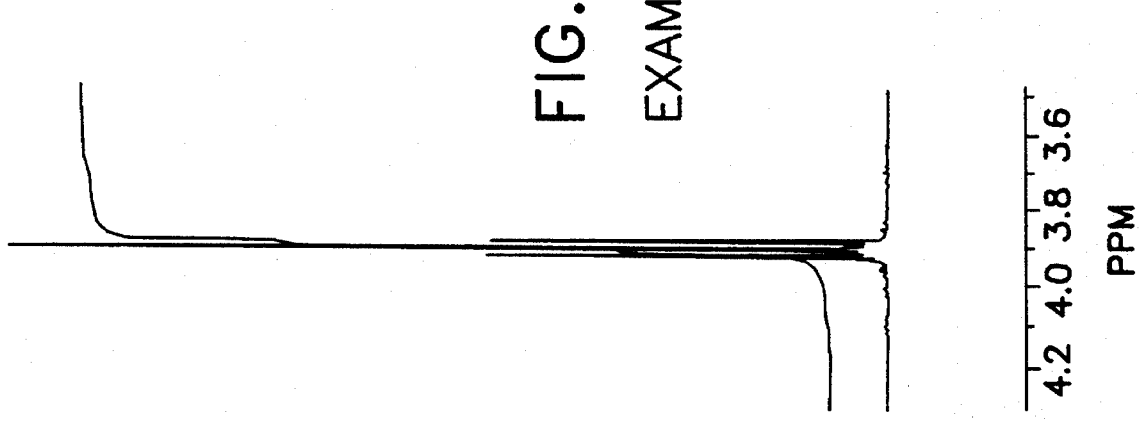
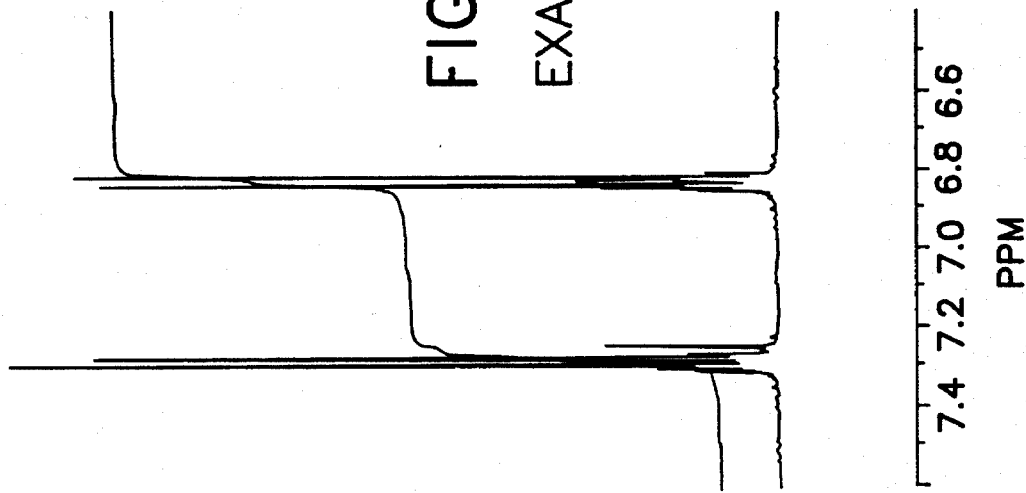

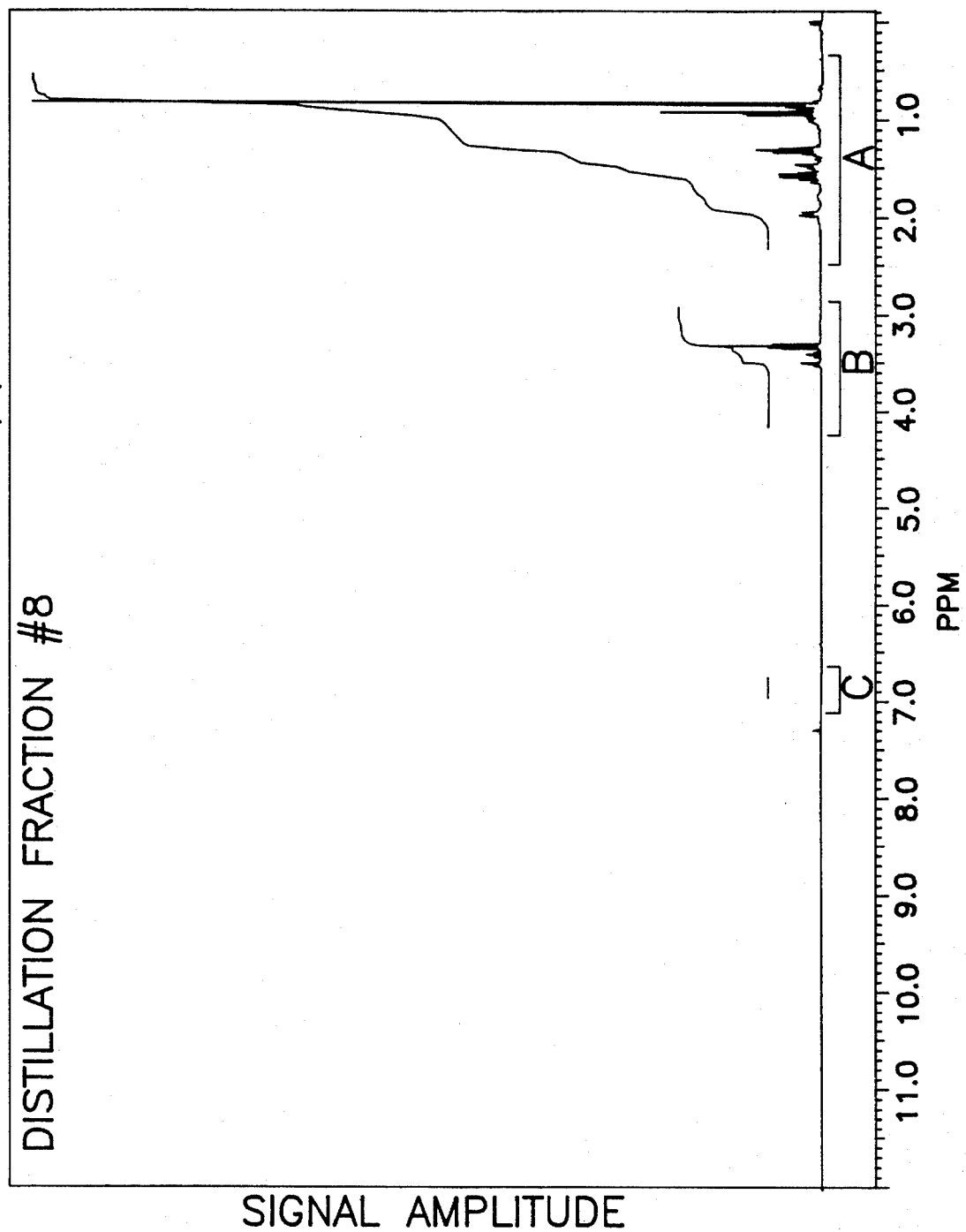

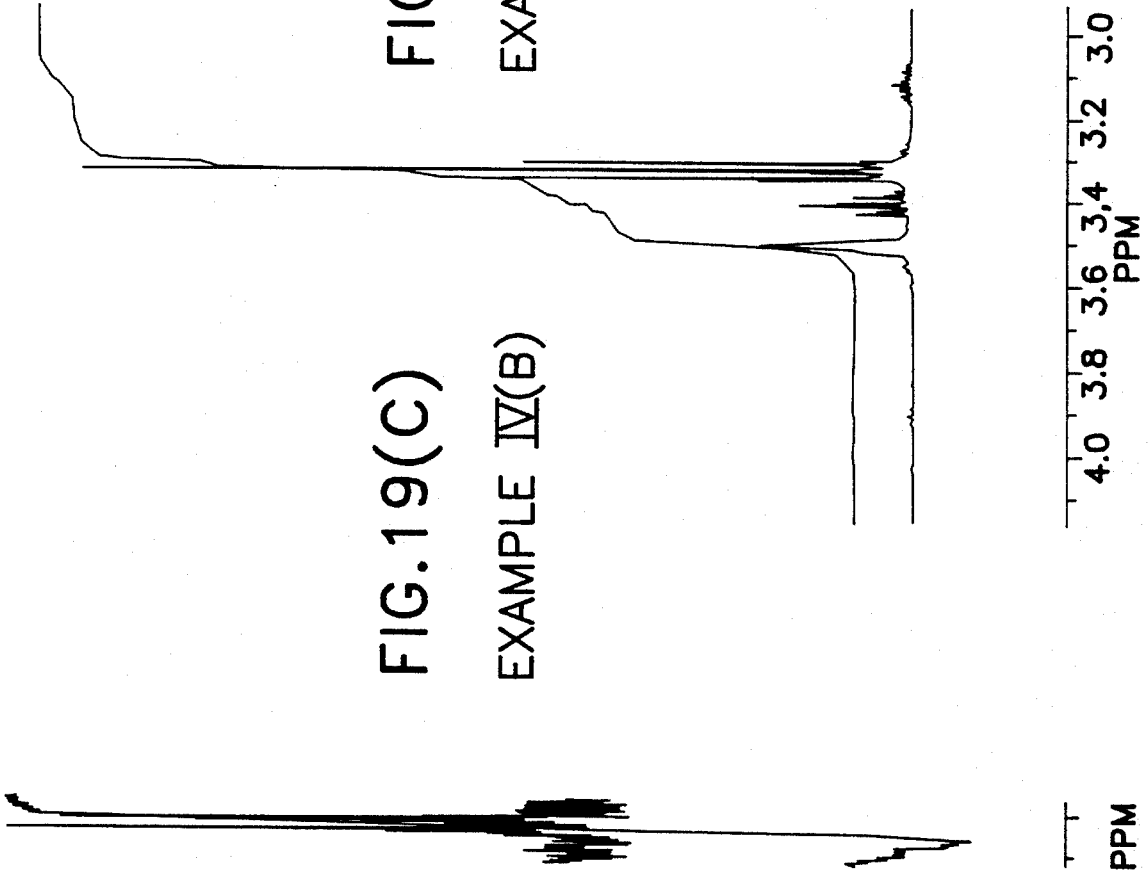

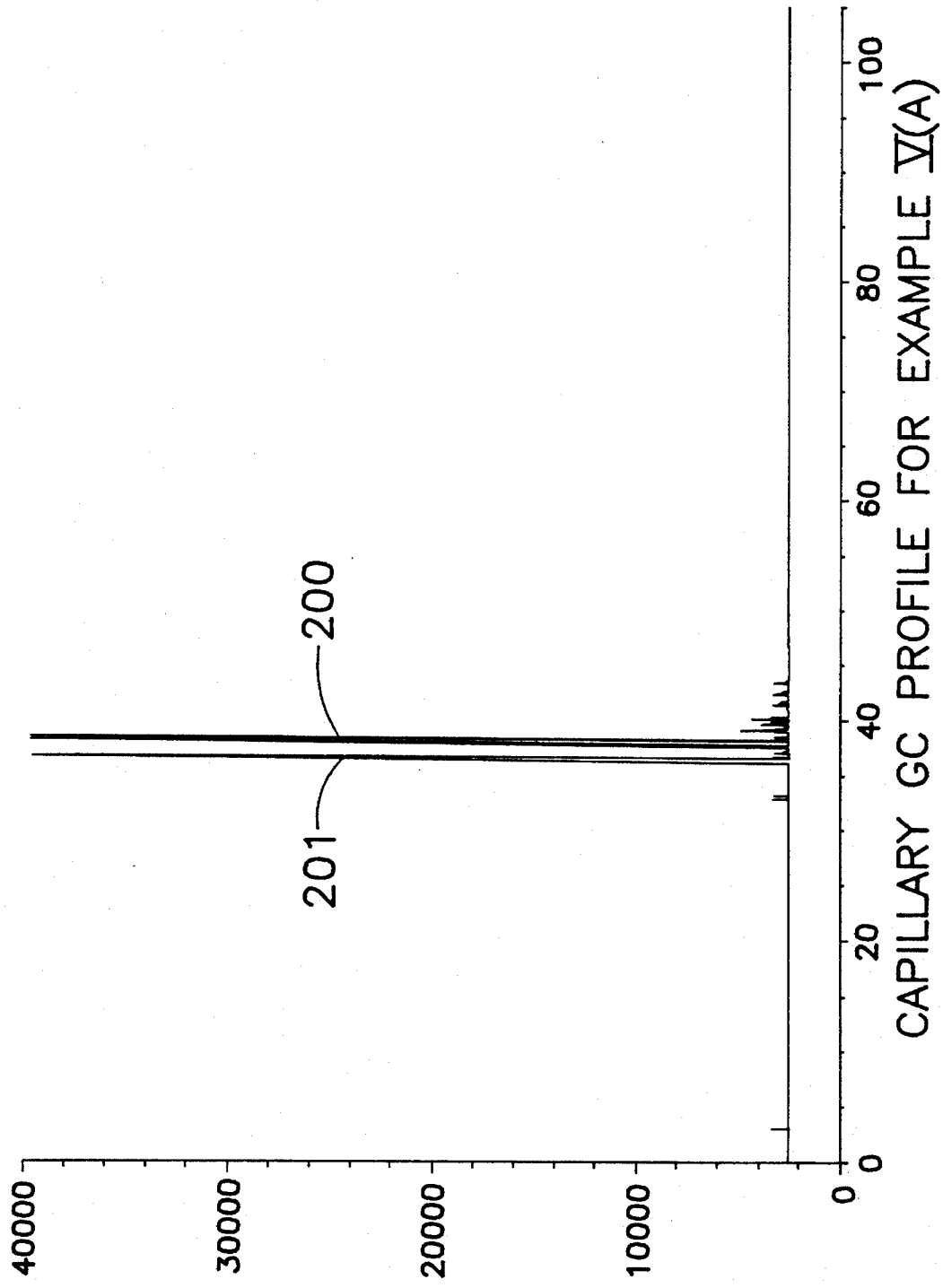

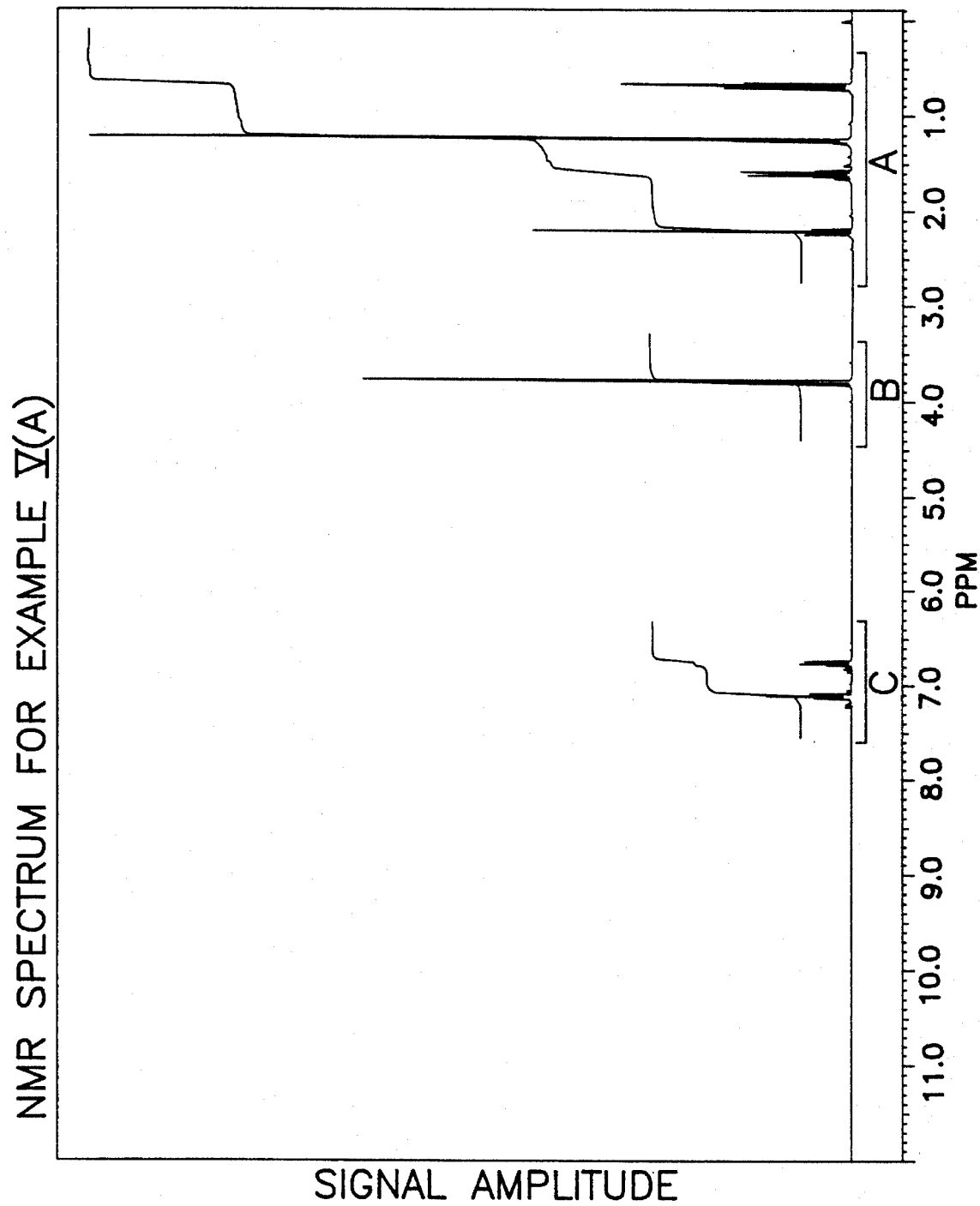

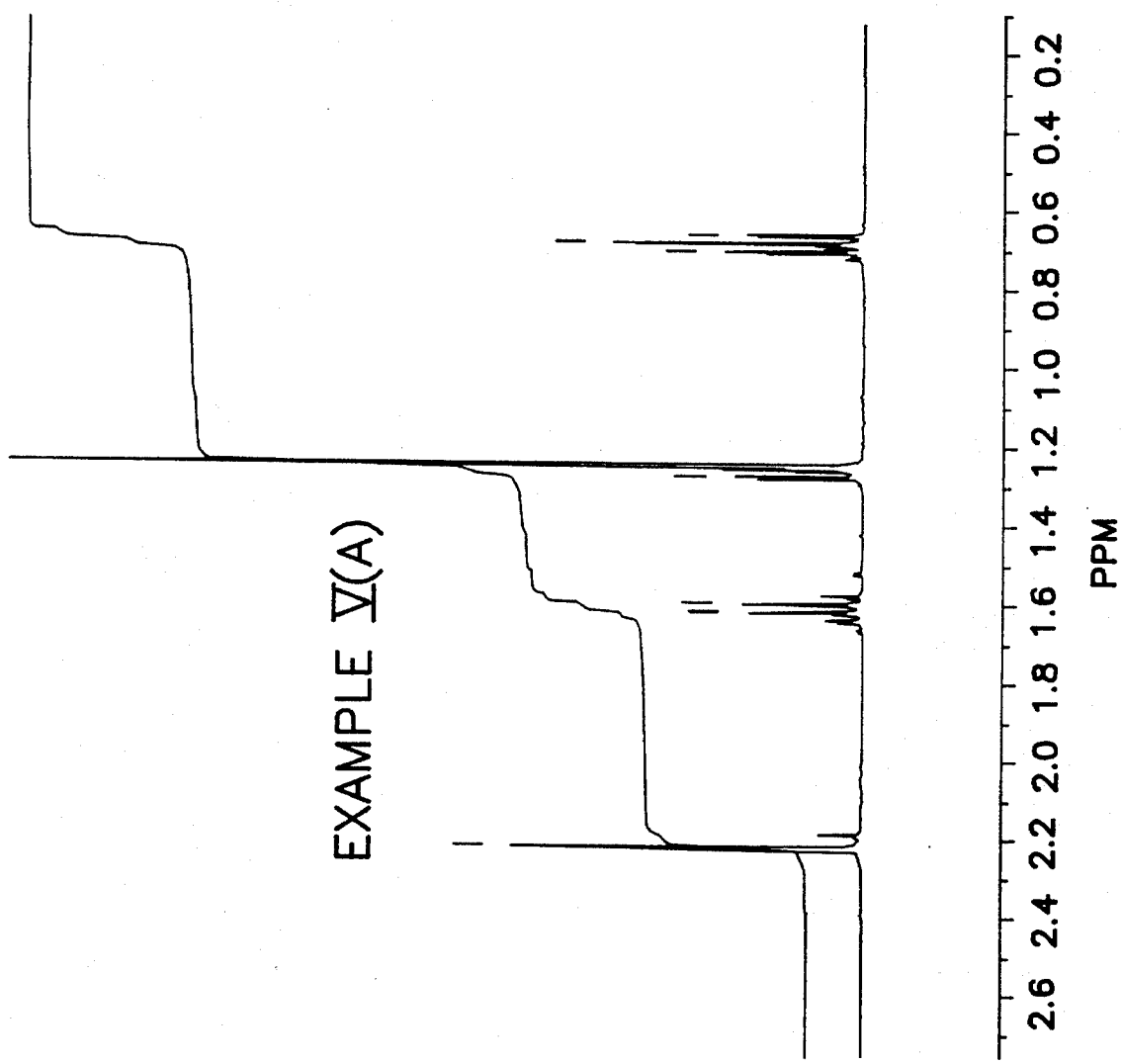

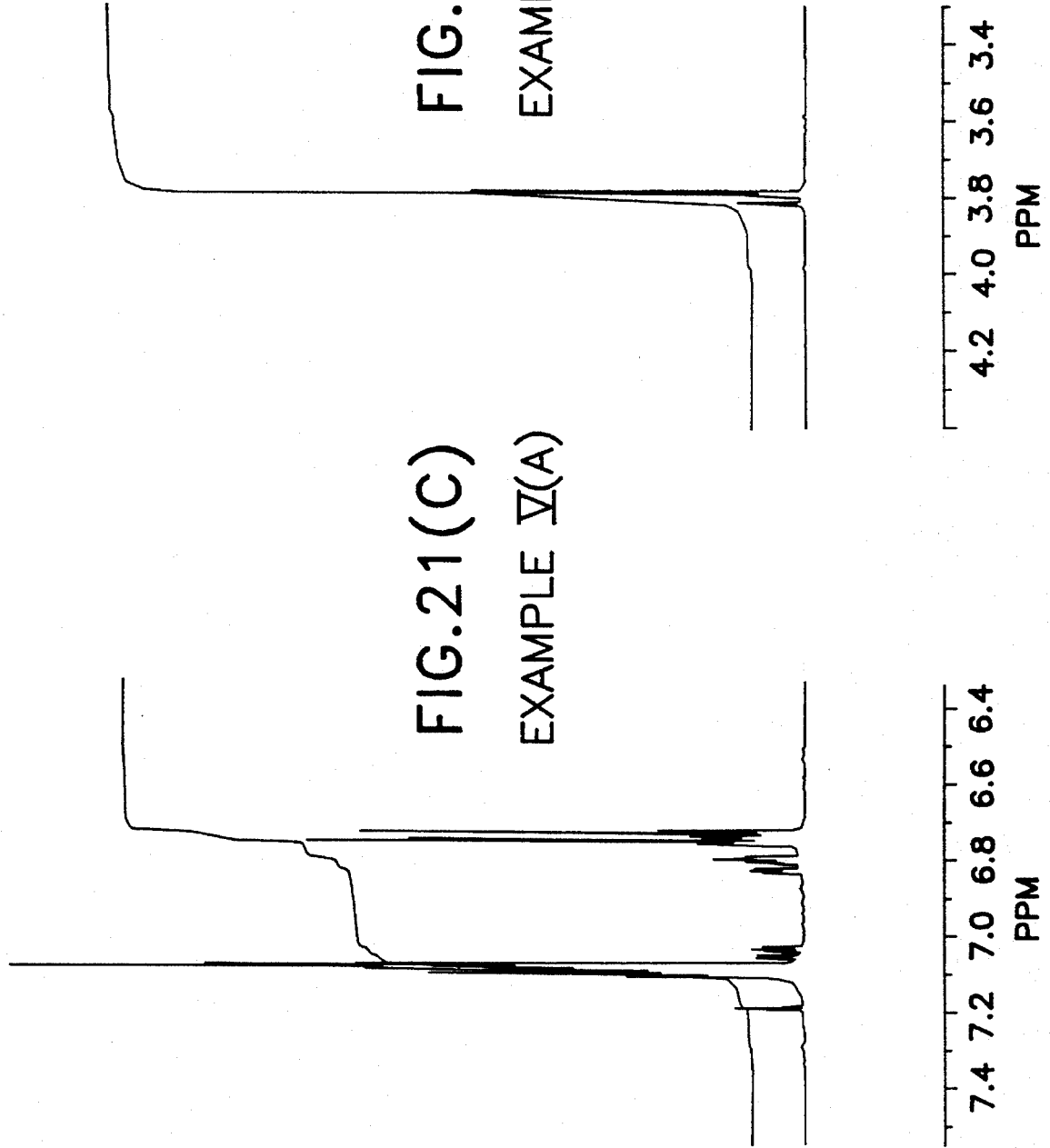

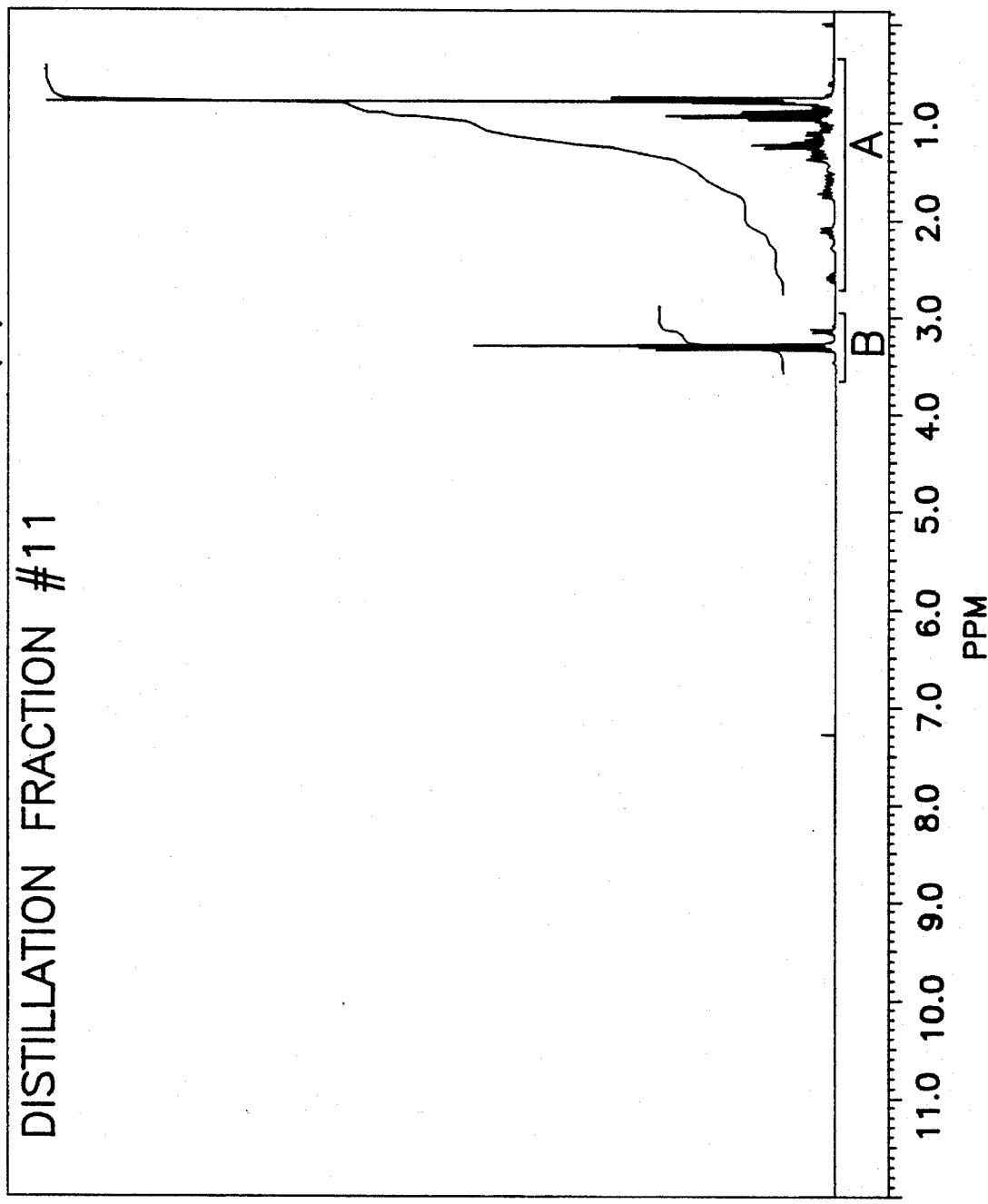

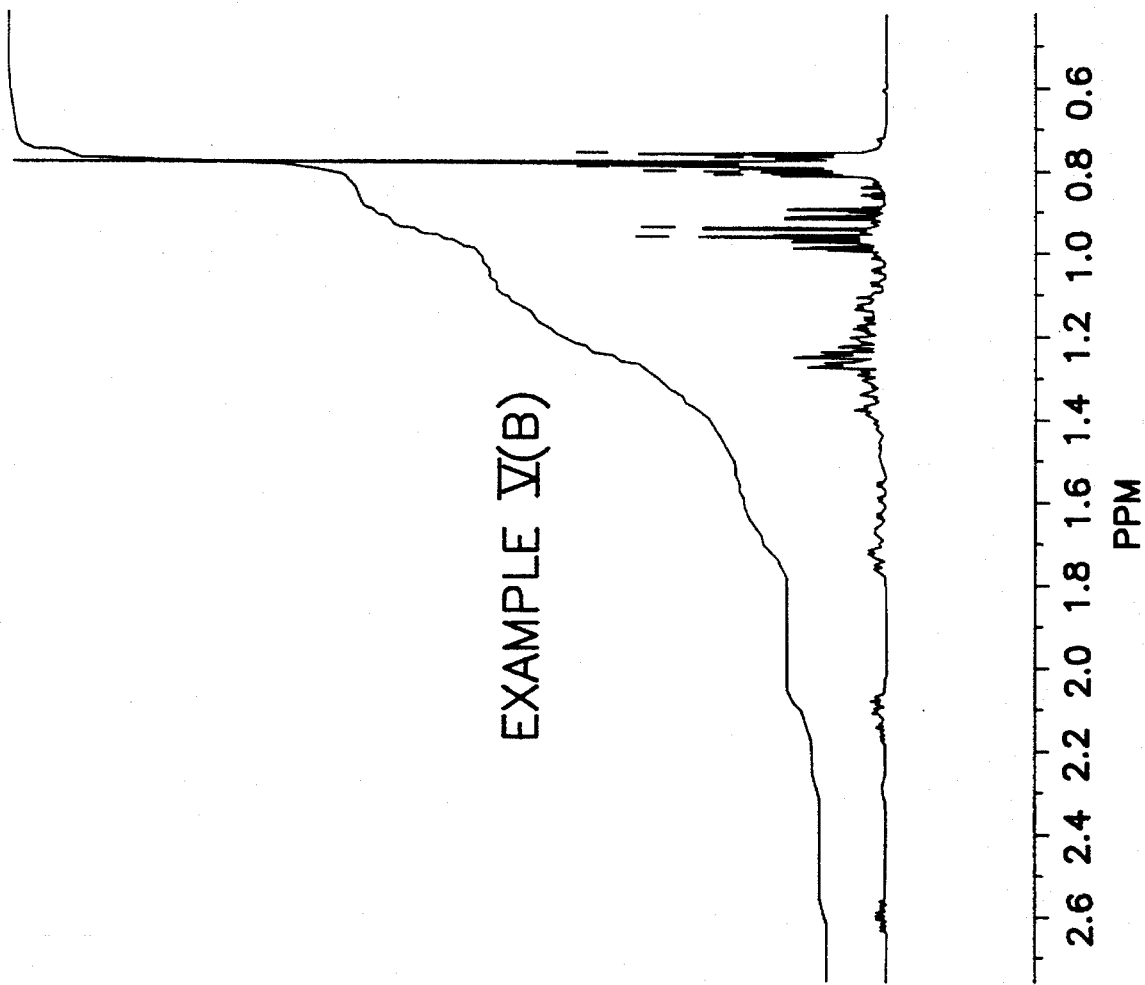

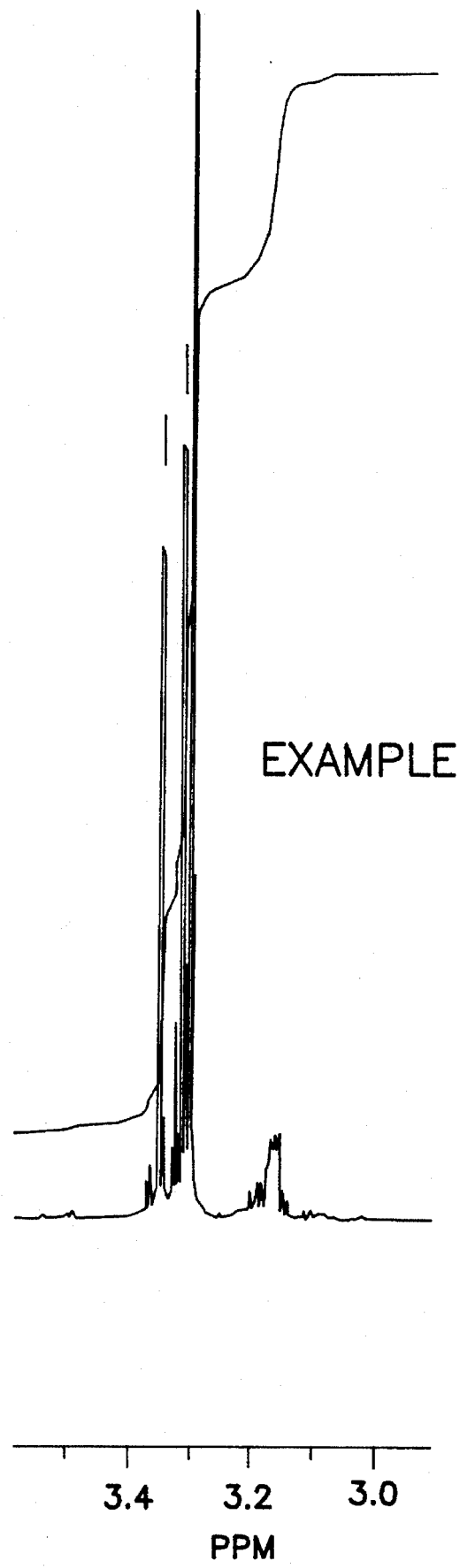
EXAMPLE V(B)

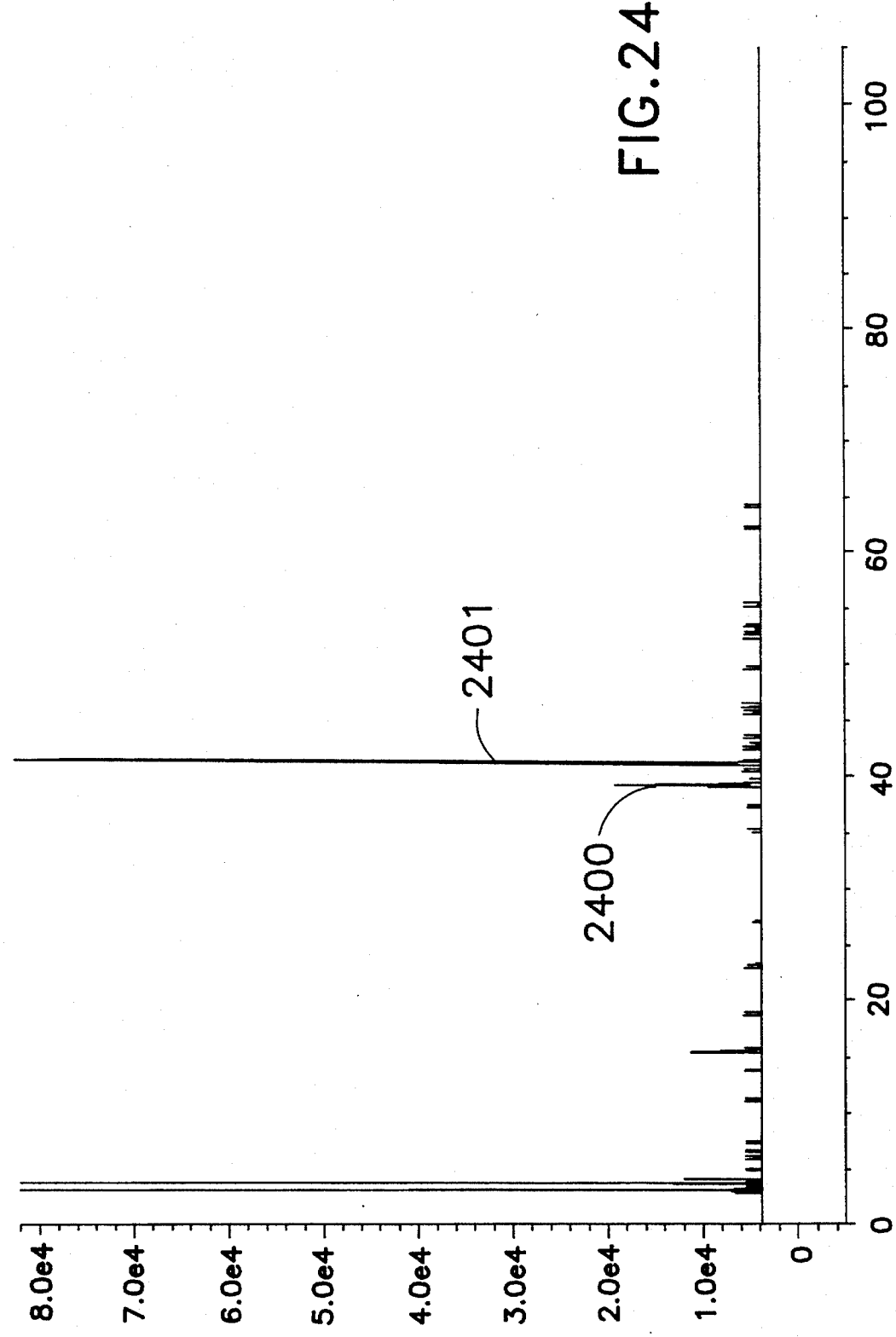

EXAMPLE VI(B)

EXAMPLE VI(B)

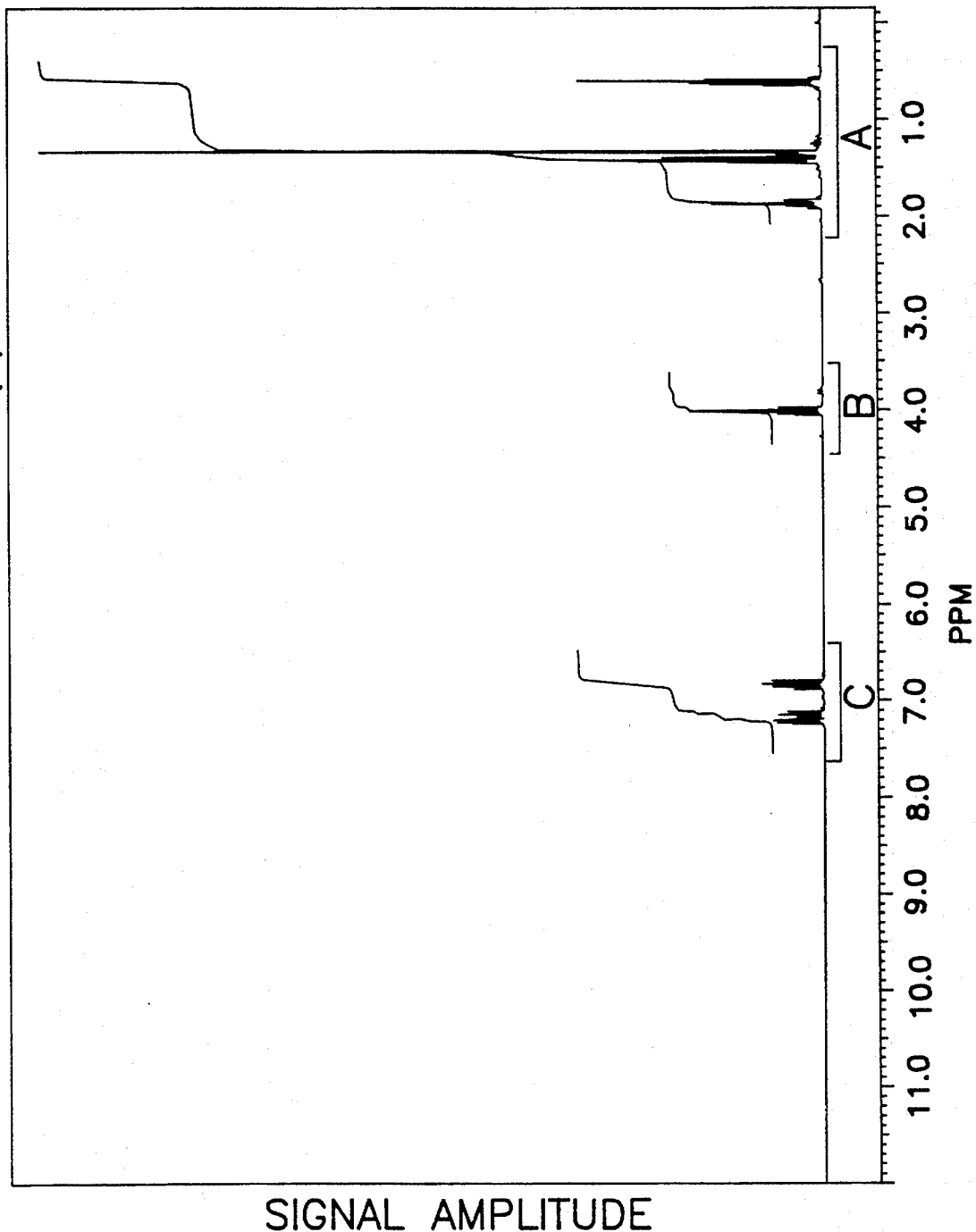

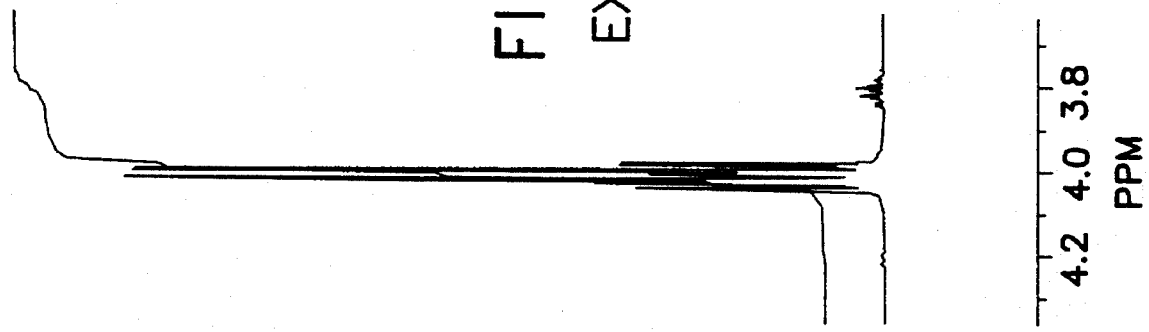
FIG.29(B) EXAMPLE VII(A)
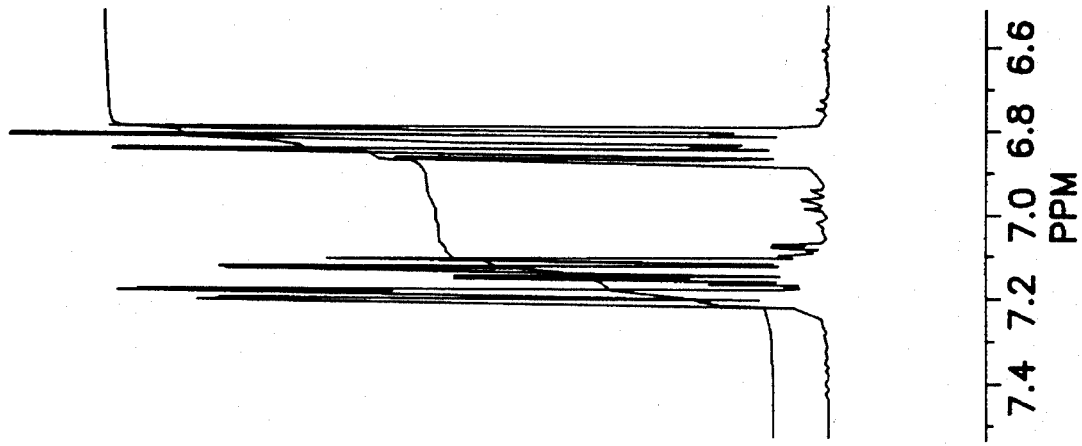
FIG.29(C) EXAMPLE VII(A)

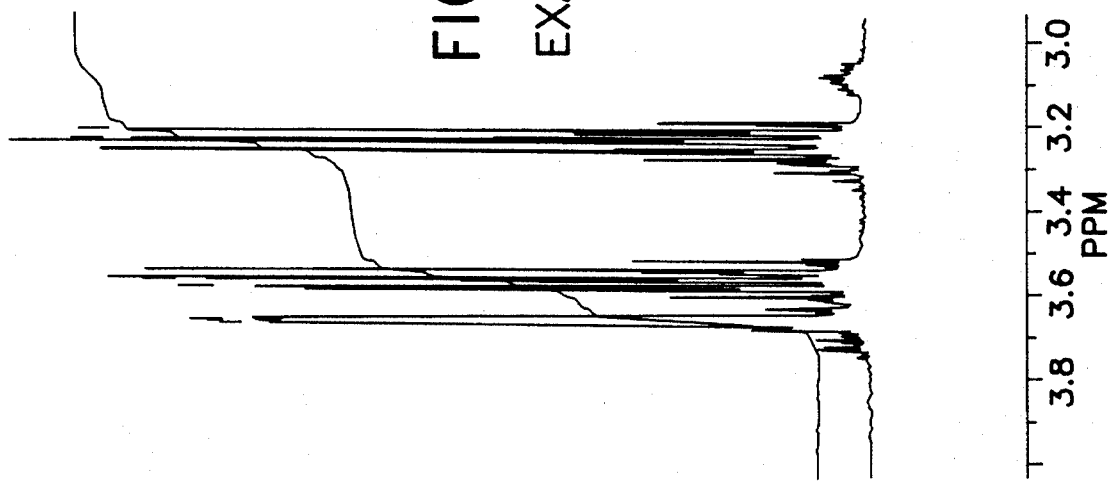
FIG.31(B) EXAMPLE VII(B)
FIG.31(C) EXAMPLE VII(B)

ALKYL-SUBSTITUTED-$C_1$-$C_3$ ALKOXY-$C_6$-CYCLOALIPHATIC COMPOUNDS, ORGANOLEPTIC USES THEREOF AND PROCESSES FOR PREPARING SAME

RELATED APPLICATIONS

This Application is a Continuation-in-Part of application for U.S. patent Ser. No. 08/522,122 filed on Aug. 31, 1995 now U.S. Pat. No. 5,543,398.

BACKGROUND OF THE INVENTION

The instant invention relates to alkyl-substituted-$C_1$-$C_3$ alkoxy-$C_6$-cycloaliphatic compounds defined according to the structure:

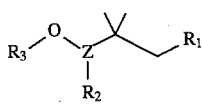

wherein Z represents meta or para cyclohexylene or meta or para phenylene and wherein $R_1$ and $R_2$ are the same or different hydrogen or methyl; and wherein $R_3$ represents $C_1$-$C_3$ alkyl; and wherein the moiety:

is ortho with respect to $R_2$ and para or meta with respect to the moiety:

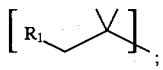

and uses of same in augmenting or enhancing the aroma of perfume compositions, perfumed articles and colognes.

There has been considerable work performed relating to substances which can be used to impart (modify, augment or enhance) fragrances to (or in) various consumable materials. These substances are used to diminish the use of natural materials, some of which may be in short supply and to provide more uniform properties in the finished product.

Long-lasting, intense, substantive green, fresh cut grass-like, leafy, woody, sweet, floral, muguet, balsamic, ozoney, waxy, fatty, aldehydic, citrusy, orange peel-like, privet hedge-like, cigar box-like, mahogany, dewy, rosy, twiggy, amber, cedarwood and earthy aromas with green, ozoney, woody, floral, muguet, minty camphorceous, piney, patchouli, rosy, celery leaf-like, fatty and aldehydic topnotes and linden blossom, cucumber, melon-like, ozoney, fatty, green, anise and fruity undertones are highly desirable in several types, of perfume compositions, perfumed articles and colognes (e.g., fruity and floral fragrances).

Perfume uses of ethoxycycloalkyl derivatives are well known in the literature. Thus, Arctander "*Perfume and Flavor Chemicals (Aroma Chemicals)*", Volume I, published in 1969 by the author at Monograph No. 713 discloses the compound having the structure:

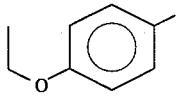

for use in perfumery. Arctander discloses that the compound having the structure:

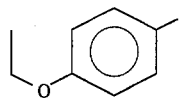

has a powerful, pungent-floral, deep-sweet, warm odor suggestive of ylang-ylang, pandanus and other exotic flowers. Arctander indicates that this compound is useful in perfume compositions of the heavy-floral type, in artificial ylang-ylang and in various types of soap perfumes and in general as a floralizer with considerable power. Arctander further states that the compound having the structure:

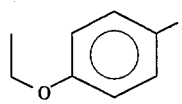

has a "peculiar nut-like, or earthy undertone". *Bielstein*, Volume EII 6, 488, H6, System 530a, 522–523 (abstract of Le Brazidec, *Bull. Soc. Chim.* France[4], 31, 263) discloses that the compound having the structure:

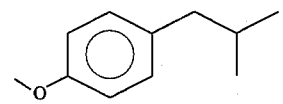

has an anisic aroma. The synthesis of this compound is disclosed by Le Brazidec and is further disclosed by Dutton, et al, *Canadian Journal of Chemistry*, 31 (1953), 1138, 1140. The structure:

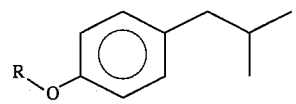

wherein R is methyl is shown by *Bielstein*, Volume E IV6 at page 3288 and is also disclosed at *Chemical Abstracts*, Volume 47, No. 2716h (abstract of J. Elisha Mitchell Sci. Soc., Volume 66, 171–4 (1950)). The compound having the structure:

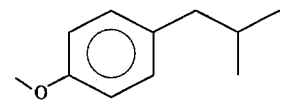

is also disclosed in Schoot, et al, U.S. Pat. No. 2,996,514.

The compounds having the structures:

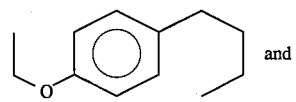

and

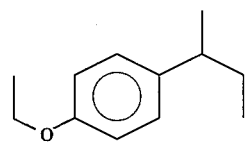

are indicated to be prepared by *Chemical Abstracts*, Volume 73, 1970, 66192c. The preparation of the compound having the structure:

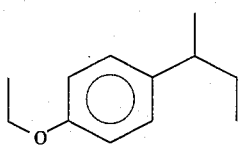

is also shown to be prepared by *Bielstein*, Volume E IV 6 at page 3280, *Chemical Abstracts*, 1961, 13386d (Zavgorodnii II) and *Chemical Abstracts*, Volume 49 (1955), No. 8848z (Zavgorodnii I).

Furthermore, the compound having the structure:

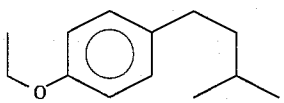

is shown to be prepared by Zavgorodnii III at *Chemical Abstracts*, Volume 71 (1969), No. 3088m. the compound having the structure:

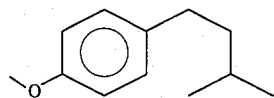

is shown to be prepared using the compound having the structure:

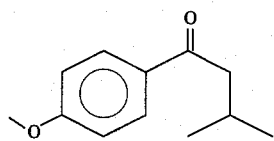

as a starting material according to the reaction:

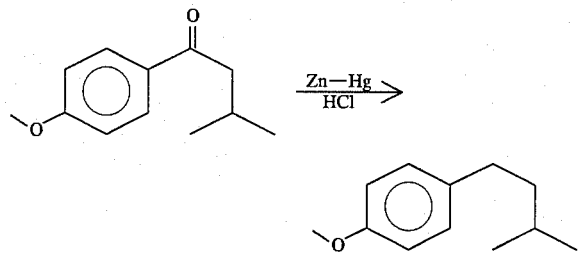

by *Bielstein*, E III 6, H6, 548. The compound having the structure:

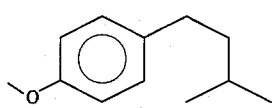

is shown to be prepared using as a starting material the compound having the structure:

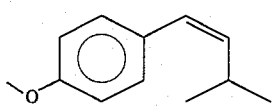

according to the reaction:

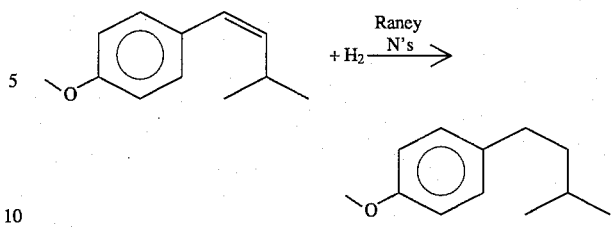

by *Bielstein*, E IV 6, page 3378 and by Dutton, et al, *Canadian Journal of Chemistry*, 31 (1953), pages 1138, 1142.

The compound having the structure:

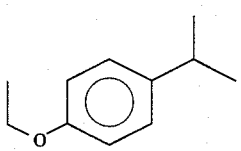

is shown to be prepared by Bielstein, E III 6, H6, 505-6, System No. 530, abstract of Ipatieff, et al, *Journal of American Soc.*, 60 (1938), 1161 and Bert, *Bull. Soc. Chim.*, 37, 1252–70 (1925).

U.S. patent Ser. No. 5,462,923 issued on Oct. 31, 1995, Monteleone, et al describes 1-oxo-substituted and unsubstituted isobutyl-4-ethoxy-benzenes and mixtures thereof with bicyclopentadiene derivatives for use in perfumery and further discloses methods for preparing same. Said Application for U.S. patent Ser. No. 08/428,420 is a Divisional of Application for U.S. patent Ser. No. 08/299,966 filed on Sep. 2, 1994 having the same title. Both Ser. Nos. 08/299,966 and 08/428,420 disclose the compounds having the structures:

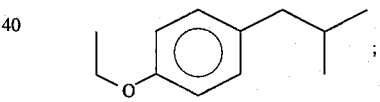

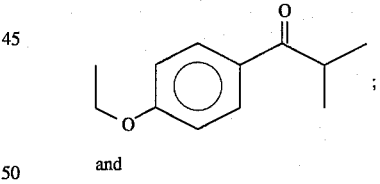

and

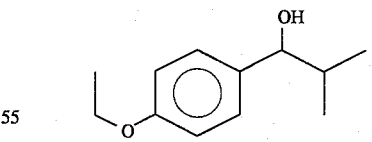

for use in perfumery and further disclose that these compounds have "long-lasting, intense, substantive green, woody, privet hedge (*Ligustrum vulgare*)-like, floral, lilac, ozoney, fennel and anisic aromas with fruity, fresh green, ozoney, fresh air, "ocean breeze" and anisic topnotes".

Alkylcyclohexanols are known to be useful in the field of perfumery. Thus, "VERTENEX®" is an article of commerce marketed by International Flavors & Fragrances Inc., said "VERTENEX®" having the structure:

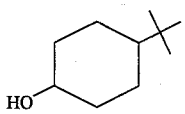

Furthermore, "VERTENEX® HIGH CIS" is also an article of commerce marketed by International Flavors & Fragrances Inc., which has the structure:

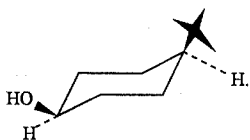

Furthermore, "ORIVONE", also an article of commerce marketed by International Flavors & Fragrances Inc., has the structure:

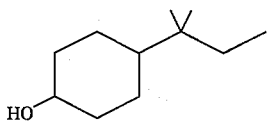

Para alkylcyclohexylalkyl ethers are known in the prior art. Thus, Eliel, et al, *Chemical Abstracts*, Volume 63, 1965, 3011g (abstract of *J. Org. Chem.* 30(3), pages 848–854) discloses the compound having the structure:

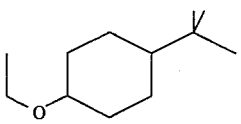

Faillebin, *Beilstein*, Volume EII 6 at H7, No. 2, discloses the compound having the structure:

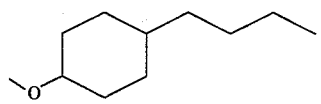

(abstract of Faillebin, *ANN. CHIM.* 4, 156–82, 410–96 (1925)). Hiromu, et al, *Chemical Abstracts*, Volume 108, 1988 at monograph No. 108:62302g, discloses the compound having the structure:

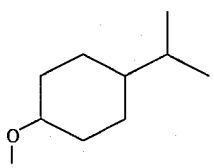

as being a component of an essential oil obtained from the root of *Glycyrrhiza glabra* (abstract of *Nippon Nogei Kagaku Kashi* 1987, 61(9), pages 1119–21 (Japan)). However, the aroma of this material is not disclosed nor is it indicated that the compound having the structure:

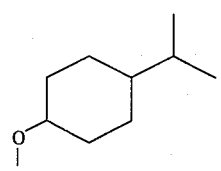

contributes any aroma to the essential oil named.

Becker, et al in "The Relation of Structure and Odor in Substituted Cyclohexanols", *Perfumer & Flavorist*, Volume 15, November/December 1990 at pages 29–33 discloses the compounds having the structures:

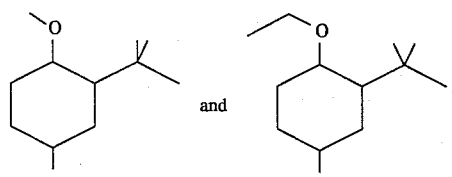

as having floral, fruity and earthy aroma profiles.

The alkyl-substituted-$C_1$–$C_3$ alkoxy-$C_6$-cycloaliphatic compounds of our invention have structures different in kind and have aromas which are unexpectedly and unobviously advantageous over the aromas of the compounds having the structures:

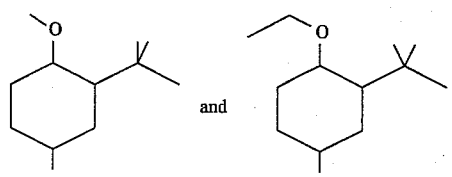

Thus, nothing in the prior art discloses the unexpected, unobvious and advantageous organoleptic properties of the alkyl-substituted-$C_1$–$C_3$ alkoxy-$C_6$-cycloaliphatic compounds of our invention.

BRIEF DESCRIPTION OF THE DRAWINGS

FIG. 1 is the capillary GC profile for the crude reaction product of Example I(A) containing the compound having the structure:

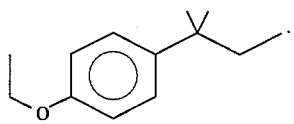

FIG. 2 is the NMR spectrum for the compound having the structure:

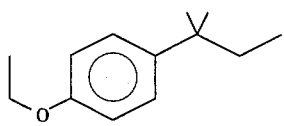

prepared according to Example I(A)

FIG. 3 is the capillary GC profile for the reaction product of Example I(B) containing the compounds having the structures:

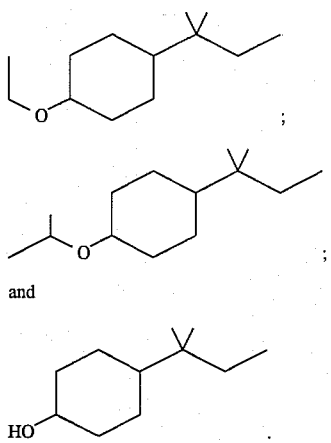

FIG. 4 is the NMR spectrum for distillation fraction No. 4 of the distillation of the reaction product of Example I(B) for the compound having the structure:

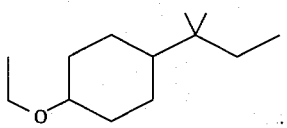

FIG. 4(A) is an enlargement of section "A" of the NMR spectrum of FIG. 4.

FIG. 4(B) is an enlargement of section "B" of the NMR spectrum of FIG. 4.

FIG. 5(A) is a capillary GC spectrum for the reaction product of Example II(A)(i) containing in a ratio of 48:52 a mixture of the cis and trans isomers having the structures, respectively:

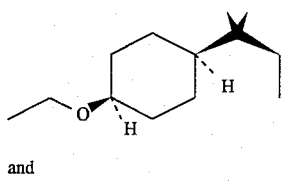

and

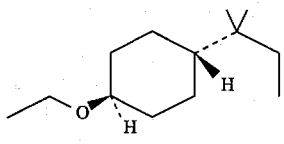

(conditions: 50 meter×0.32 mm bonded, fused silica/methyl silicone column (OV1) programmed from 75° up to 225° C. at 2.0° C. per minute). Shown on the capillary GC spectrum, also, is the impurity having the structure:

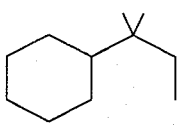

FIG. 5(B) is a capillary GC spectrum for the reaction product of Example II(A)(ii) containing the compounds having the structures:

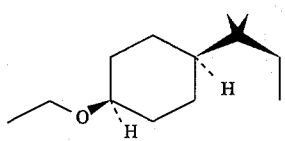

and

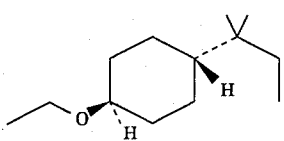

(in a ratio of 48:52) as well as the impurity having the structure:

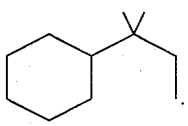

(Conditions: 50 meter×0.32 mm bonded, fused silica/methyl silicone column programmed from 75° up to 225° C. at 2° C. per minute.)

Figure 6:
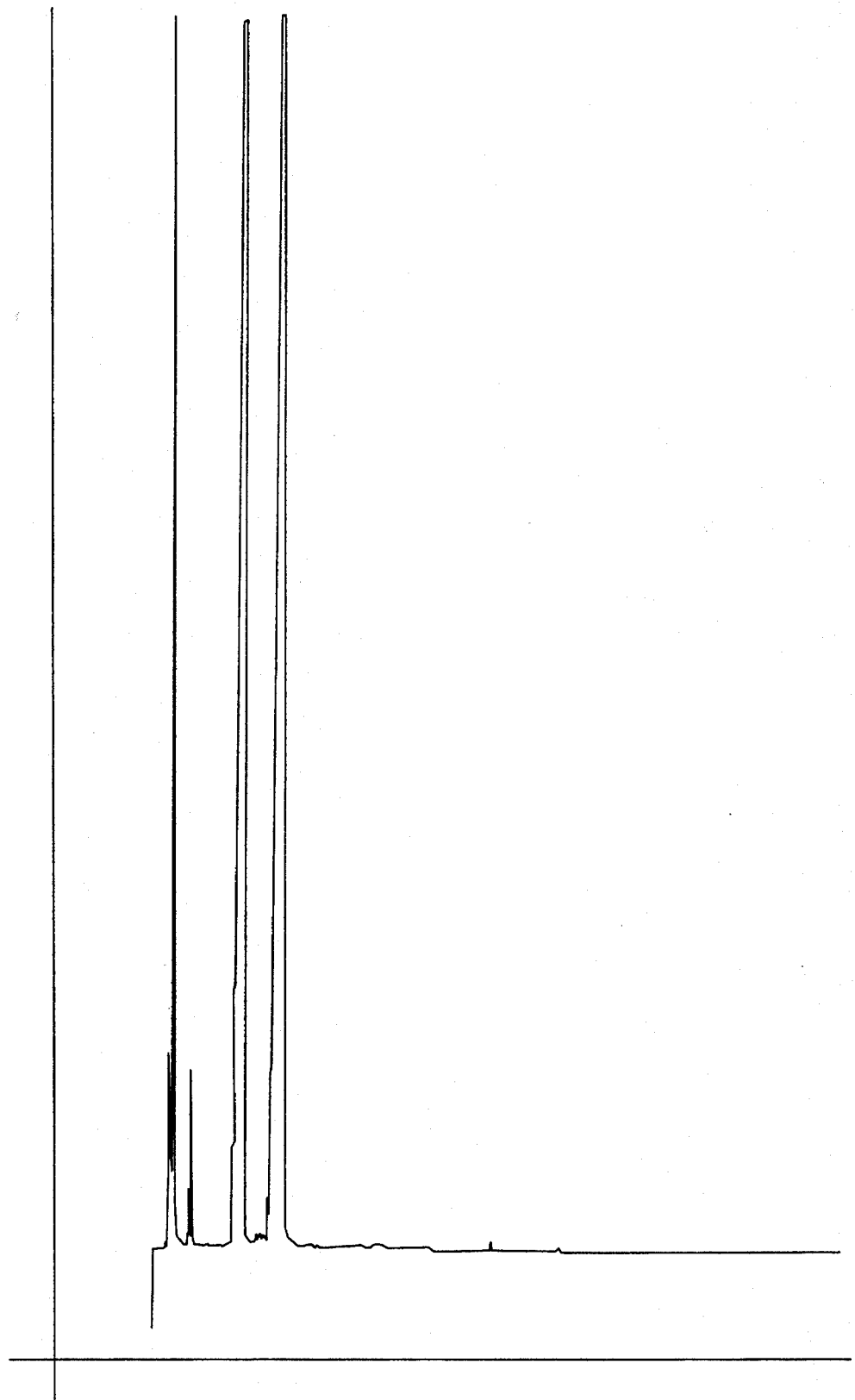

FIG. 6 is a GC profile for the reaction product of Example II(A)(iii) containing the compounds having the structures:

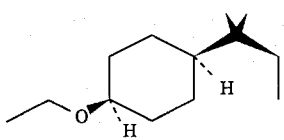

and

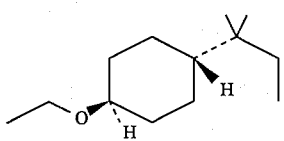

(conditions: carbowax column programmed at 160° C. isothermal).

Figure 7:
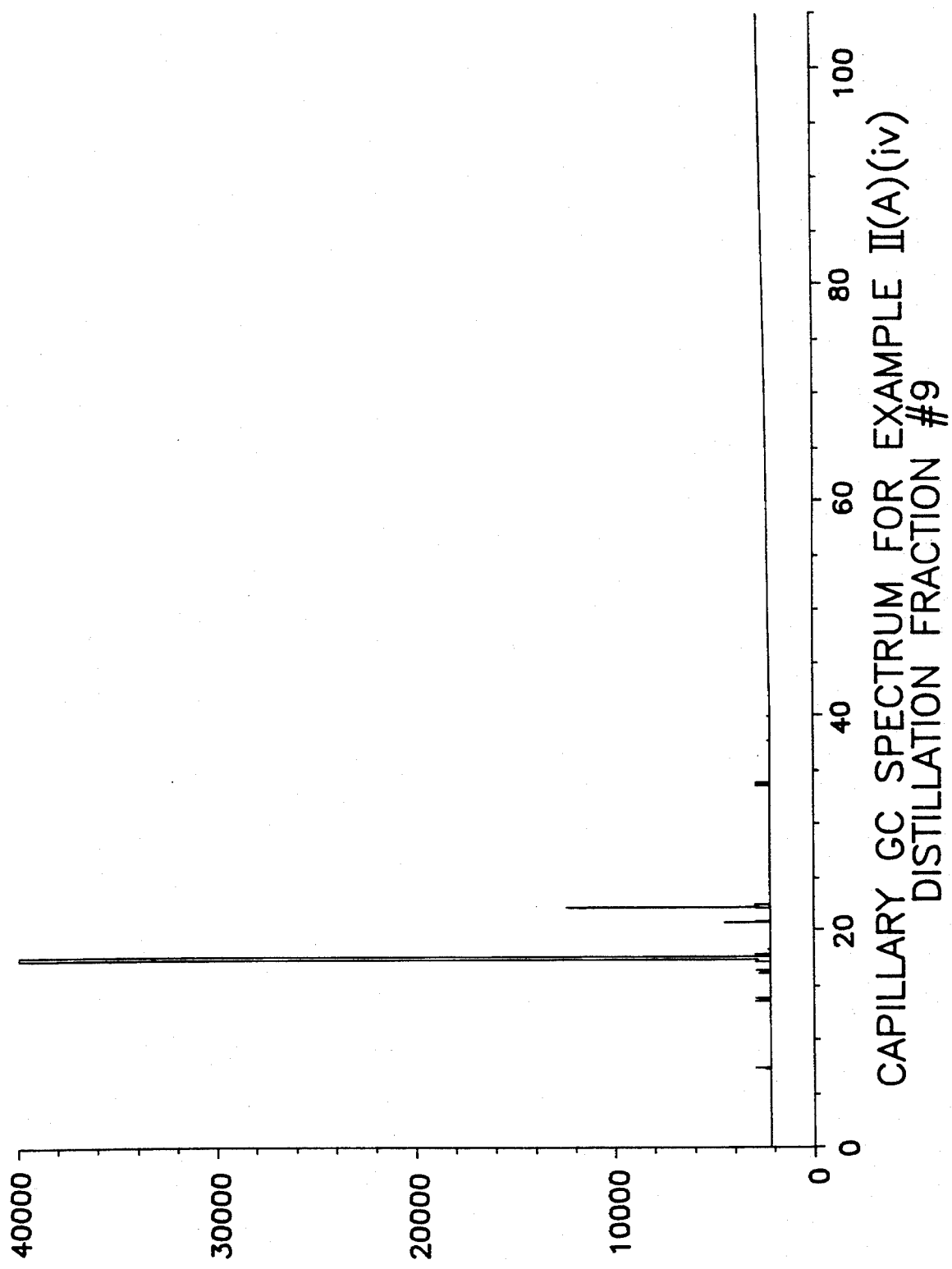

FIG. 7 is a capillary GC spectrum for distillation fraction 9 of Example II (A) (iv). Distillation fraction 9 contains 97% of the cis isomer having the structure:

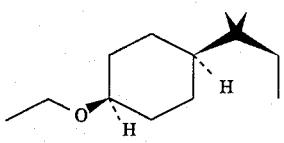

(conditions: 50 meter×0.32 mm carbowax 20M column programmed from 75° up to 225° C. at 2.0° C. per minute).

Figure 8:
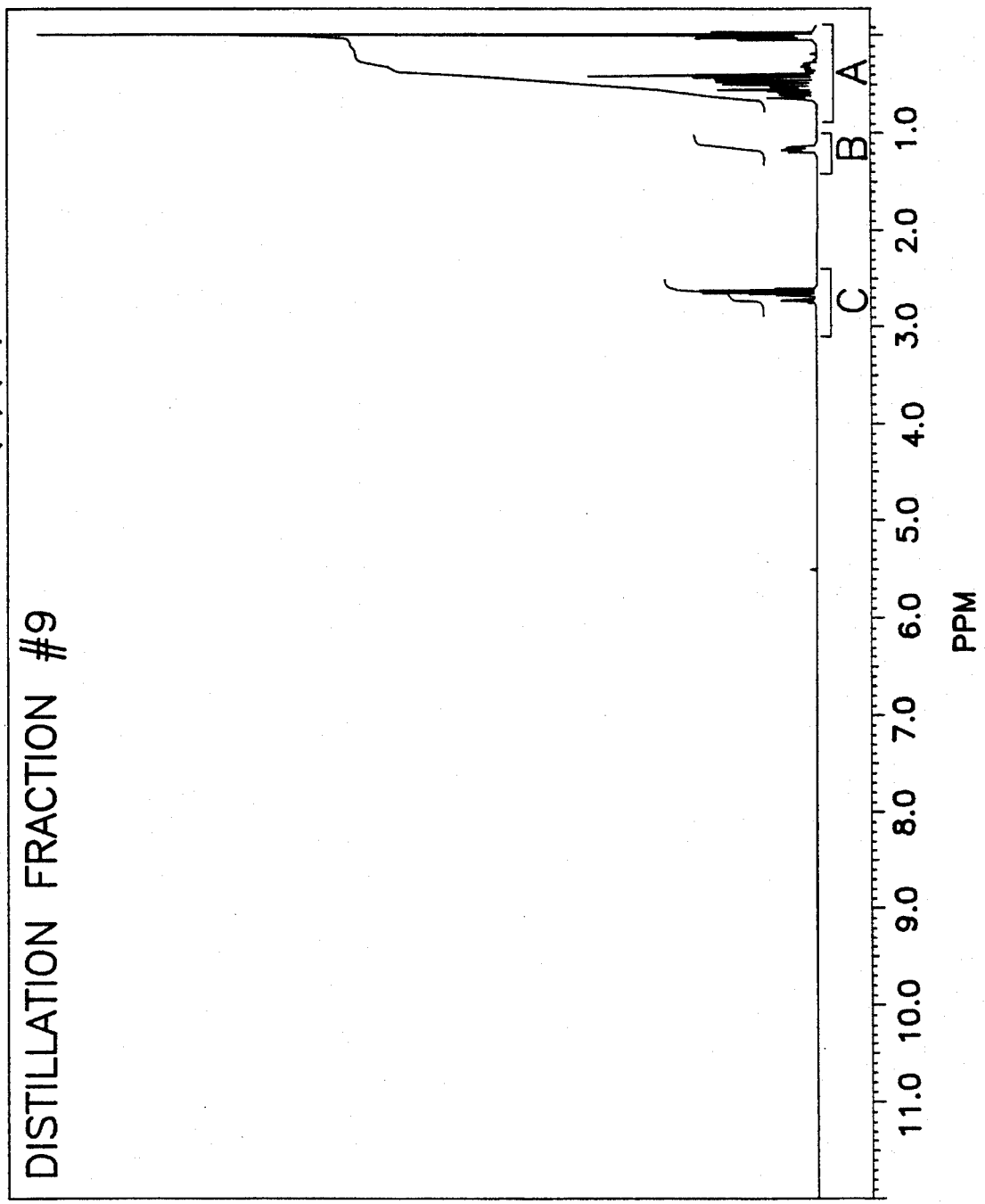

FIG. 8 is the NMR spectrum for distillation fraction 9 of the reaction product of Example II(A)(iv) containing 97% of the "cis" isomer having the structures:

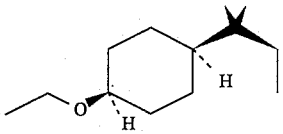

FIG. 8A is an enlargement of section "A" of the NMR spectrum of FIG. 8.

FIG. 8B is an enlargement of section "B" of the NMR spectrum of FIG. 8.

FIG. 8C is an enlargement of section "C" of the NMR spectrum of FIG. 8.

FIG. 9 is the capillary GC spectrum for distillation fraction 25 of the reaction product of Example II(A)(iv) containing 99% "trans" isomer having the structure:

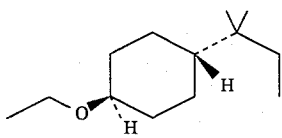

(conditions: 50 meter×0.32 mm nonbonded, fused silica carbowax 20M column programmed from 75° up to 225° C. at 2.0° C. per minute).

FIG. 10 is the NMR spectrum for distillation fraction 25 of the distillation of the reaction product of Example II(A)(iv) containing 99% "trans" isomer having the structure:

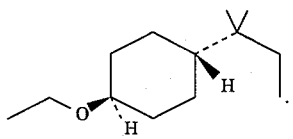

Figure 10A:
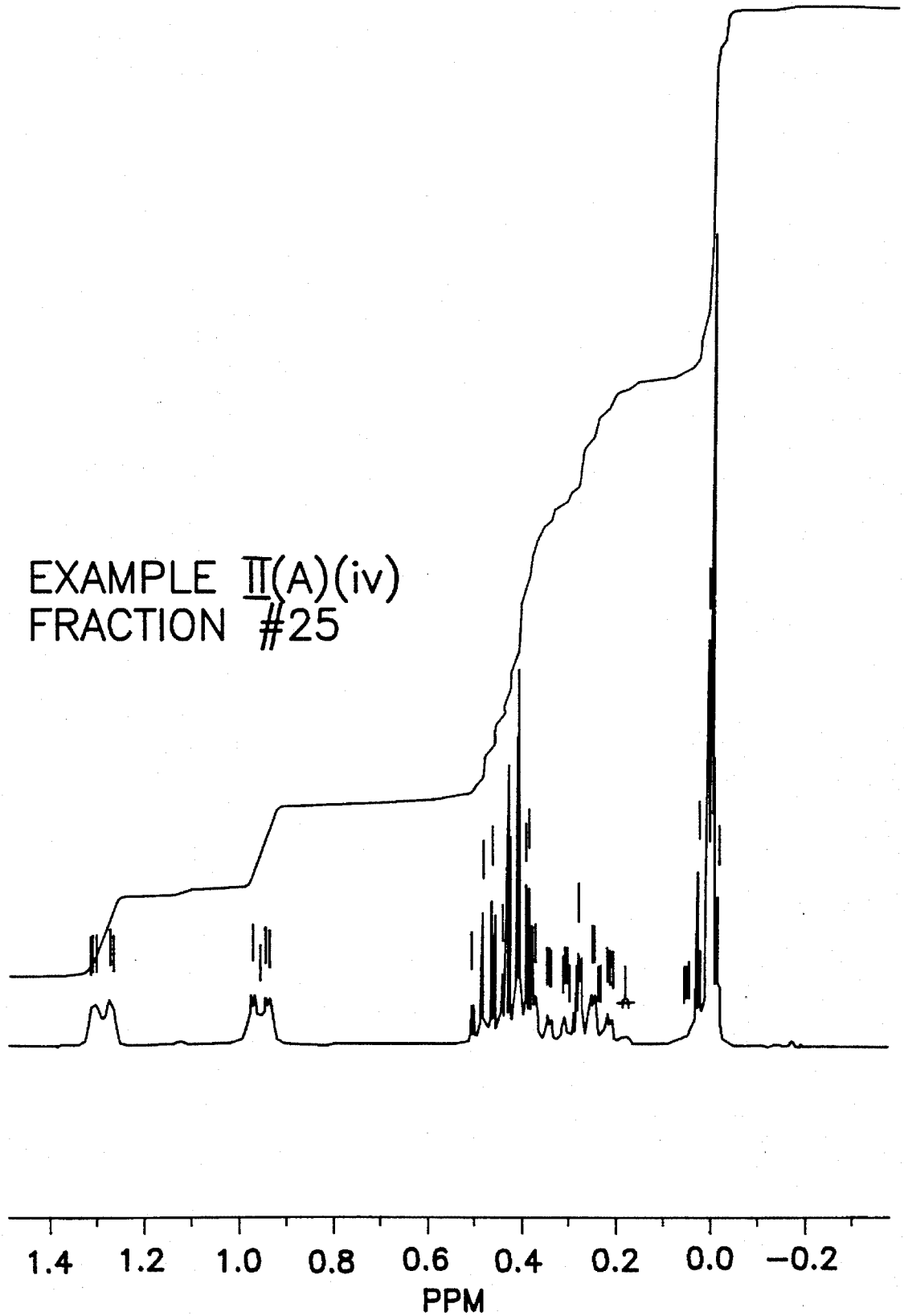

FIG. 10A is an enlargement of section "A" of the NMR spectrum of FIG. 10.

Figure 10B:
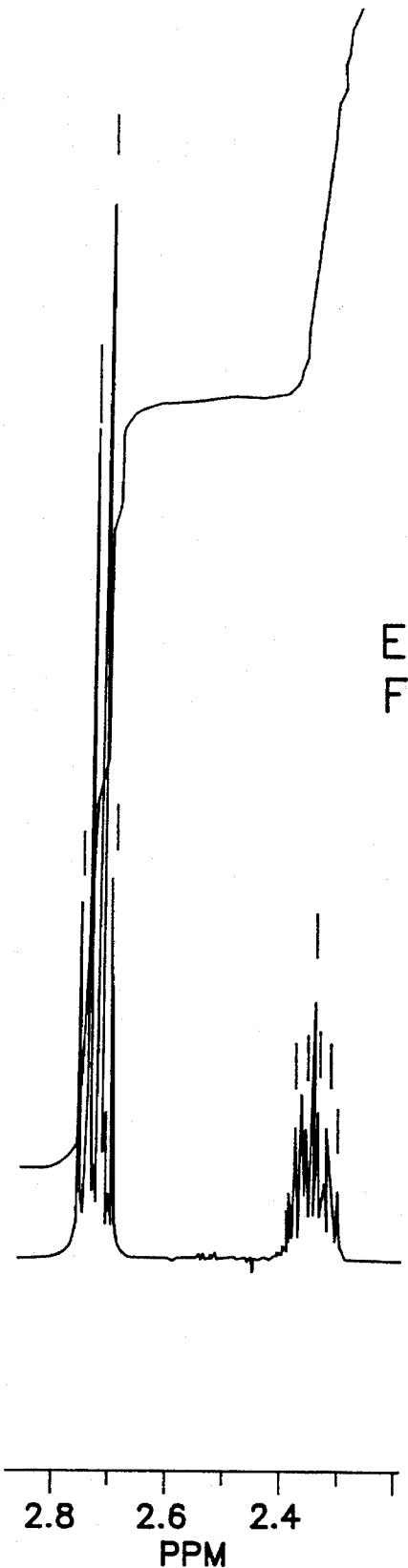

FIG. 10B is an enlargement of section "B" of the NMR spectrum of FIG. 10.

Figure 11:
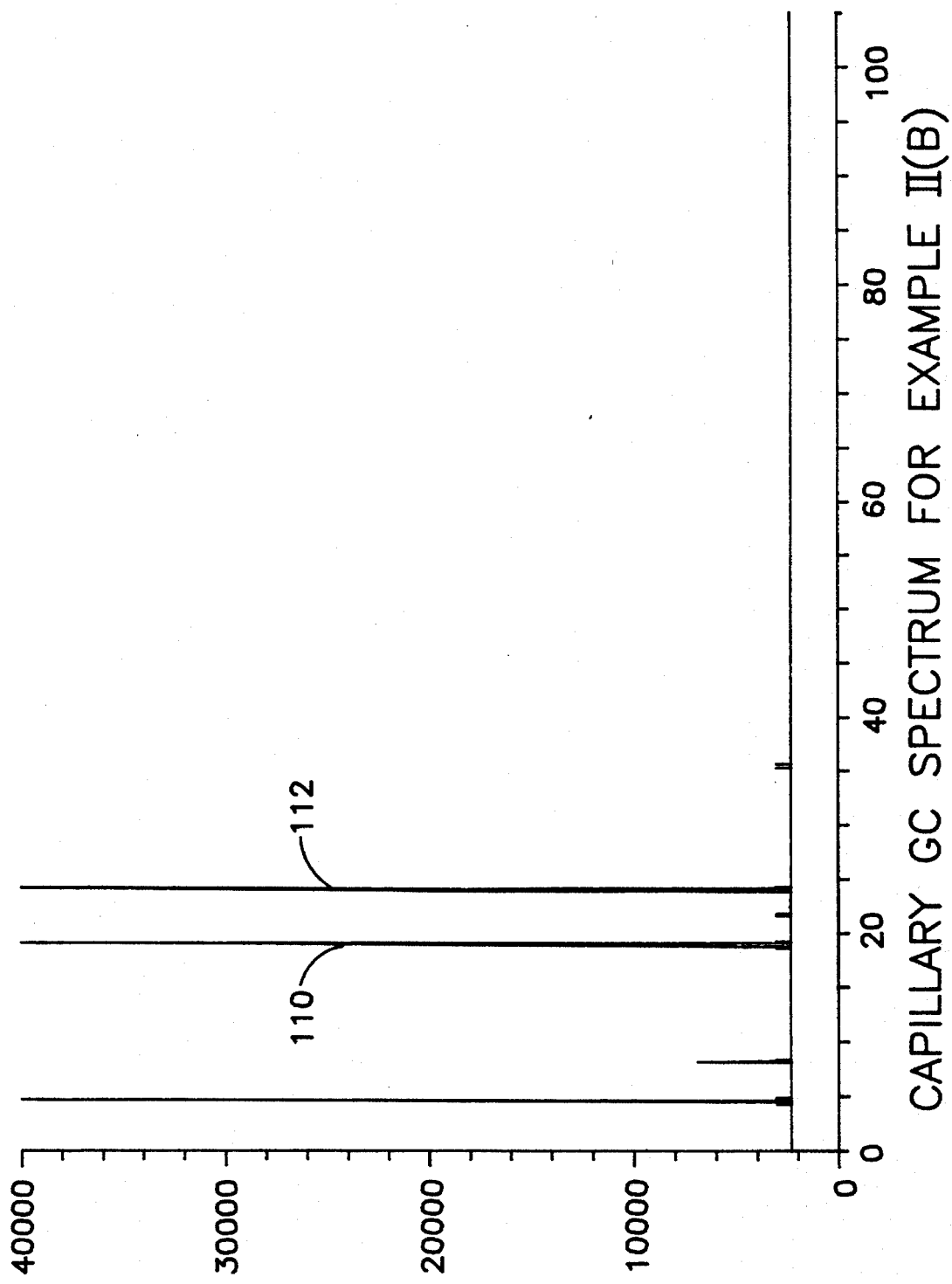

FIG. 11 is a capillary GC spectrum for the reaction product of Example II(B) containing a mixture of cis and trans isomers having the structures:

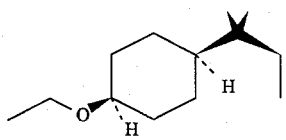

and

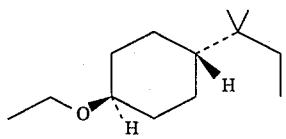

with the ratio of cis:trans isomer being 34:19 (conditions: meter×0.32 mm nonbonded, fused silica/carbowax 20M column programmed from 75° up to 225° C. at 2.0° C. per minute).

Figure 12:
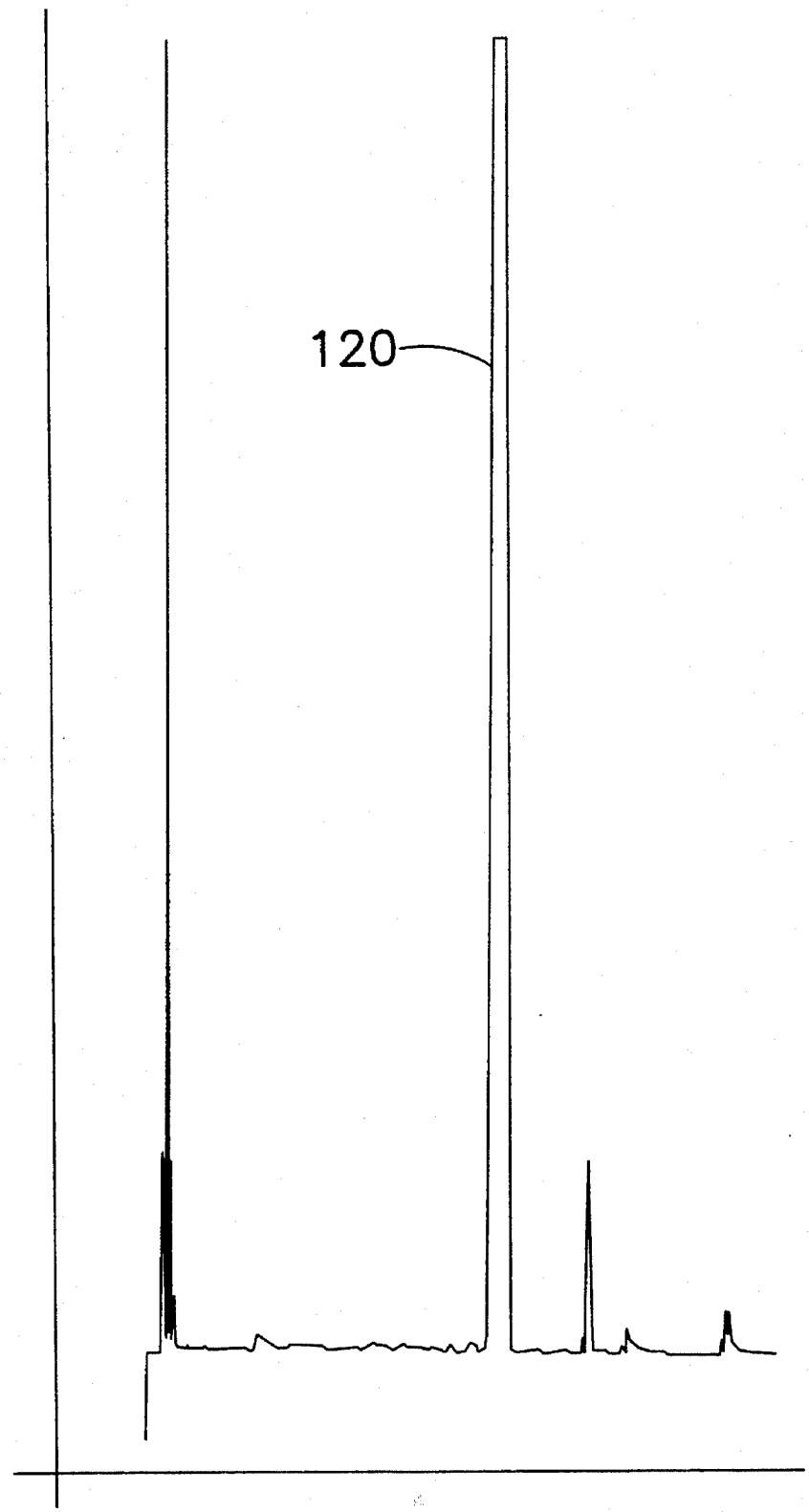

FIG. 12 is the GLC profile for the reaction product of Example III(A) containing the compound having the structure:

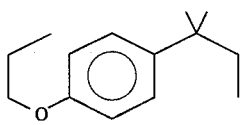

(conditions: SE-30 column programmed from 100° up to 220° C. at 8° C. per minute).

Figure 13:
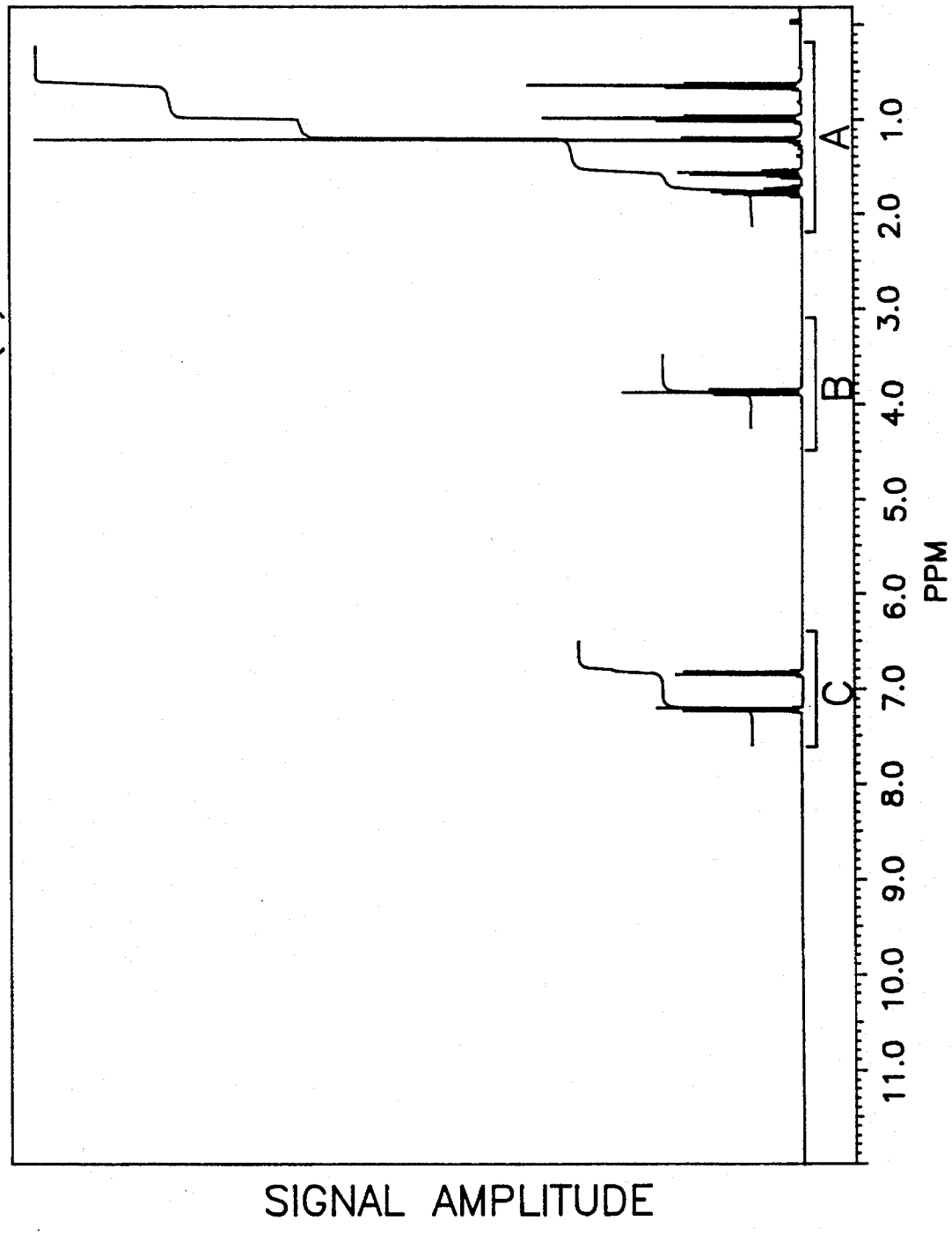

FIG. 13 is the NMR spectrum for the compound having the structure:

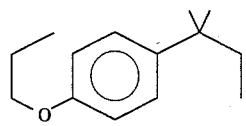

produced according to Example III(A).

Figure 13A:
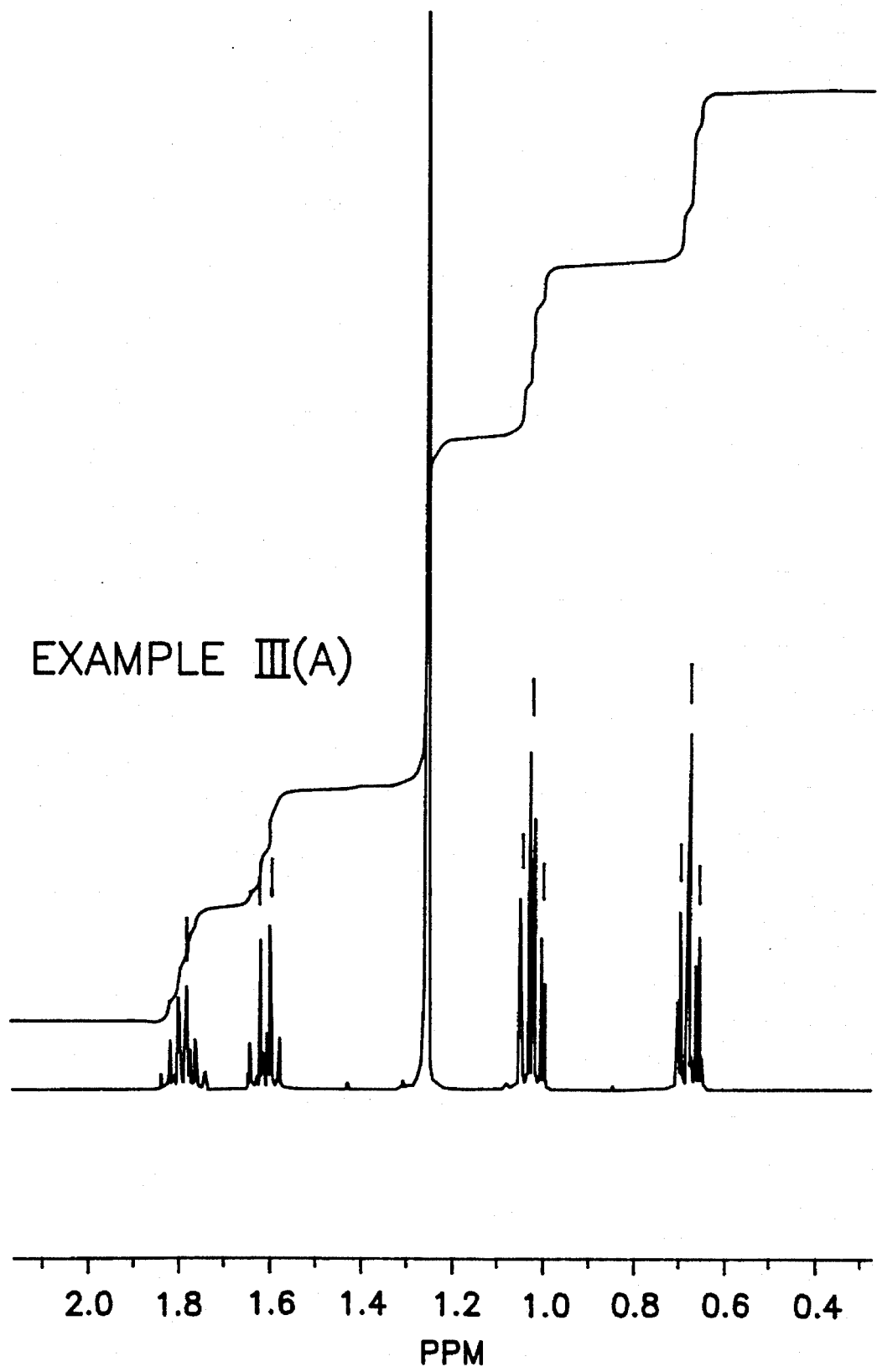

FIG. 13A is an enlargement of section "A" of the NMR spectrum of FIG. 13.

FIG. 13B is an enlargement of section "B" of the NMR spectrum of FIG. 13.

FIG. 13C is an enlargement of section "C" of the NMR spectrum of FIG. 13.

FIG. 14 is a capillary GC profile for the reaction product of Example III(B) containing the cis and trans isomers having the structures:

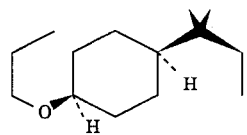

and

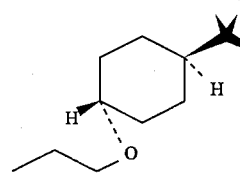

with the ratio of cis:trans isomer being 47:53 (conditions: meter×0.32 mm bonded, fused silica/methyl silicone column programmed from 75° C. up to 225° C. at 2.0° C. per minute).

FIG. 15 is the NMR spectrum for distillation fraction of the distillation of the reaction product of Example III(B) containing the compounds having the structures:

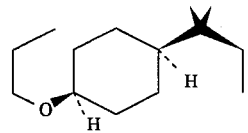

and

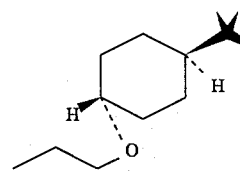

in a ratio of cis:trans isomer of 47:53.

Figure 15A:
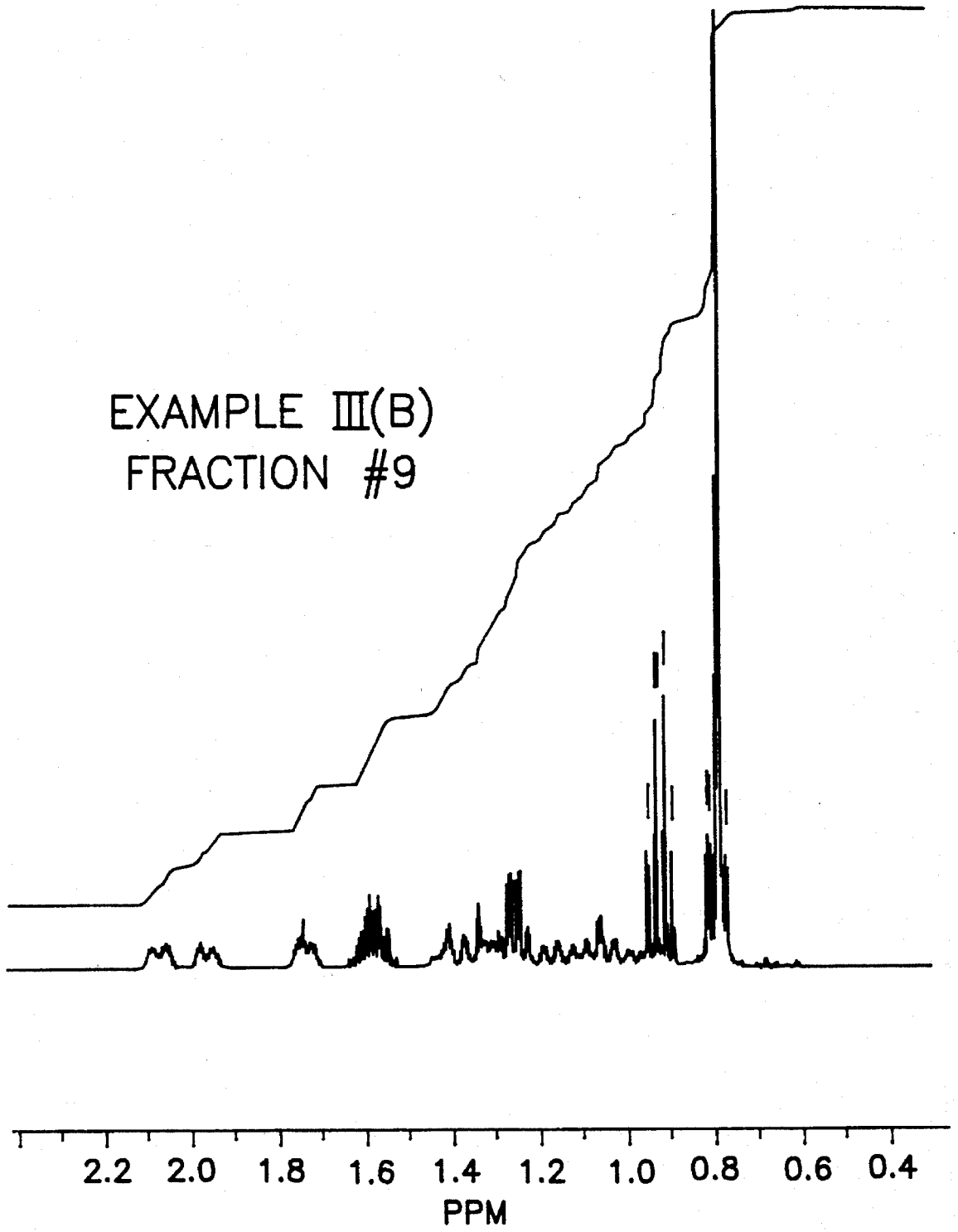

FIG. 15A is an enlargement of section "A" of the NMR spectrum of FIG. 15.

Figure 15B:
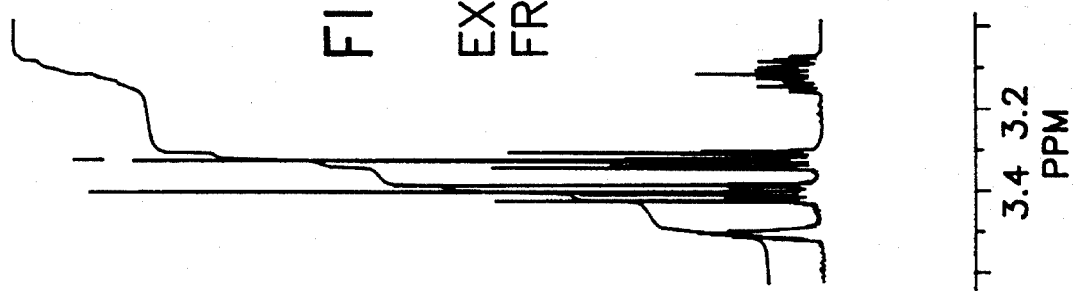

FIG. 15B is an enlargement of section "B" of the NMR spectrum of FIG. 15

Figure 15C:

FIG. 15C is an enlargement of section "C" of the NMR spectrum of FIG. 15.

FIG. 16 is a capillary GC profile for the reaction product of Example IV(A) containing the compound having the structure:

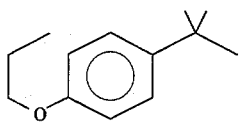

(conditions: 50 meter×0.32 mm bonded, fused silica/methyl silicone column programmed from 75° C. up to 225° C. at 2.0° C. per minute).

FIG. 17 is the NMR spectrum for the reaction product of Example IV(A) containing the compound having the structure:

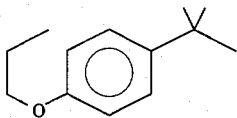

Figure 17A:
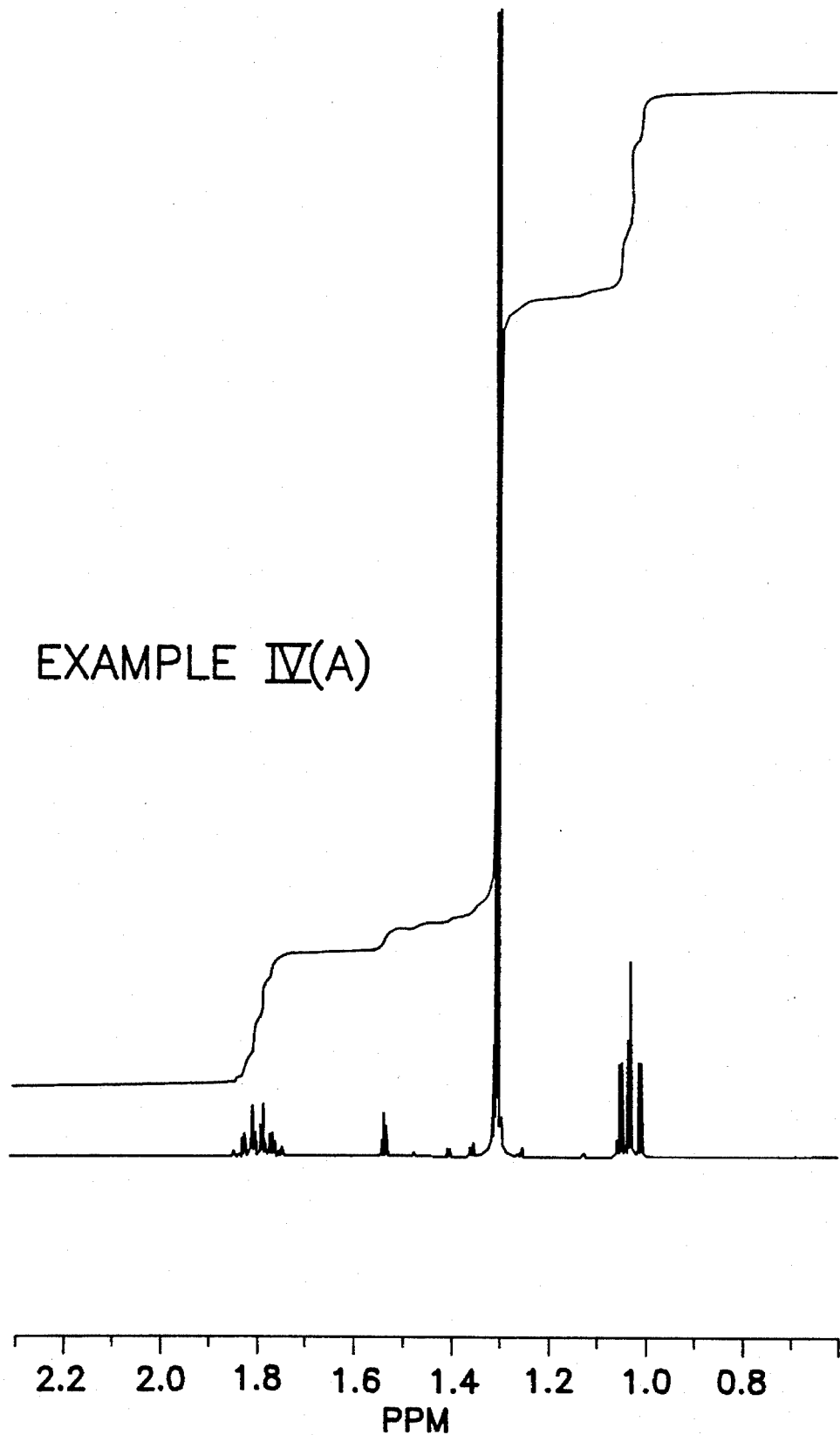

FIG. 17A is an enlargement of section "A" of the NMR spectrum of FIG. 17.

FIG. 17B is an enlargement of section "B" of the NMR spectrum of FIG. 17.

FIG. 17C is an enlargement of section "C" of the NMR spectrum of FIG. 17.

Figure 18:
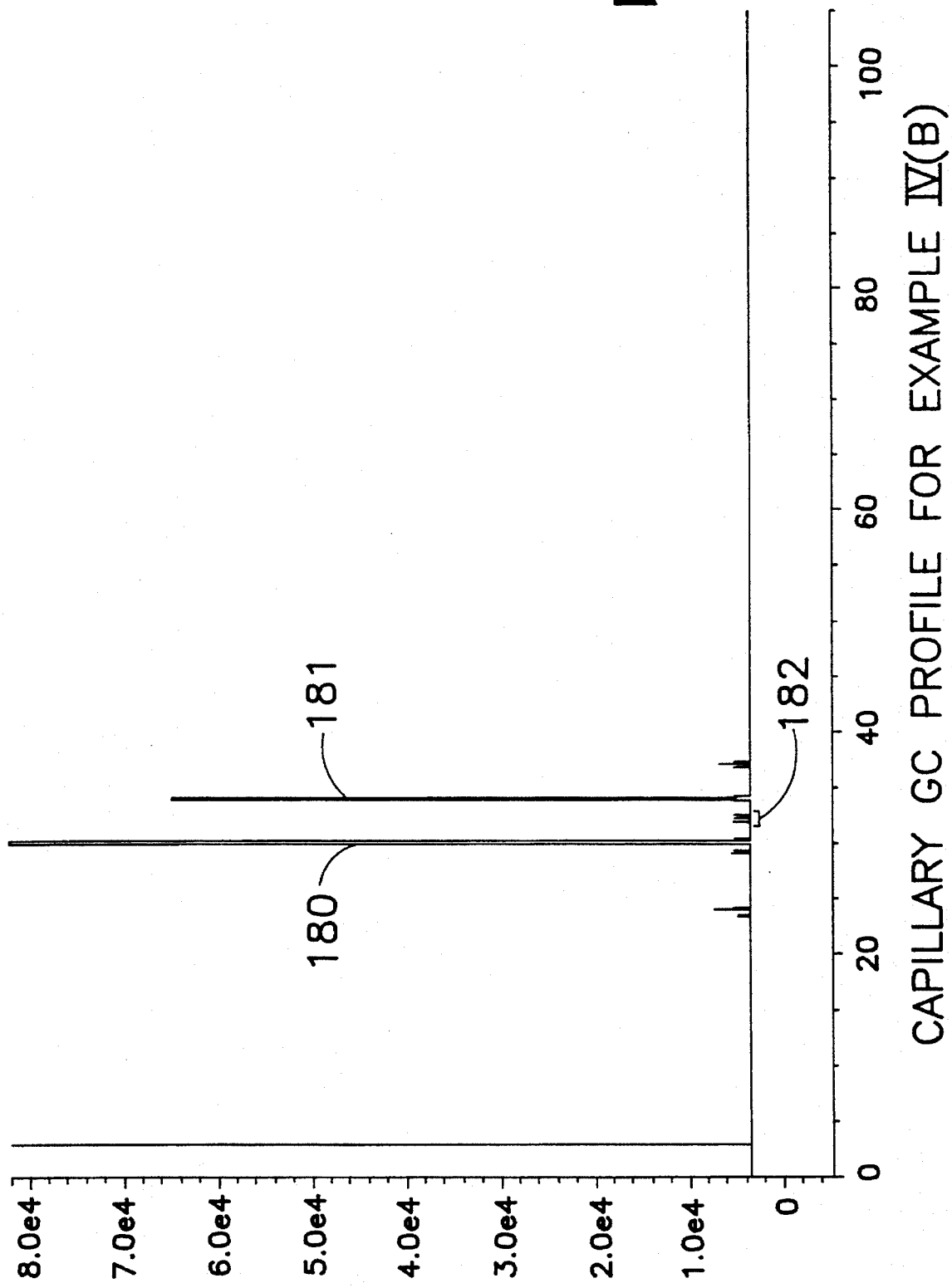

FIG. 18 is a capillary GC profile for the reaction product of Example IV(B) containing the compounds having the structures:

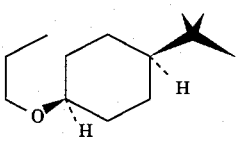

and

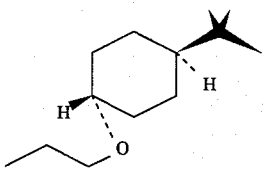

(cis:trans ratio of 63:12). (Conditions: 50 meter×0.32 mm bonded, fused silica/methyl silicone column programmed from 75° C. up to 225° C. at 2.0° C. per minute.)

FIG. 19 is the NMR spectrum for distillation fraction of the distillation of the reaction product of Example IV(B) containing the compounds having the structures:

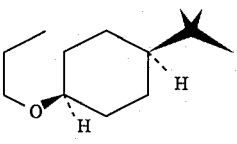

and

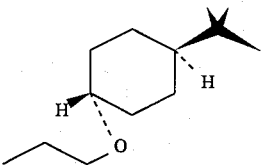

(cis:trans isomer ratio of about 64:12).

Figure 19A:
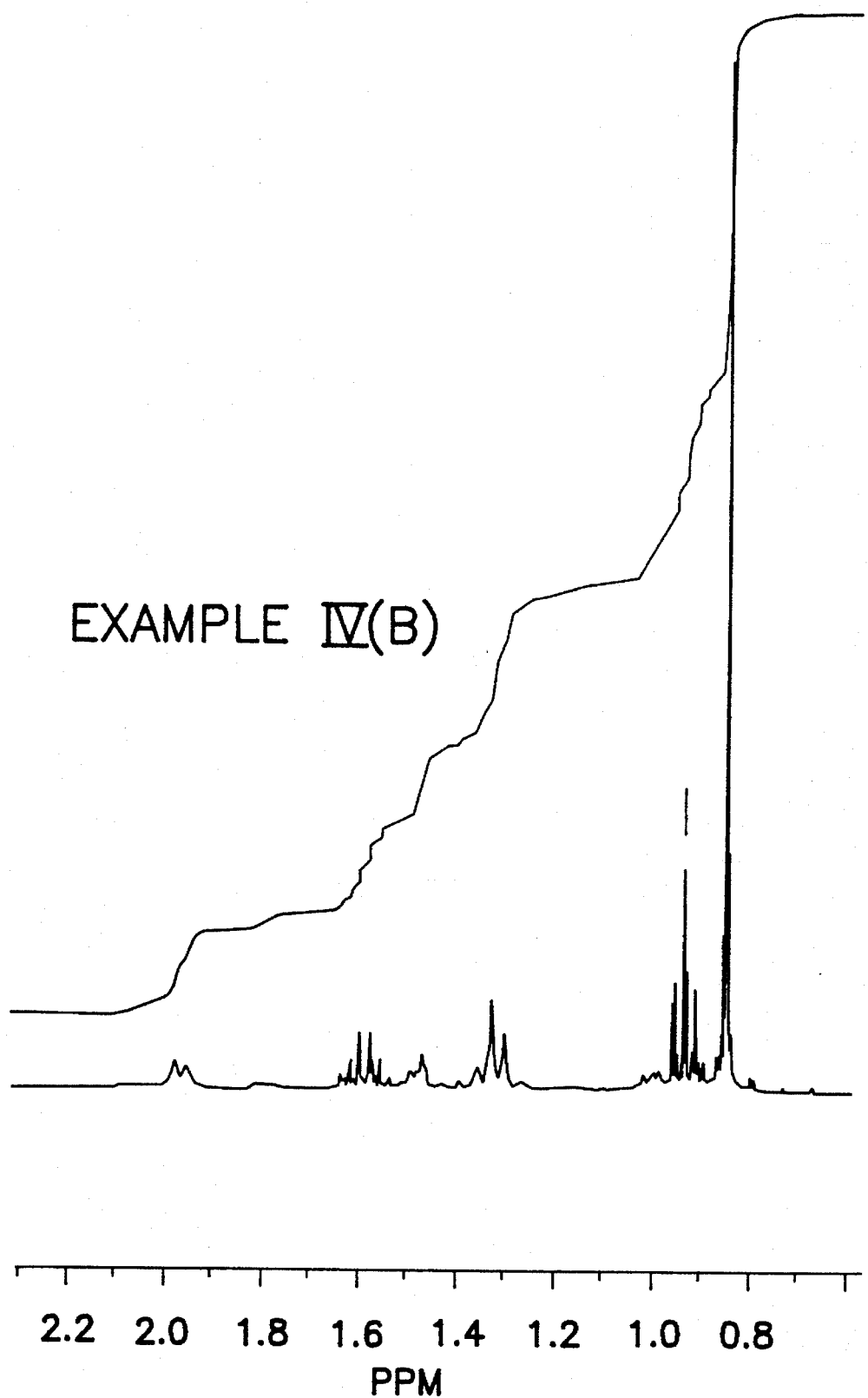

FIG. 19A is an enlargement of section "A" of the NMR spectrum of FIG. 19.

FIG. 19B is an enlargement of section "B" of the NMR spectrum of FIG. 19.

FIG. 19C is an enlargement of section "C" of the NMR spectrum of FIG. 19.

FIG. 20 is a capillary GC profile for the reaction product of Example V(A) containing the para and meta isomers having the structures:

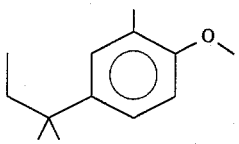

and

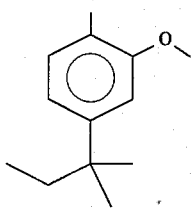

(ratio of para:meta isomers being 87:13) (conditions: 50 meter×0.32 mm bonded, fused silica/methyl silicone column programmed from 75° C. up to 225° C. at 2.0° C. per minute).

FIG. 21 is the NMR spectrum for the reaction product of Example V(A) containing the mixture of meta and para isomers having the structures:

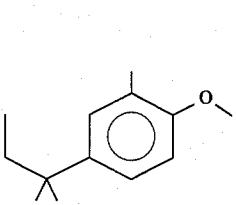 and 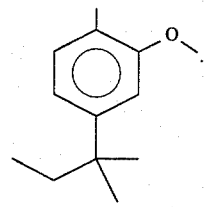

FIG. 21A is an enlargement of section "A" of the NMR spectrum of FIG. 21.

FIG. 21B is an enlargement of section "B" of the NMR spectrum of FIG. 21.

FIG. 21C is an enlargement of section "C" of the NMR spectrum of FIG. 21.

FIG. 22 is a capillary GC profile for the reaction product of Example V(B) containing a mixture of isomers of the compounds having the structures:

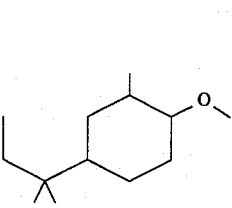 and 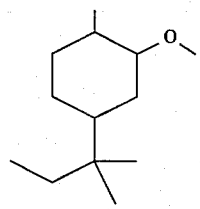

including the isomer having the structure:

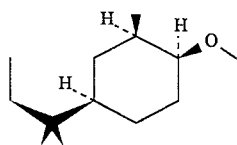

(conditions: 50 meter×0.32 mm bonded, fused silica/methyl silicone column programmed from 75° C. up to 225° C. at 2.0° C. per minute).

FIG. 23 is the NMR spectrum for distillation fraction 11 of the distillation of the reaction product of Example V(B) containing a mixture of isomers of the compounds having the structures:

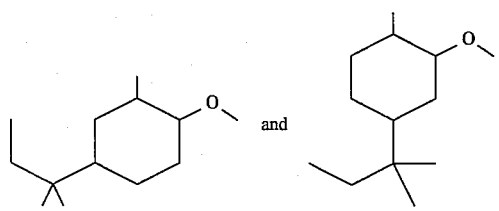

including the compound having the structure:

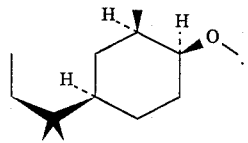

FIG. 23A is an enlargement of section "A" of the NMR spectrum of FIG. 23.

FIG. 23B is an enlargement of section "B" of the NMR spectrum of FIG. 23.

FIG. 24 is a capillary GC profile for the reaction product of Example VI(A) containing a mixture of para and meta isomers having the structures:

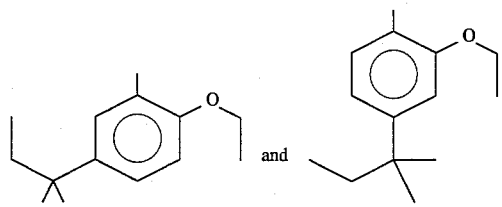

with the ratio of para:meta isomer being 92:8 (conditions: 50 meter×0.32 mm bonded, fused silica/methyl silicone (OV1) column programmed from 75° C. up to 225° C. at 2.0° C. per minute).

Figure 25:
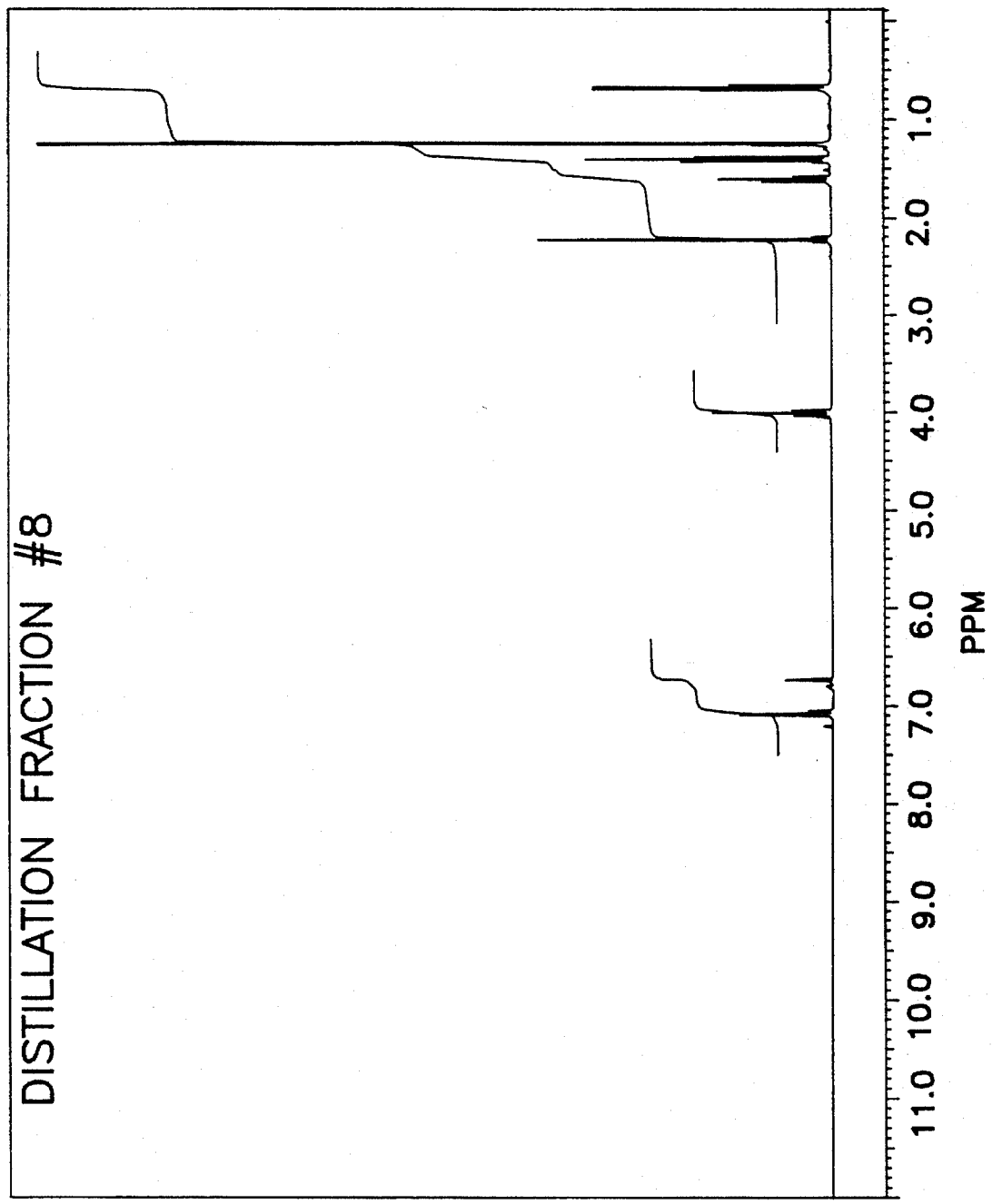

FIG. 25 is the NMR spectrum for distillation fraction 8 of the distillation of the reaction product of Example VI(A) containing a mixture of isomers having the structures:

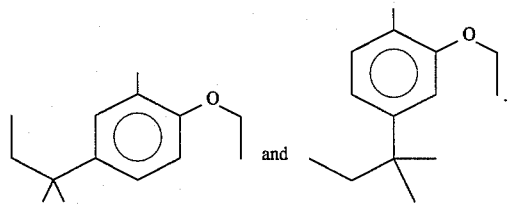

Figure 26:
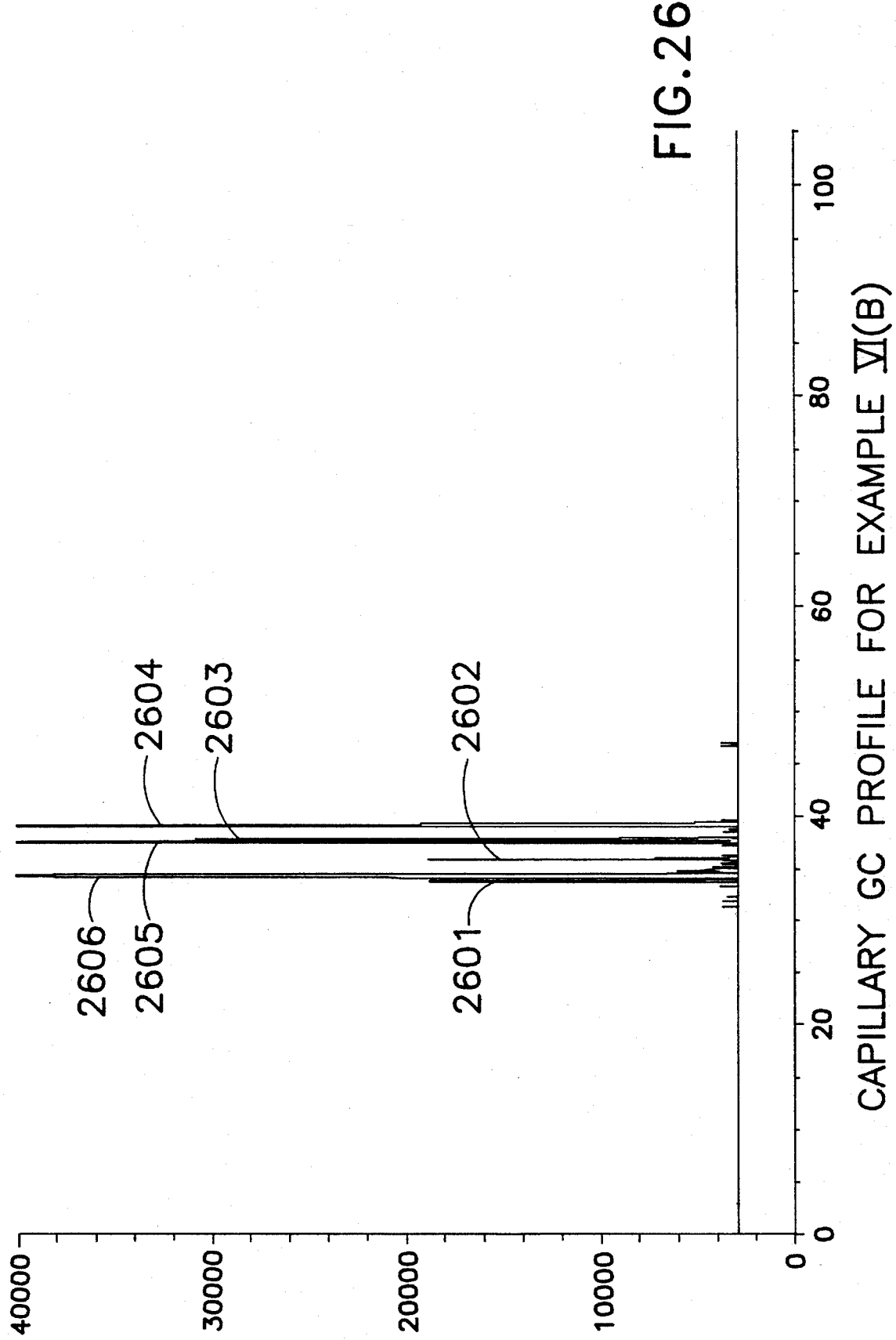

FIG. 26 is a capillary GC profile for the reaction product of Example VI(B) containing a mixture of isomers having the structures:

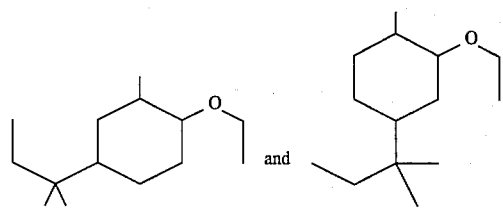

including the isomer having the structure:

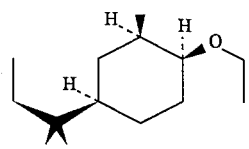

with the ratio of para: meta isomers being about 92:8, respectively (conditions: 50 meter×0.32 mm bonded, fused silica/methyl silicone (OV1) column programmed from 75° C. up to 225° C. at 2.0° C. per minute).

Figure 27:
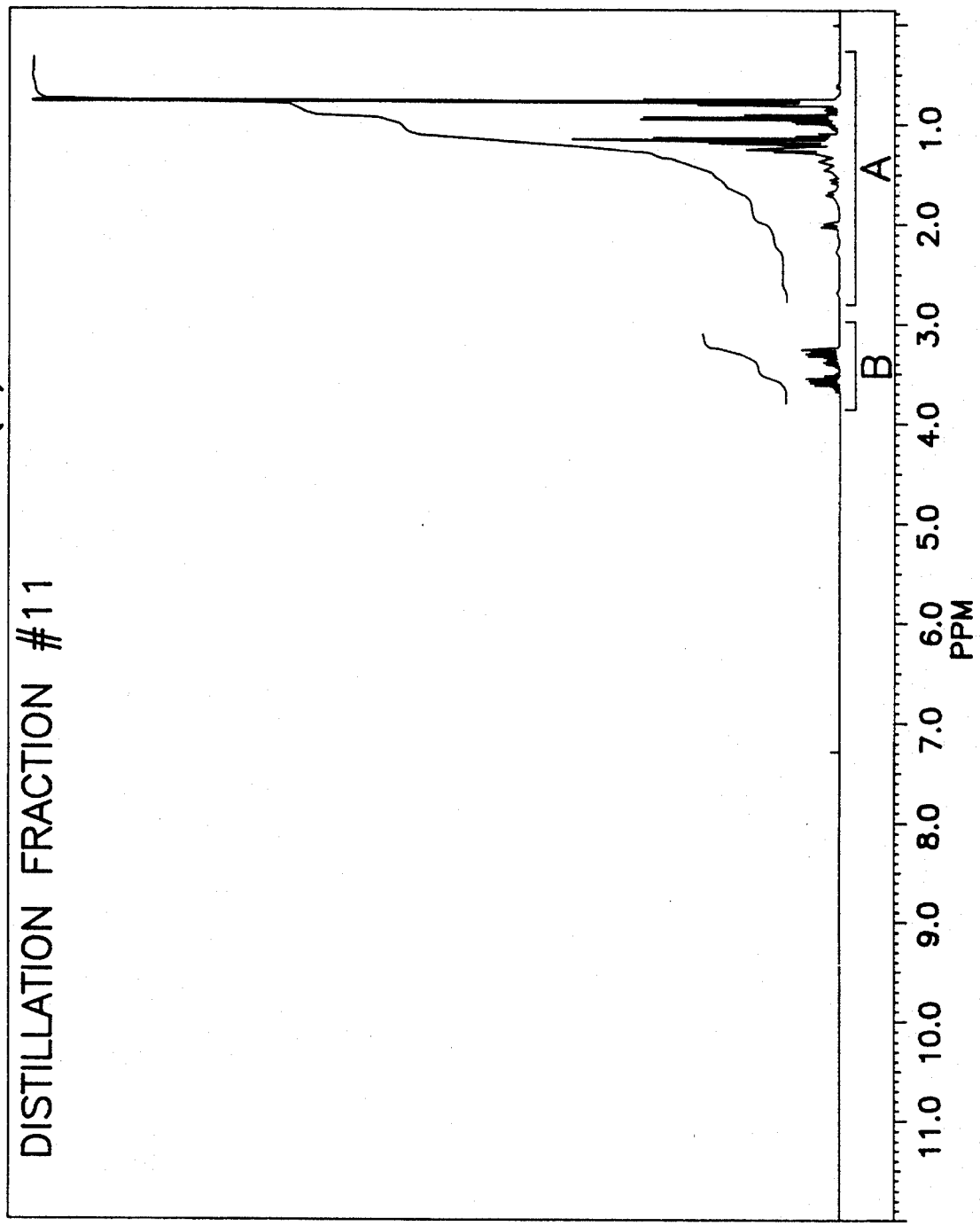

FIG. 27 is the NMR spectrum for distillation fraction 11 of the distillation of the reaction product of Example VI(B) containing a mixture of isomers having the structures:

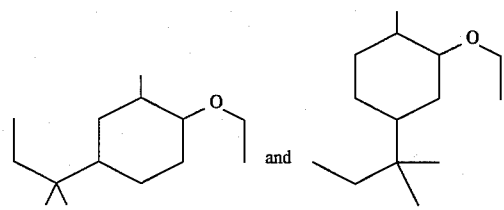

including the isomer having the structure:

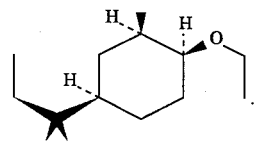

Figure 27A:
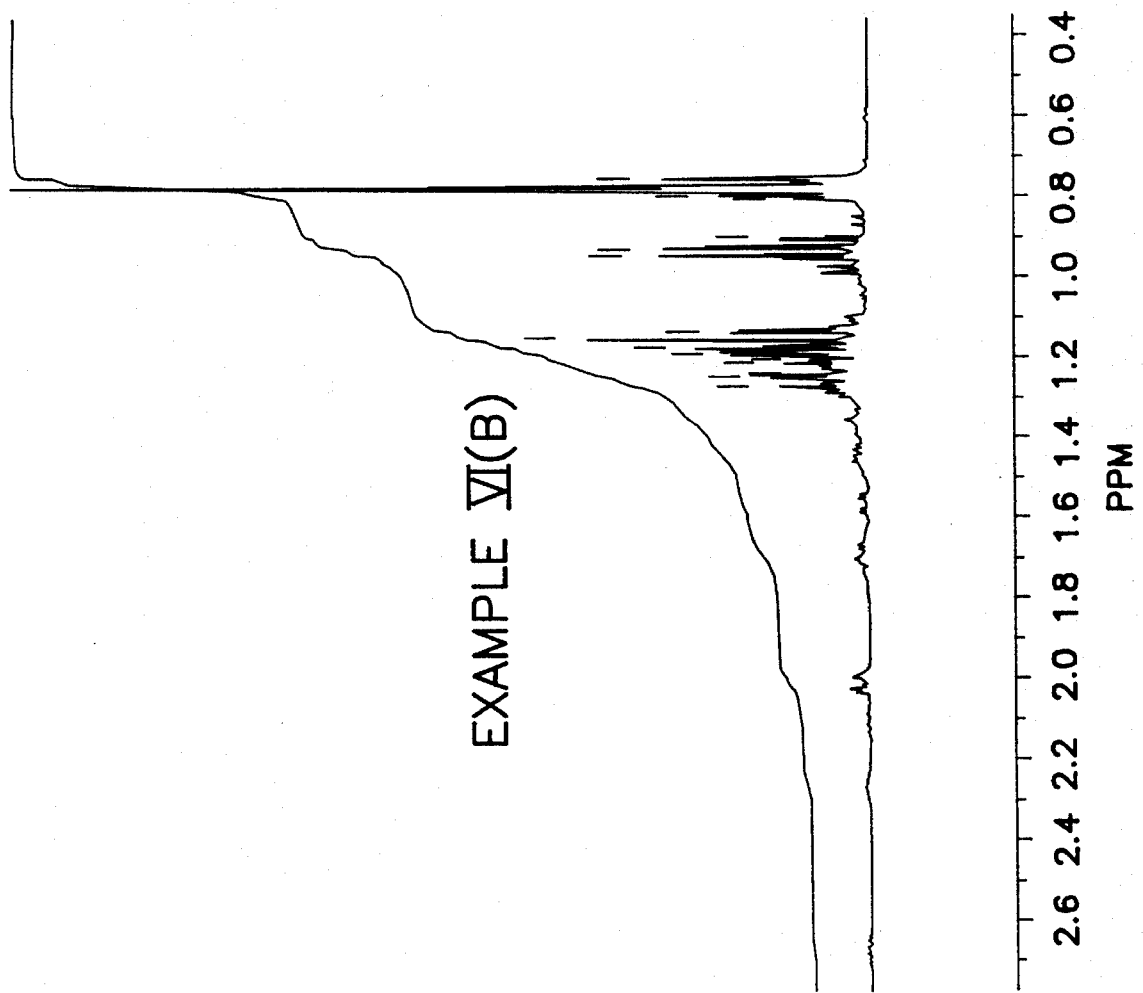

FIG. 27A is an enlargement of section "A" of the NMR spectrum of FIG. 27.

Figure 27B:
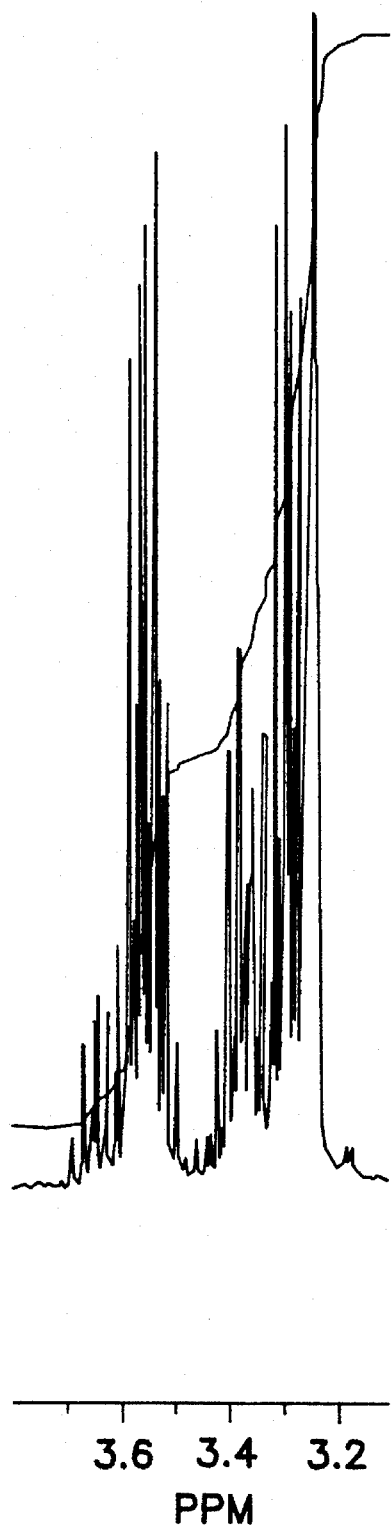

FIG. 27B is an enlargement of section "B" of the NMR spectrum of FIG. 27.

Figure 28:
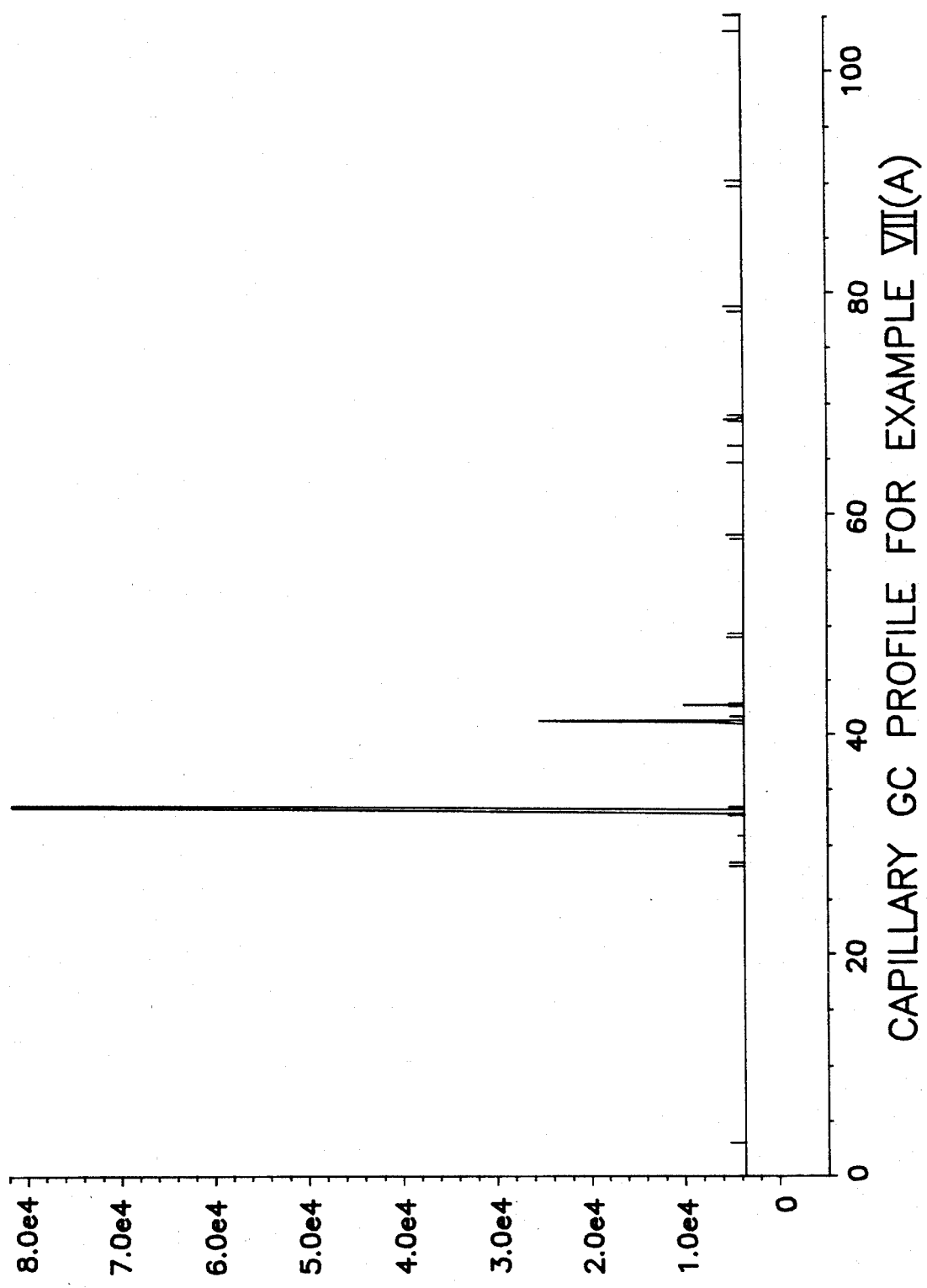

FIG. 28 is a capillary GC profile for the reaction product of Example VII(A) containing the compound having the structure:

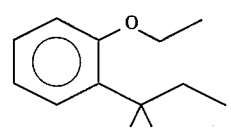

(conditions: 50 meter×0.322 mm bonded, fused silica/methyl silicone (OV1) column programmed from 75° C. up to 225° C. at 2.0° C. per minute).

FIG. 29 is the NMR spectrum for the reaction product of Example VII(A) containing the compound having the structure:

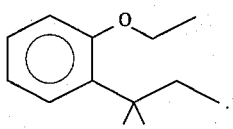

Figure 29A:
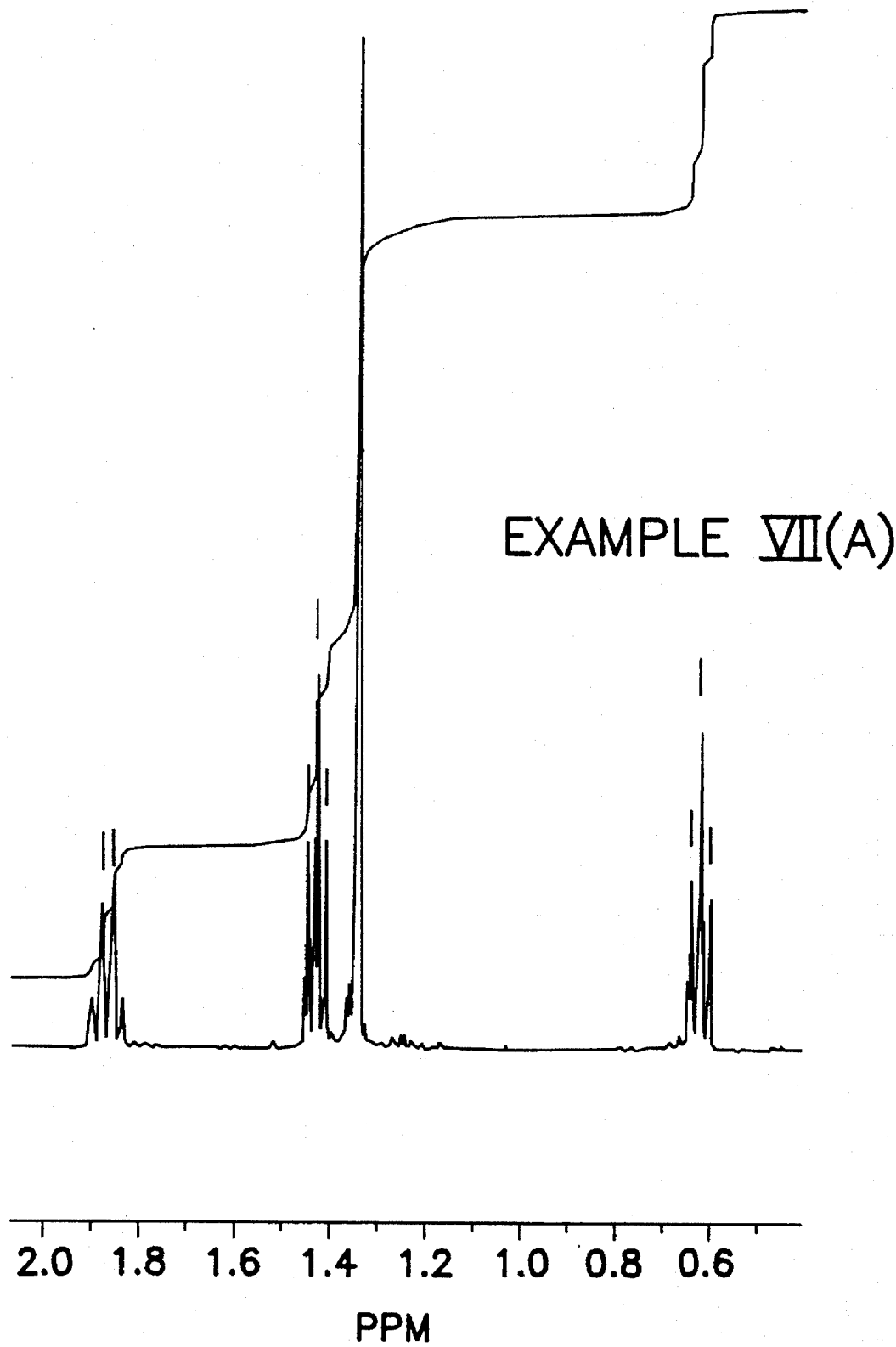

FIG. 29A is an enlargement of section "A" of the NMR spectrum of FIG. 29.

FIG. 29B is an enlargement of section "B" of the NMR spectrum of FIG. 29.

FIG. 29C is an enlargement of section "C" of the NMR spectrum of FIG. 29.

Figure 30:
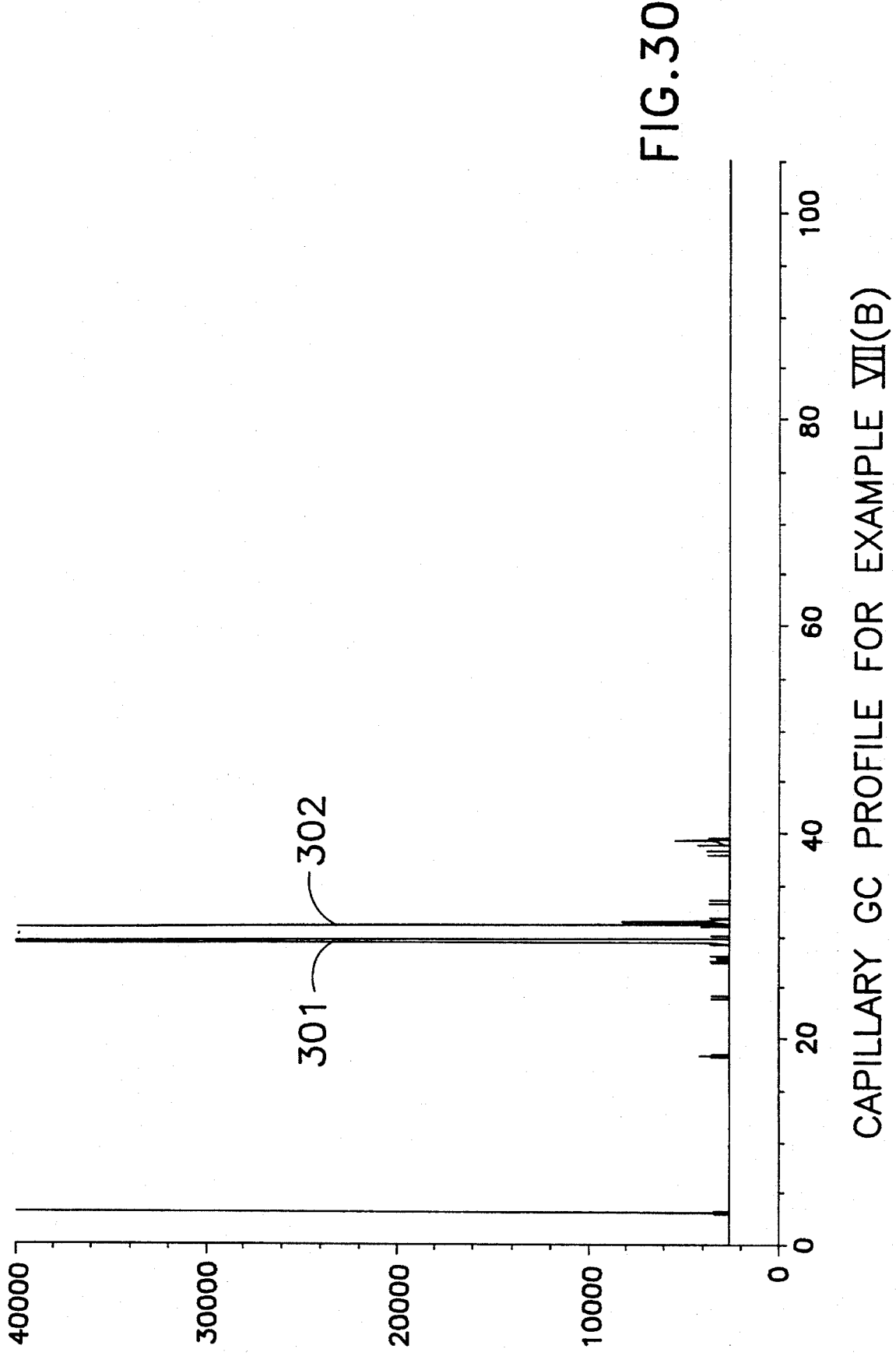

FIG. 30 is a capillary GC profile for the reaction product of Example VII(B) containing a mixture of cis and trans isomers having the structures:

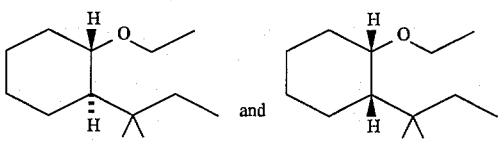

with the ratio of cis:trans isomers being 90:10 (conditions: meter×0.32 mm bonded, fused silica/methyl silicone (OV1) column programmed from 75° C. up to 225° C. at 2.0° C. per minute).

Figure 31:
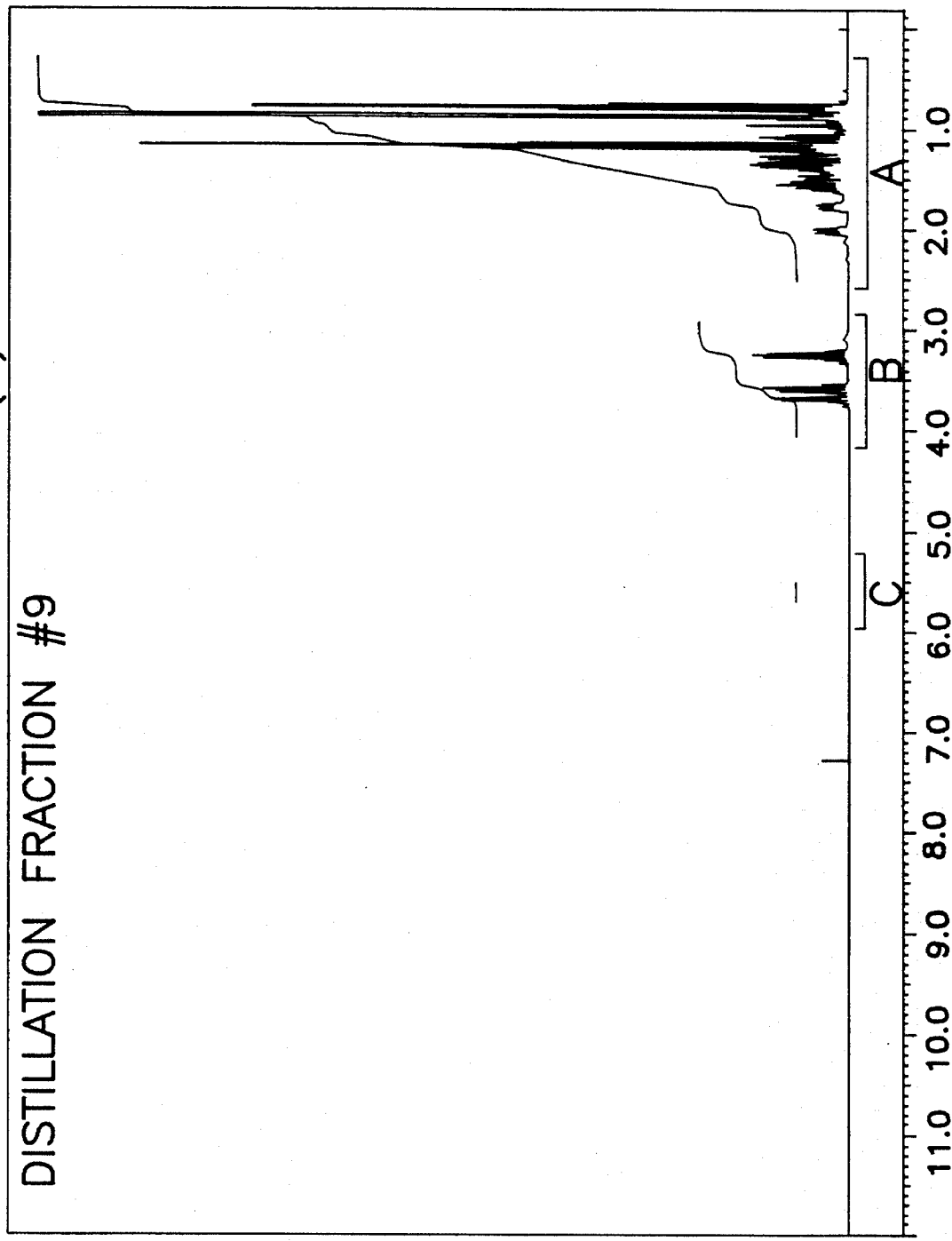

FIG. 31 is the NMR spectrum for distillation fraction 9 of the distillation of the reaction product of Example VII(B) containing the compounds having the structures:

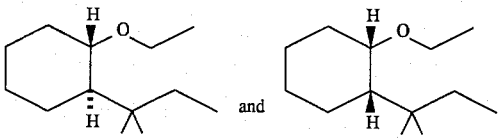

Figure 31A:
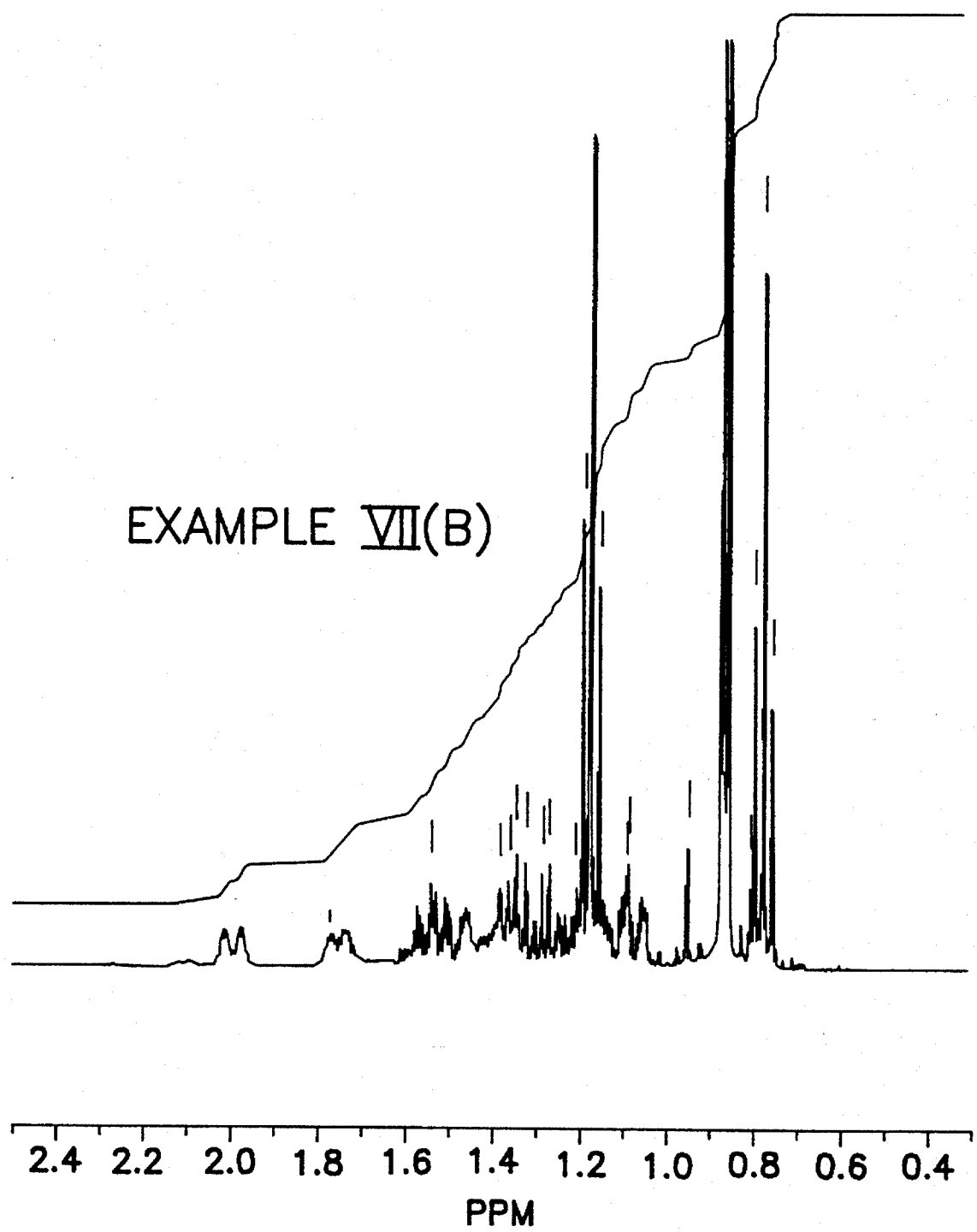

FIG. 31A is an enlargement of section "A" of the NMR spectrum of FIG. 31.

FIG. 31B is an enlargement of section "B" of the NMR spectrum of FIG. 31.

FIG. 31C is an enlargement of section "C" of the NMR spectrum of FIG. 31.

Figure 32:
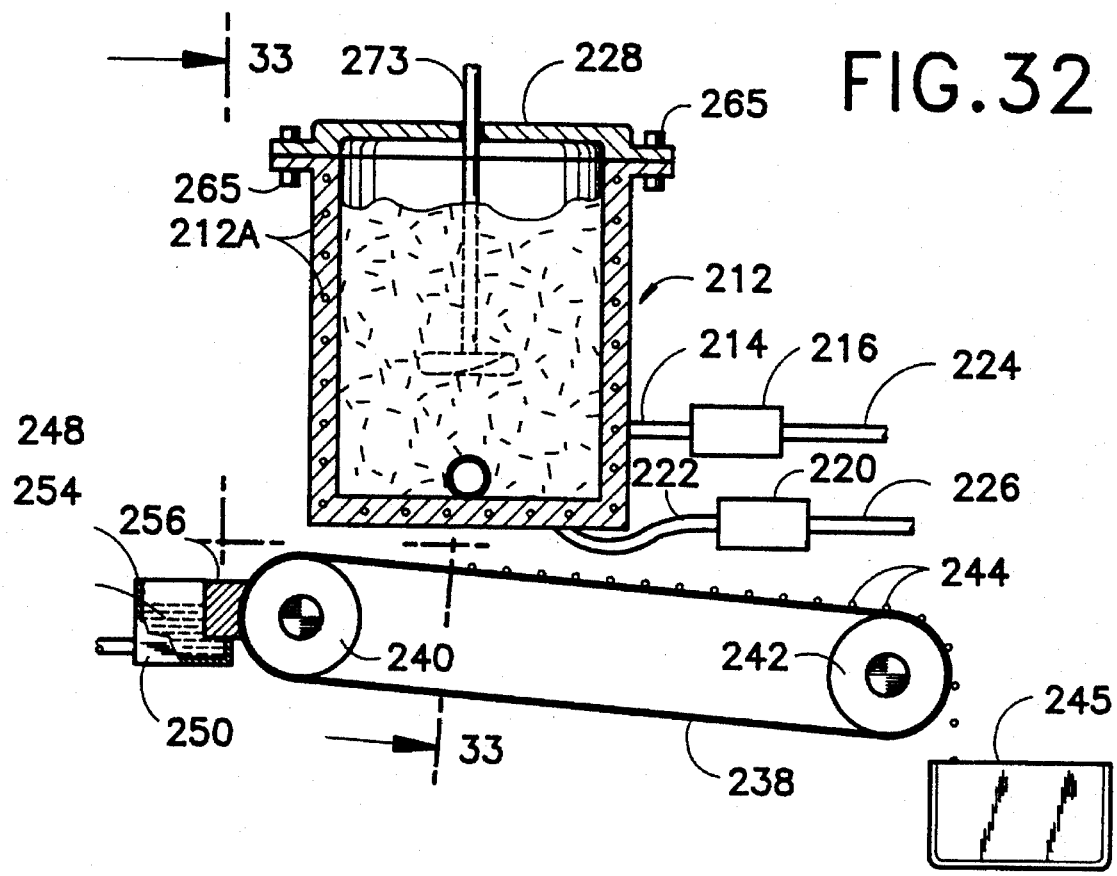

FIG. 32 is a partial side elevation view and partial sectional view of an apparatus for forming polymer pellets containing at least one of the alkyl-substituted-$C_1$–$C_3$ alkoxy-$C_6$-cycloaliphatic compounds of our invention.

Figure 33:
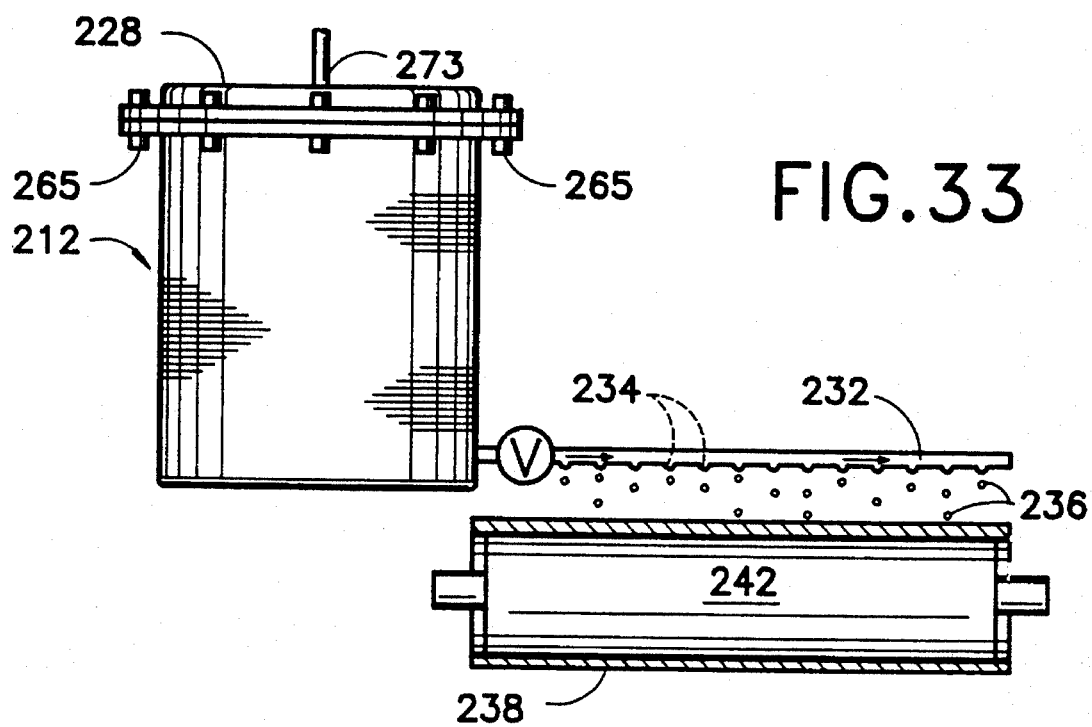

FIG. 33 is a section taken along the line 33—33 of FIG. 32.

DETAILED DESCRIPTION OF THE DRAWINGS

FIG. 1 is the capillary GC profile for the reaction product of Example I(A). The peak indicated by reference numeral 10 is the peak for the compound having the structure:

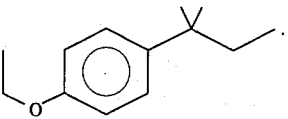

FIG. 2 is the capillary GC profile for the reaction product of Example I(B). The peaks indicated by reference numerals 11 and 12 are the peaks for the cis and trans isomers of the compound having the structure:

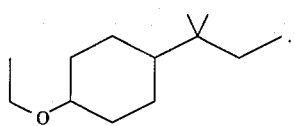

Peak 11 is for the cis isomer having the structure:

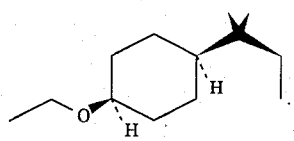

Peak 12 is for the trans isomer having the structure:

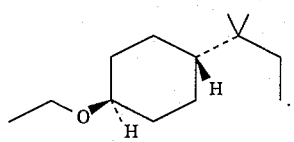

The peak indicated by reference numeral 13 is the peak for the compound having the structure:

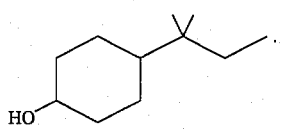

The peak indicated by reference numeral 14 is the peak for the compound having the structure:

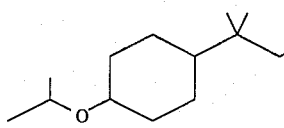

FIG. 5A is a capillary GC spectrum for the reaction product of Example II(A)(i) containing in the ratio of 48:52 the cis and trans isomers:

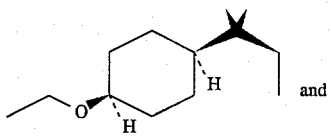

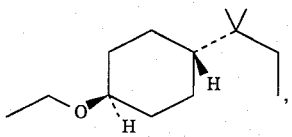

respectively (conditions: 50 meter×0.32 mm bonded, fused silica/methyl silicone (OV1) column programmed from 75° C. up to 225° C. at 2.0° C. per minute).

The peak indicated by reference numeral 50 is the peak for the cis isomer having the structure:

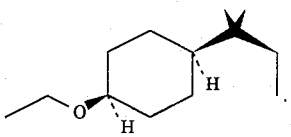

The peak indicated by reference numeral 52 is for the trans isomer having the structure:

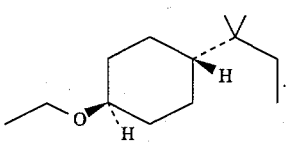

The peak indicated by reference numeral 54 is for the hydrocarbon having the structure:

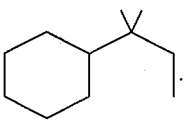

FIG. 5B is a capillary GC spectrum for the reaction product of Example II(A)(ii) with the cis:trans Isomer ratio being 48:52 for the compounds having the structures:

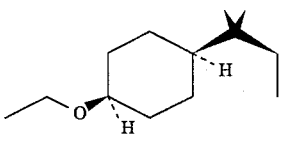

and

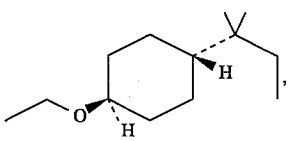

respectively.

The peak indicated by reference numeral 56 is for the cis isomer having the structure:

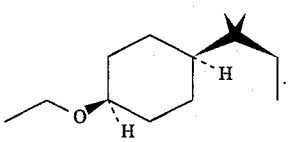

The peak indicated by reference numeral 57 is for the trans isomer having the structure:

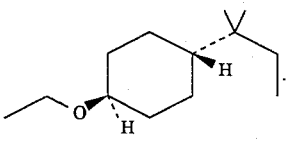

The peak indicated by reference numeral 58 is for the hydrocarbon having the structure:

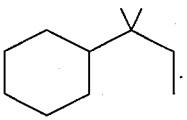

FIG. 11 is a capillary GC spectrum for the reaction product of Example II(B) containing the cis and trans isomers having the structures:

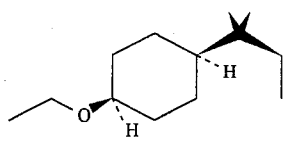

and

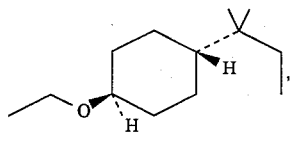

respectively, in the ratio of 34 parts cis isomer:19 parts trans isomer. The peak indicated by reference numeral 110 is for the cis isomer having the structure:

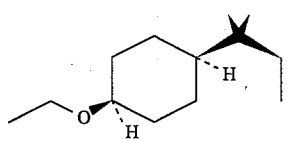

The peak indicated by reference numeral 112 is for the trans isomer having the structure:

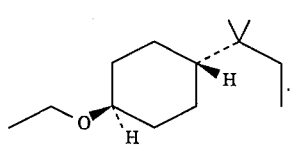

FIG. 12 is a GLC profile for the reaction product of Example III(A). The peak indicated by reference numeral 120 is for the compound having the structure:

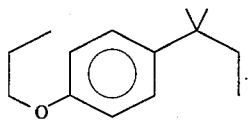

FIG. 14 is the capillary GC profile for the reaction product of Example III(B) containing a mixture of cis and trans isomers having the structures:

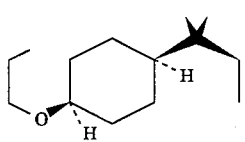

and

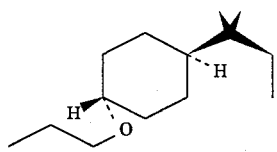

with the ratio of cis:trans isomer being 47:53. The peak indicated by reference numeral 140 is for the cis isomer having the structure:

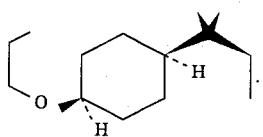

The peak indicated by reference numeral 142 is for the trans isomer having the structure:

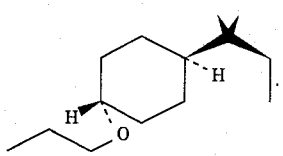

The peak indicated by reference numeral 144 is for the hydrocarbon having the structure:

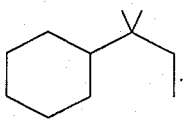

FIG. 18 is the capillary GC profile for the reaction product of Example IV(B). The peak indicated by reference numeral 180 is for the cis isomer having the structure:

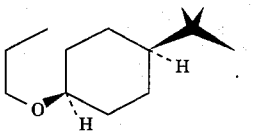

The peak indicated by reference numeral 181 is for the trans isomer having the structure:

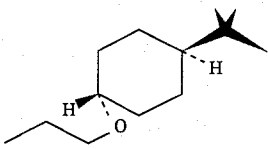

The peaks indicated by reference numeral 182 is for the isomers of the alcohol having the structure:

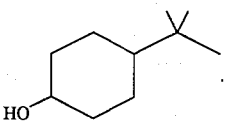

FIG. 20 is the capillary GC profile for the reaction product of Example V(A) containing a mixture of para and meta isomers having the structures:

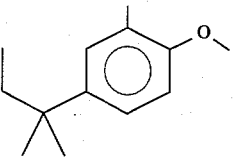

and

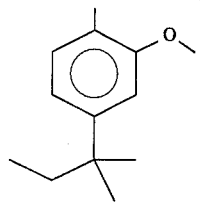

with the ratio of para: meta isomer being 87:13. The peak indicated by reference numeral 200 is the peak for the para isomer having the structure:

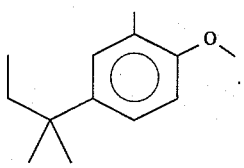

The peak indicated by reference numeral 19 is for the meta isomer having the structure:

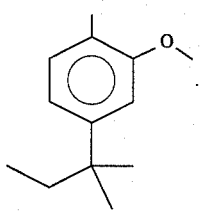

FIG. 22 is the capillary GC profile for the reaction product of Example V(B) containing a mixture of para and meta isomers in the ratio of para:meta isomers of 87:13. The peaks indicated by reference numerals 2206, 2207 and 2205 are for the para isomer having the structure:

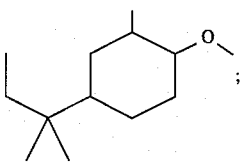

and one of the peaks is for the isomer having the structure:

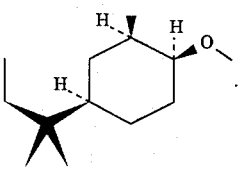

The peaks indicated by reference numerals 2200, 2201, 2202 and 2203 are for the meta isomer having the structure:

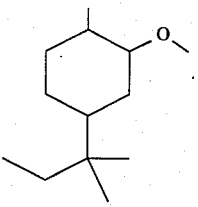

FIG. 24 is the capillary GC profile for the reaction product of Example VI(A) containing a mixture of para and meta isomers having the structures:

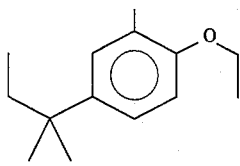

and

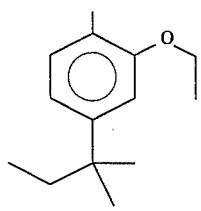

with the ratio of para:meta isomer being 92:8. The peak indicated by reference numeral 2400 is for the meta isomer having the structure:

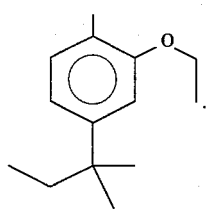

The peak indicated by reference numeral 2401 is for the para isomer having the structure:

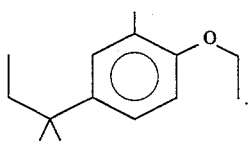

FIG. 26 is the capillary GC profile for the reaction product of Example VI(B) containing a mixture of para and meta isomers having the structures:

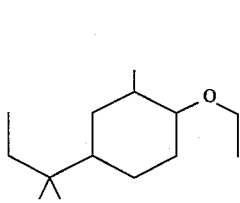 and 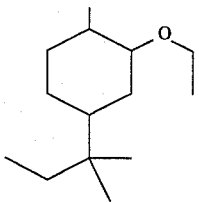

including the isomer having the structure:

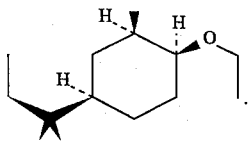

The ratio of para:meta isomer is 92:8 The peaks indicated by reference numeral 2601, 2602 and 2603 are for the meta isomer having the structure:

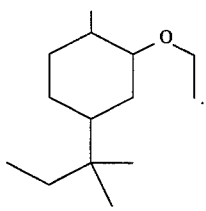

The peaks indicated by reference numerals 2604, 2605 and 2606 are for the para isomer having the structure:

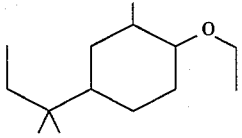

including the compound having the structure:

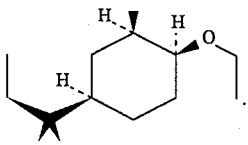

FIG. 30 is the capillary GC profile for the reaction product of Example VI(B) containing a mixture of cis and trans isomers having the structures:

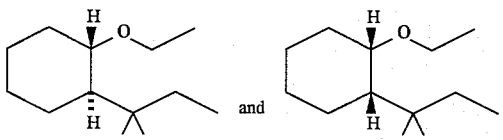

with the ratio of cis:trans isomer being 90:10. The peak indicated by reference numeral 301 is for the cis isomer having the structure:

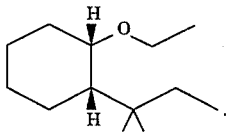

The peak indicated by reference numeral 302 is for the trans isomer having the structure:

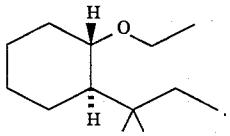

Referring to FIGS. 32 and 33, the apparatus used in producing polymeric fragrances containing the alkyl-substituted-$C_1$–$C_3$ alkoxy-$C_6$-cycloaliphatic compounds of our invention comprises a device for forming scented polyolefin (for example) pellets, which comprises a vat or container 212 into which a mixture of polyolefin such as polyethylene and an aromatic substance or scented material is placed (in this case at least one of the alkyl-substituted-$C_1$–$C_3$ alkoxy-$C_6$-cycloaliphatic compounds of our invention).

The container is closed by an air-tight lid 228 and the air-tight lid 228 is clamped to the container 212 by bolts 265.

A stirrer 273 traverses the lid or cover 228 in an air-tight manner and is rotated in a suitable manner.

Container 212 having heating coils 212A which are supplied with electric current through cable 224 from a rheostat or control 216 is operated to maintain a temperature inside the container 212 such that polyethylene or other thermoplastic polymer in the container will be maintained in the molten or liquid state. It has been found advantageous to employ a colorless, odorless polymer (e.g., polyethylene) with a viscosity ranging between 180 and 220 Saybolt seconds and having a melting point in the range of 200°–280° F. The heater 212A is operated to maintain the upper portion of the container 212 within a temperature range of from 250°–350° F. The bottom portion of the container is heated by means of heating coils 212A heated through control 220 connected thereto through a connecting wire 222 to maintain the lower portion of the container within a temperature range of from 250°–350° F.

Thus, polymer (e.g., polyethylene) is added to container 212 and is heated from 10–12 hours whereafter a scented aroma imparting material (at least one of the alkyl-substituted-$C_1$–$C_3$ alkoxy-$C_6$-cycloaliphatic compounds of our invention) is added quickly to the melt. The material must be compatible with the polyolefin and forms a homogeneous liquid melt therewith. The scented material is of a type for the particular aroma desired and formulated specifically for the scenting purpose for which the polyolefin will be employed.

Generally, about 5–30% by weight of the scented material (containing at least one of the alkyl-substituted-$C_1$–$C_3$ alkoxy-$C_6$-cycloaliphatic compounds of our invention) are added to the polyolefin.

After the scent imparting material (e.g., a composition containing at least one of the alkyl-substituted-$C_1$–$C_3$ alkoxy-$C_6$-cycloaliphatic compounds of our invention) is added to the container 212, the mixture is stirred for a few minutes, for example, 5–15 minutes, and maintained within the temperature range as indicated, supra, by means of heating coils 212A.

The controls 216 and 220 are connected, respectively, through cables 214 and 222, to heating coils 212A. The said controls 216 and 220 are also connected through cables 224 and 226, respectively, to a suitable power supply of electric current for supplying the electric power to the heating coils 212A for heating purposes.

Thereafter, the valve "V" is opened permitting the mass to flow outwardly through conduit 218/232 having a multiplicity of orifices 234, adjacent to the lower side thereof. The outer end of the conduit 218/232 is closed so that the liquid polymer (e.g., polyolefin) and aroma imparting material (e. g., at least one of the alkyl-substituted-$C_1$–$C_3$ alkoxy-$C_6$-cycloaliphatic compounds of our invention) will continuously drop through orifices 234 downwardly from conduit 232. During this time, the temperature of the polymer (e.g., polyolefin) and scent imparting material (e.g., a mixture containing at least one of the alkyl-substituted-$C_1$–$C_3$ alkoxy-$C_6$-cycloaliphatic compounds of our invention) is accurately controlled so that a temperature in the range of from about 210°–275° F. will exist in the conduit 218/232 The regulation of the temperature through controls 216 and 220 is essential in order to insure temperature balance to provide for the continuous dropping or dripping of molten polymer (e.g., polyethylene) and scenting material (e.g., one or more of the para-$C_5$ alkyl-substituted ethoxycyclohexanes of our invention) mixture through the orifices 234 at a rate which will insure the formation of droplets 236 which will fall downwardly onto a moving conveyor belt 238 caused to run between conveyor wheels 240 and 242 beneath the conduit 232.

When the droplets 236 fall onto the conveyor belt 238, they form pellets 244 which harden almost instantaneously and fall off the end of the conveyor belt 238 into a container 245 and utilized in processes as illustrated, infra.

A feature of this aspect of the process of our invention is the provision for moistening the conveyor belt 238 to insure rapid formation of the solid polymeric (e.g., polyolefin) scented pellets 244 without sticking to the belt. The conveyor belt 238 is advantageously fabricated of a material which will not normally stick to a melted plastic but a moistening means 248 insures a sufficiently cold temperature of the belt surface for an adequate formation of the pellets 244. The adequate moistening means comprises a container 250 which is continuously fed with water 254 to maintain a level for moistening a sponge element 256 which bears against the exterior of the conveyor belt 238.

THE INVENTION

The present invention provides alkyl-substituted-$C_1$–$C_3$ alkoxy-$C_6$-cycloaliphatic compounds defined according to the structure:

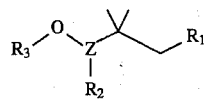

wherein Z represents meta or para cyclohexylene or meta or para phenylene and wherein $R_1$ and $R_2$ each represent the same or different methyl or hydrogen; and wherein $R_3$ represents $C_1$–$C_3$ alkyl; and wherein the moiety:

is ortho with respect to $R_2$ and para or meta with respect to the moiety:

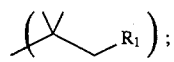

with the proviso that the sum of the number of carbon atoms in $R_1+R_2+R_3$ is 3 or 4. Alkyl-substituted-$C_1$–$C_3$ alkoxy-$C_6$-cycloaliphatic compounds defined according the structure:

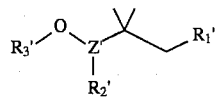

are novel compounds: wherein Z' represents meta or para cyclohexylene or meta or para phenylene and wherein $R_1'$ and $R_2'$ each represent the same or different hydrogen or methyl; and wherein $R_3'$ is $C_1$–$C_3$ alkyl; and wherein the moiety:

is ortho with respect to $R_2$ and para or meta with respect to the moiety:

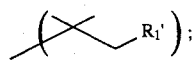

with the proviso that the sum of the number of carbon atoms in $R_1+R_2+R_3$ is 3.

The compositions of matter of our invention produced according to the processes of our invention are capable of augmenting, enhancing or providing green, fresh cut grass-like, leafy, woody, sweet, floral, muguet, balsamic, ozoney, waxy, fatty, aldehydic, citrusy, orange peel-like, privet hedge-like, cigar box-like, mahogany, dewy, rosy, twiggy, amber, cedarwood and earthy aromas with green, ozoney, woody, floral, muguet, minty, camphorceous, piney, patchouli, rosy, celery leaf-like, fatty and aldehydic topnotes and with linden blossom, cucumber, melon-like, ozoney, fatty, green, anise and fruity undertones to perfume compositions, colognes and perfumed articles (e.g., solid or liquid anionic, cationic, nonionic or zwitterionic detergents, fabric softener articles, dryer-added fabric softener articles, fabric softener compositions, cosmetic powders, hair preparations, perfumed polymers and the like).

The alkyl-substituted-$C_1$–$C_3$ alkoxy-$C_6$-cycloaliphatic compounds of our invention are prepared in the alternative by (i) reacting anethol or phenetole or ortho-methyl-substituted derivatives thereof defined according to the structure:

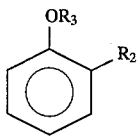

with one or more t-butyl or t-amyl halides having the structure:

according to the reaction:

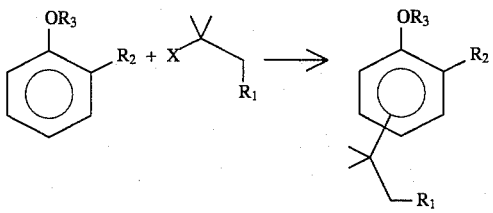

and then using the resulting compound having the structure:

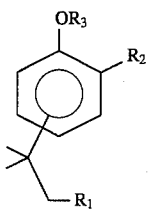

for its organoleptic properties as is, or hydrogenating the resulting compound according the reaction:

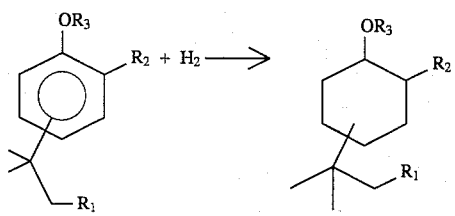

in the presence of an appropriate catalyst under appropriate reaction conditions; wherein $R_1$, $R_2$ and $R_3$ are defined, supra, and wherein X represents chloro or bromo. The compounds having the structures:

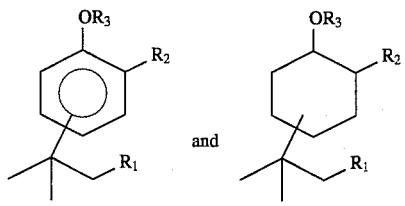

are drawn to show both meta and para isomers of the resulting reaction products, since both meta and para isomeric mixtures are formed. The resulting hydrogenation gives rise to the mixtures of stearyl isomers as set forth specifically in Examples V and VI, infra; or (ii) reacting an alkyl phenol having the structure:

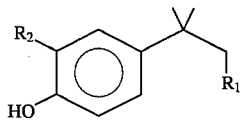

with base having the structure:

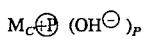

(or having the structure:

in order to form a salt having the structure:

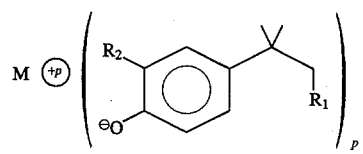

according to the reaction:

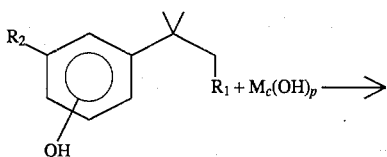

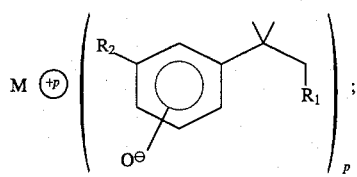

and then reacting the resulting salt having the structure:

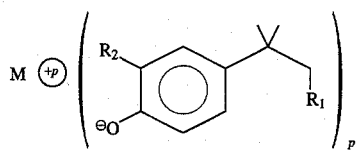

with an alkoxylating reagent shown by the symbol:

R₃[ALKOX]

which can be a methoxylating agent shown by the symbol:

[Me]

or an ethoxylating agent shown by the symbol:

[et]

according to the reaction:

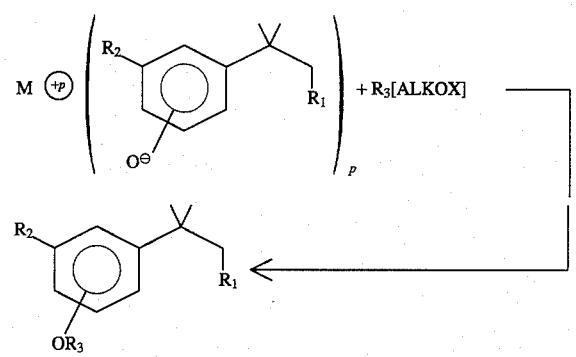

under appropriate reaction conditions.

With respect to the reaction:

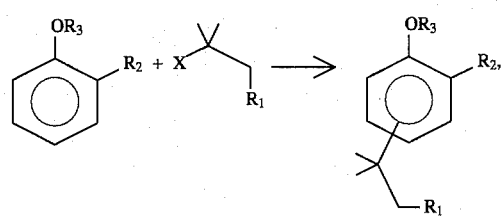

this reaction takes place in the presence of a Lewis acid catalyst having the structure:

$M_A(X_2)_N$ or having the structure:

$M_B(X_2)_{N-K}(OR)_K$ in the presence of a solvent or in the absence of a solvent. The compound having the structure:

$M_A(X_2)_N$ is a metal halide wherein $M_A$ is a metal such as boron, aluminum, iron, tin or zinc. The halide $X_2$ is chloro, bromo, iodo or fluoro. N is the valence of the metal $M_A$. Examples of the compound or Lewis acid catalyst having the structure:

$M_A(X_2)_N$ are boron trifluoride, aluminum trichloride, ferric chloride, stannic chloride or zinc chloride. On the other hand, the catalyst useful in the practice of our invention may be a complex such as boron trifluoride etherate, to wit:

$BF_3(C_2H_5OC_2H_5)$.

Furthermore, the Lewis acid catalyst useful in the practice of our invention may have the structure:

$M_B(X_2)_{N-K}(OR)_K$ wherein $M_B$ is a metal such as aluminum; wherein $X_2$ is a halide such as chloro; and R represents lower alkyl such as methyl, ethyl or isopropyl. N is the valence of the metal $M_B$ and K represents the number of alkoxy moieties wherein:

$0 < K < N$ and wherein:

$N \leq 4$.

The reaction takes place in the presence of a solvent and examples of solvents are 2-nitropropane having the structure:

(the most preferred solvent); nitromethane or hydrocarbons (e.g., cyclohexane).

The temperature of reaction may be between about 0° C. up to about 40° C. with a preferred temperature range of from about 0° C. up to about 5° C.

The preferred reactants of the genus:

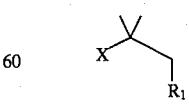

are those wherein X is chloro due to economic reasons.

At the end of the reaction, the reaction mass is distilled in order to yield substantially pure materials defined according to the structure:

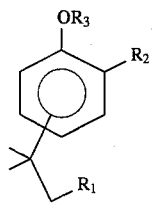

wherein $R_1$, $R_2$ and $R_3$ are defined, supra.

The compounds defined according to the structure:

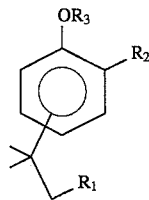

are then further reacted by means of reduction using hydrogen and an appropriate hydrogenation catalyst for the reaction:

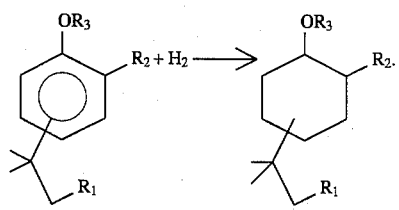

The hydrogenation catalyst used and the conditions of the hydrogenation reaction may be varied and in so varying such catalysts and conditions of reaction, various ratios of cis and trans isomers will be produced. Thus, when the hydrogenation is carried out using 3% ruthenium on carbon catalyst at a temperature in the range of from 110° up to 145° C. and at a pressure in the range of from 400 up to 700 psig for a period of time of from 0.25 up to 10 hours, approximately at 50:50 cis and trans mixture of compounds will result. On the other hand, a preponderant amount of cis isomer will be produced when using ruthenium on aluminum oxide or rhodium on aluminum oxide catalyst (with the ruthenium or rhodium being from about 3 up to about 8% by weight of the catalyst) at a temperature of from about 80° up to about 100° C.; at a pressure of about 400 psig; and for a period of time of from about 0.25 up to about 3 hours. In both cases, in the hydrogenation reaction, methanol, ethanol or n-propanol solvents are to be used.

With reference to the reaction sequence:

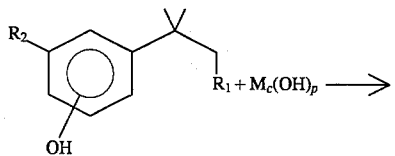

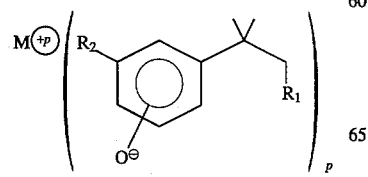

and

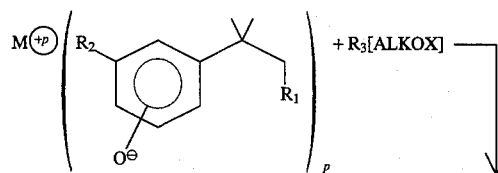

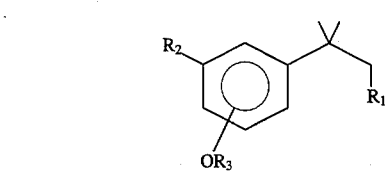

in the compund: $M_c^{\oplus}$ $(OH^{\ominus})_p$ also shown as: $M_c(OH)_p$ $M_C$ represents an alkali metal such as sodium, potassium or lithium or an alkaline earth metal such as calcium or magnesium. When $M_C$ represents an alkali metal, P is 1 and when $M_C$ is an alkaline earth metal, P is 2. Preferably, $M_C$ is sodium. Preferably, the ethoxylation reagent is diethyl sulfate, although ethoxylation reagents such as ethyl chloride, ethyl bromide and ethyl iodide are also useful ethoxylation reagents.

Preferably, the methoxylation reagent is dimethyl sulfate, although methoxylation reagents such as methyl chloride, methyl bromide and methyl iodide are also useful methoxylation reagents.

An additional ethoxylation reagent is a mixture of ethyl alcohol and 93% concentrated sulfuric acid with the ratio of the ethyl alcohol:concentrated sulfuric acid being 50:50 (weight:weight).

With reference to the reaction:

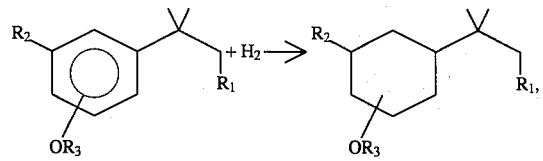

this reaction can take place in the presence of a 3% ruthenium/carbon catalyst at 110°–145° C.; a pressure of 400–700 psig and a time of reaction of from 0.25 up to 10 hours, whereby the resulting mixture is a 50:50 mixture of cis:trans isomers, for example, the cis isomer having the structure:

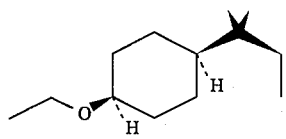

and the trans isomer having the structure:

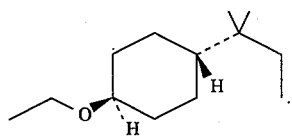

Alternatively, other ruthenium-based hydrogenation catalysts may be used and these ruthenium catalysts are disclosed and claimed in U.S. Pat. No. 5,403,805 issued on Apr. 4, 1995, the specification for which is incorporated herein by reference. Furthermore, other ruthenium-based catalysts can be used, for example, those set forth in U.S. Pat. No. 5,426,216 issued on Jun. 20, 1995, the specification for which is incorporated by reference herein.

Reaction mixtures preponderant in the cis isomers such as the isomer having the structure:

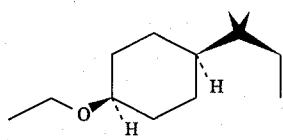

can be produced by using ruthenium on aluminum oxide catalysts or rhodium on aluminum oxide catalysts with the amount of ruthenium or rhodium being from about 3 up to about 8% by weight of the catalyst; at a temperature in the range of 80°–100° C.; at a pressure of about 400 psig; and for a time of reaction of 0.25 up to 3 hours.

In all cases, the use of a solvent is required and such solvent is methanol, ethanol or n-propanol.

In summary, the ratio of cis:trans and the ratio of optical isomers obtained is a function of the conditions of reaction. For example, the isomers of the compound having the structure:

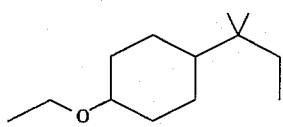

are as follows:

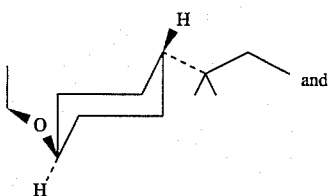

and

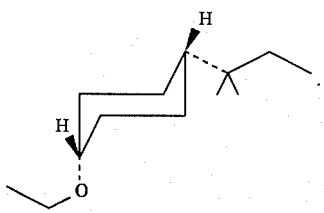

Thus, for example, in carrying out the reaction:

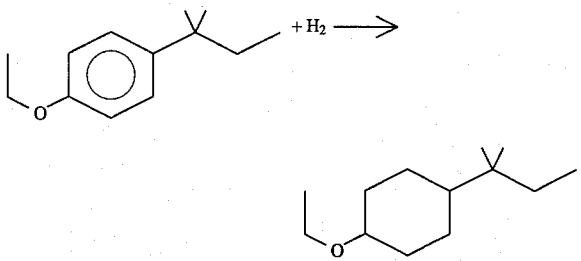

according to Example I(B) in the presence of a 3% ruthenium on carbon catalyst when the reaction takes place at a temperature in the range of 110°–120° C. at a pressure of 600 psig for a period of time of 6.5 hours in the presence of an isopropanol solvent, where the weight ratio of 3% ruthenium on carbon catalyst:reactant having the structure:

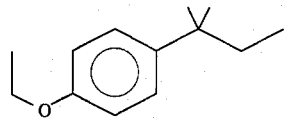

is about 0.03:1 and the ratio of solvent:reactant having the structure:

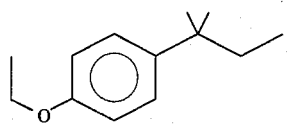

is 1:2.95 and the weight ratio of reaction products having the structures:

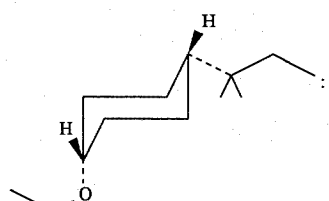

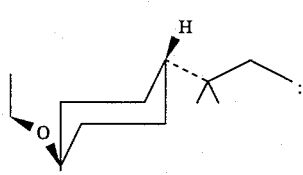

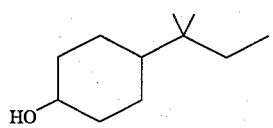

is 48:48:4, respectively.

With respect to the etherification reaction:

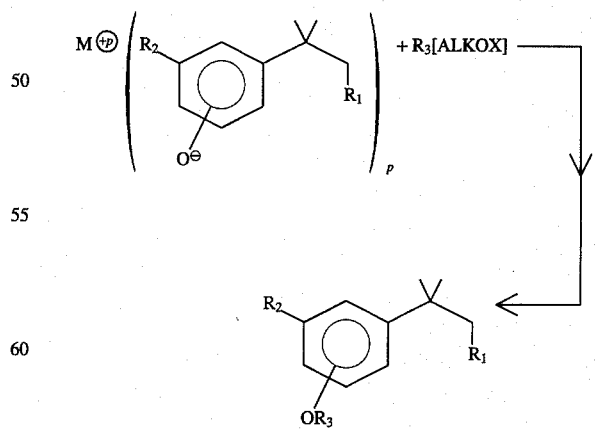

this etherification reaction preferably takes place in the presence of a "phase transfer reagent" such as ALIQUAT® 336 (trademark of the Henkel Corporation of Minneapolis, Minn.), tricapryl methyl ammonium chloride having the structure:

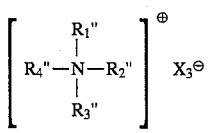

wherein $R_1''$, $R_2''$ and $R_3''$ represent capryl; $X_3$ represents chloro; and $R_4''$ is methyl. Other phase transfer reagents may also be used wherein X represents chloro or bromo; $R_1''$, $R_2''$ and $R_3''$ are the same or different $C_6$–$C_{10}$ alkyl and $R_4''$ represents $C_1$–$C_3$ alkyl.

The etherification reaction may take place in the presence of a calcium phenate catalyst having the structure:

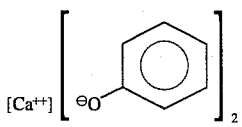

in accordance with the procedure of the People's Republic of China Patent No. 1,023,643 (PCT Patent Application No. 91 CN 108 407 assigned to the China PetrochemiCal General Corporation having DERWENT Accession No. 93-101478/13.

The following Table I sets forth the perfumery properties of various compositions of matter so useful in the practice of our invention.

TABLE I

| Description of Composition | Perfumery Properties |
|---|---|
| The compound having the structure:<br><br>(structure) <br><br>prepared according to Example I(B) bulk distillation fraction Nos. 6–14 (50:50 cis:trans isomer mixture). | A green (fresh cut grass-like), woody, floral (muguet), balsamic aroma with green, ozoney, woody, floral (muguet) topnotes and linden blossom, cucumber and melon-like undertones. |
| The compound having the structure:<br><br>(structure)<br><br>(preponderantly cis isomer) prepared according to Example II(A) (iv), fraction No. 9. | A powerful green, floral, ozoney aroma with green, floral and ozoney topnotes. |
| The compound having the structure:<br><br>(structure)<br><br>(predominantly the trans isomer) prepared according to the process of Example II(A) (iv), distillation fraction No. 25. | A floral aroma with floral, green and ozoney topnotes. |

TABLE I-continued

| Description of Composition | Perfumery Properties |
|---|---|
| A 2:1 cis:trans isomer mixture with the cis compound having the structure:<br><br>(structure)<br><br>and the trans compound having the structure:<br><br>(structure)<br><br>prepared according to Example II(B), distillation fractions Nos. 7–12. | A waxy, citrusy, orange peel-like, fresh floral aroma with ozoney undertones. |
| The compound having the structure:<br><br>(structure)<br><br>prepared according to Example III(B), distillation fraction No. 8. | An ozoney, green, privet hedge-like, floral, fatty aroma with fatty, ozoney and green undertones. |
| The compound having the structure:<br><br>(structure)<br><br>prepared according to Example IV(A), | A balsamic, cigar box-like, mahogany aroma with mint topnotes. |
| The mixture of isomers having the structure:<br><br>(structure)<br><br>prepared according to Example IV(B), distillation fraction No. 8. | A green, woody, sweet aroma with anise undertones and minty, camphoraceous, piney and patchouli topnotes. |

TABLE I-continued

| Description of Composition | Perfumery Properties |
|---|---|
| A mixture of para and meta isomers having the structures:<br>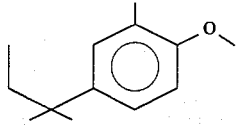<br>and<br>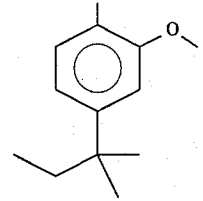<br>prepared according to Example V(A). | A green, leafy, rosy, twiggy aroma with fresh green, rosy and celery leaf topnotes. |
| A mixture of compounds having the structures:<br>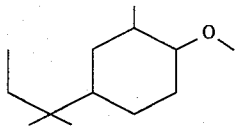<br>and<br>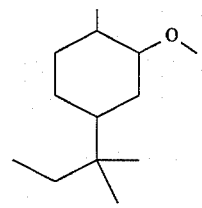<br>(mixture of cis and trans isomers) prepared according to Example V(B). | A green, ozoney, fatty, woody, floral, amber aroma with green, fatty and ozoney topnotes. |
| A mixture of compounds having the structures:<br>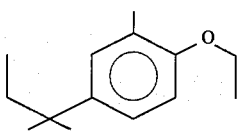<br>and<br>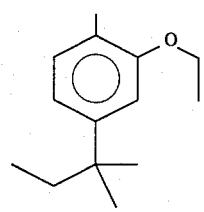<br>prepared according to Example VI(A), distillation fraction No. 8. | A cedarwood, cigar box-like aroma with fruity undertones. |
| A mixture of isomers having the structures:<br>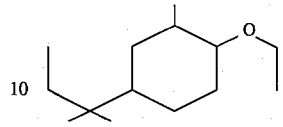<br>and<br>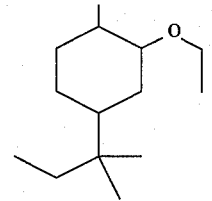<br>prepared according to the process of Example VI(B), distillation fraction No. 11. | A fatty, waxy, aldehydic, muguet, privet hedge, dewy, rose aroma with fatty, aldehydic and floral topnotes. |
| A mixture of compounds having the structures:<br>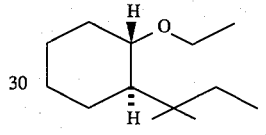<br>and<br>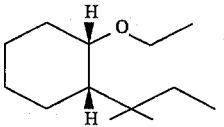<br>prepared according to Example VII(B), distillation fraction No. 9. | An earthy aroma with green topnotes. |

One or more of the alkyl-substituted-$C_1$–$C_3$ alkoxy-$C_6$-cycloaliphatic compounds prepared in accordance with the processes of our invention and one or more auxiliary perfume ingredients including, for example, alcohols, aldehydes, ketones, terpenic hydrocarbons, nitriles, esters, lactones, ethers other than the ethers of our invention, natural essential oils and synthetic essential oils may be admixed so that the combined odors of the individual components produce a pleasant and desired fragrance, particularly and preferably in the citrus, fruity and woody types of fragrances. Such compositions usually contain:

(a) the main note or the "bouquet" or foundation stone of the composition;

(b) modifiers which round off and accompany the main note;

(c) fixatives which include odorous substances which lend a particular note to the perfume throughout all stages of evaporation and substances which retard evaporation; and (d) topnotes which are usually low boiling, fresh smelling materials.

In perfume compositions, it is the individual components which contribute their particular olfactory characteristics, however, the overall sensory effect of the perfume compositions will be at least the sum total of the effects of each of the ingredients. Thus, the alkyl-substituted-$C_1$-$C_3$ alkoxy-$C_6$-cycloaliphatic compounds of our invention produced in accordance with the processes of our invention can be used to alter, modify or enhance the aroma characteristics of a perfume composition, for example, by utilizing or moderating the olfactory reaction contributed by another ingredient in the composition. In the alternative, the alkyl-substituted-$C_1$-$C_3$ alkoxy-$C_6$-cycloaliphatic compounds of our invention can be used to formulate a perfume composition by themselves.

The amount of the alkyl-substituted-$C_1$-$C_3$ alkoxy-$C_6$-cycloaliphatic compounds prepared in accordance with the processes of our invention which will be effective in perfume compositions as well as in perfumed articles (e.g., anionic, cationic, nonionic or zwitterionic detergents, soaps, fabric softener compositions, fabric softener articles and perfumed polymers) and colognes depends upon many factors including the other ingredients, their amounts and the effects which are desired. It has been found that perfume compositions containing as little as 0.01% of at least one of the alkyl-substituted-$C_1$-$C_3$ alkoxy-$C_6$-cycloaliphatic compounds of our invention prepared in accordance with the processes of our invention or even less (e.g., 0.005%) can be used to impart, augment or enhance green, fresh cut grass-like, leafy, woody, sweet, floral, muguet, balsamic, ozoney, waxy, fatty, aldehydic, citrusy, orange peel-like, privet hedge (*Ligustrum vulgare*)-like, cigar box-like, mahogany, dewy, rosy, twiggy, amber, cedarwood, and earthy aromas with green, ozoney, woody, floral, muguet, minty, camphoraceous, piney, patchouli, rosy, celery leaf-like, fatty and aldehydic topnotes and with linden blossom, cucumber, melon-like, ozoney, fatty, green, anise and fruity undertones to soaps, cosmetics, anionic, cationic, nonionic or zwitterionic detergents, fabric softener articles, micorporous polymers, particularly acrylic resins, polyethylenes and other products. The amount employed can range up to 100% of the fragrance components and will depend on considerations of cost, nature of the end product, the effect desired on the finished product and the particular fragrance sought. The alkyl-substituted-$C_1$-$C_3$ alkoxy-$C_6$-cycloaliphatic compounds of our invention prepared in accordance with the processes of our invention are useful (taken alone or together with other ingredients in perfume compositions) as (an) olfactory component(s) in detergents and soaps, space odorants and deodorants, perfumes, colognes, toilet water, bath preparations such as creams, deodorants, hand lotions and sun screens; powders such as talcs, dusting powders, face powders, microporous "perfumed" slow release polymers and the like.

When used as (an) olfactory component(s) in perfumed articles, as little as 0.005% of at least one of the alkyl-substituted-$C_1$-$C_3$ alkoxy-$C_6$-cycloaliphatic compounds prepared in accordance with the processes of our invention, will suffice to impart, augment or enhance green, fresh cut grass-like, leafy, woody, sweet, floral, muguet, balsamic, ozoney, waxy, fatty, aldehydic, citrusy, orange peel-like privet hedge (*Ligustrum vulgare*)-like, cigar box-like, mahogany, dewy, rosy, twiggy, amber, cedarwood and earthy aromas with green, ozoney, woody, floral, muguet, minty, camphoraceous, piney, patchouli, rosy, celery leaf-like fatty and aldehydic topnotes and linden blossom, cucumber, melon-like, ozoney, fatty, green, anise and fruity undertones. Generally no more than 6% of at least one of the alkyl-substituted-$C_1$-$C_3$ alkoxy-$C_6$-cycloaliphatic compounds of our invention based on the ultimate end product is required in the perfumed article. Accordingly, the range of use of the alkyl-substituted-$C_1$-$C_3$ alkoxy-$C_6$-cycloaliphatic compounds of our invention in perfumed articles, per se, is from about 0.005% up to about 6% by weight based on the perfumed article.

In addition, the perfume composition or fragrance composition of our invention can contain a vehicle or carrier for the alkyl-substituted-$C_1$-$C_3$ alkoxy-$C_6$-cycloaliphatic compounds prepared in accordance with the processes of our invention. The vehicle can be a liquid such as a non-toxic alcohol, e.g., ethyl alcohol; a non-toxic glycol, e.g., propylene glycol or dipropylene glycol or the like. The carrier can be an absorbent solid such as a gum (e.g., gum arabic, guar gum or xanthan gum or combinations thereof) or components for encapsulating the composition (such as by coacervation) or using prepolymers such as urea-formaldehyde prepolymers which are able to form a urea-formaldehyde polymer capsule around a liquid perfume center.

It will thus be apparent that the alkyl-substituted-$C_1$-$C_3$ alkoxy-$C_6$-cycloaliphatic compounds prepared in accordance with the processes of our invention can be utilized to alter, modify or enhance sensory properties particularly organoleptic properties such as fragrances of a wide variety of consumable materials.

The following Examples I-VII, inclusive, set forth means for preparing the alkyl-substituted-$C_1$-$C_3$ alkoxy-$C_6$-cycloaliphatic compounds of our invention. The examples following Example VII, infra, set forth illustrations of organoleptic utilities of the alkyl-substituted-$C_1$-$C_3$ alkoxy-$C_6$-cycloaliphatic compounds of our invention.

All parts and percentages given herein are by weight unless otherwise specified.

EXAMPLE I

PREPARATION OF ETHYL 4-(1',1'-DIMETHYLPROPYL)CYCLOHEXYL ETHER

Example I(A)

Reactions:

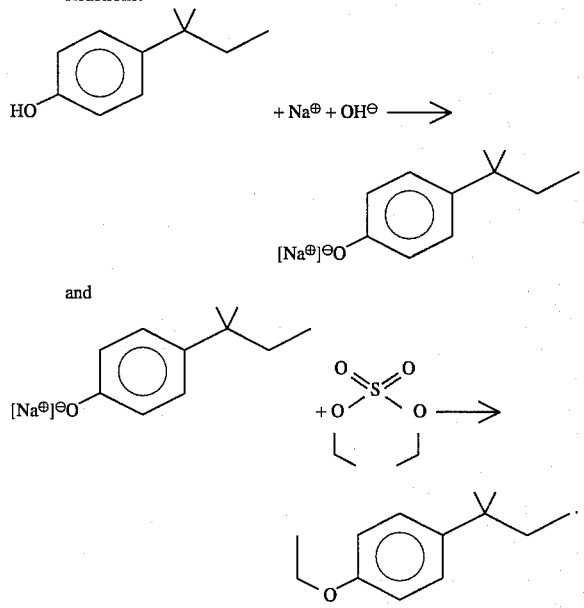

Summary Reaction:

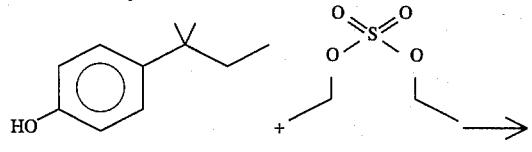

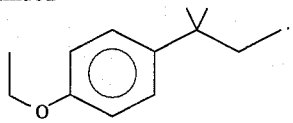

Into a 2 liter reaction vessel equipped with stirrer, thermometer, reflux condenser and heating mantle are placed the following ingredients:

sodium hydroxide—156 grams;
water—468 grams; and
ALIQUAT® 336—25 grams.

The resulting mixture is heated to 45° C.

Over a period of 1 hour 500 grams of t-amylphenol having the structure:

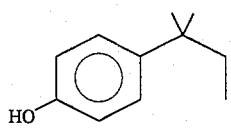

is added to the reaction mass with stirring while maintaining the temperature at 45° C.

Over a period of 2 hours while maintaining the reaction mass at 45° C., diethyl sulfate having the structure:

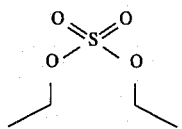

is added to the reaction mass. The reaction mass is maintained at 45° C. with stirring for an additional 3 hour period.

At the end of the 3 hour period, 500 grams of 25% aqueous sodium hydroxide is added to the reaction mass and heated at 45° C. for a period of 1 hour.

At the end of the 1 hour period, the reaction mass is cooled to room temperature and the reaction mass now exists in two phases: an organic phase and an aqueous phase. The organic phase is admixed with 50 ml of toluene. The organic phase is then dried over anhydrous magnesium sulfate. The resulting product is then admixed with 40 grams of propionic anhydride and the resulting mixture is heated to 100° C. and maintained at 100° C. with stirring for a period of 0.5 hours. The resulting product is then cooled to 60° C. and admixed with 100 ml water. The resulting product now exists in two phases: an organic phase and an aqueous phase. The organic phase is separated from the aqueous phase and the organic phase is washed, consecutively, with an equal volume of saturated aqueous sodium chloride followed by saturated aqueous sodium bicarbonate. The resulting product is dried over anhydrous magnesium sulfate and fractionally distilled yielding the following fractions:

| Fraction Number | Vapor Temperature (°C.) | Liquid Temperature (°C.) | Vacuum mm/Hg Pressure | Reflux Ratio |
|---|---|---|---|---|
| 1 | 20/85 | 20/105 | 0.8/0.8 | 4:1 |
| 2 | 84 | 103 | 0.67 | 9:1 |
| 3 | 84 | 104 | 0.59 | 9:1 |
| 4 | 84 | 103 | 0.56 | 9:1 |
| 5 | 84 | 103 | 0.55 | 9:1 |
| 6 | 83 | 104 | 0.55 | 9:1 |
| 7 | 83 | 104 | 0.53 | 9:1 |
| 8 | 83 | 104 | 0.53 | 9:1 |
| 9 | 86 | 104 | 1.1 | 9:1 |
| 10 | 83 | 101 | 0.7 | 9:1 |
| 11 | 88 | 104 | 1.03 | 9:1 |
| 12 | 88 | 104 | 1.06 | 9:1 |
| 13 | 89 | 105 | 1.07 | 9:1 |
| 14 | 88 | 107 | 1.06 | 4:1 |
| 15 | 89 | 116 | 1.07 | 4:1 |

The resulting product has the structure:

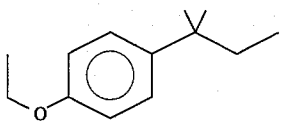

as confirmed NMR, IR and mass spectral analyses.

Example I(B)

Reaction:

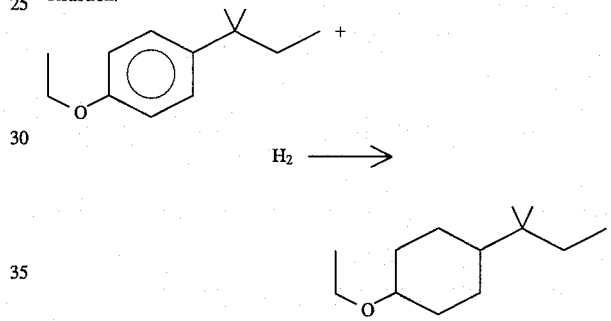

Into a 1 liter autoclave equipped with a hydrogen pressurization tube are placed the following materials:

295 grams of the compound having the structure:

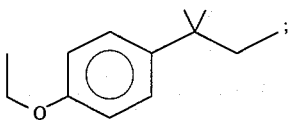

8.8 grams 3% ruthenium on carbon; and grams anhydrous isopropyl alcohol.

The autoclave is sealed and pressurized with hydrogen. The temperature of the autoclave is raised to 110°–120° C. and pressurized at 600 psig with hydrogen. The hydrogen pressurization continues for a period of 6.5 hours at a temperature of 110°–120° C.

At the end of the 6.5 hour period, the autoclave is cooled and opened and the contents are filtered.

The resulting filtrate is distilled using a fractional distillation column yielding the following fractions:

| Fraction Number | Vapor Temperature (°C.) | Liquid Temperature (°C.) | Vacuum mm/Hg Pressure |
|---|---|---|---|
| 1 | 23/30 | 23/105 | 100/30 |
| 2 | 91 | 106 | 3 |
| 3 | 97 | 112 | 3 |

-continued

| Fraction Number | Vapor Temperature (°C.) | Liquid Temperature (°C.) | Vacuum mm/Hg Pressure |
| --- | --- | --- | --- |
| 4 | 96 | 112 | 4 |
| 5 | 97 | 115 | 4 |
| 6 | 95 | 115 | 4 |
| 7 | 95 | 118 | 3.5 |
| 8 | 99 | 118 | 4.0 |
| 9 | 100 | 122 | 4.0 |
| 10 | 99 | 126 | 3.0 |
| 11 | 100 | 133 | 3.0 |
| 12 | 94 | 190 | 1.1 |
| 13 | 94 | 192 | 1.0 |
| 14 | 94 | 193 | 1.0 |
| 15 | 82 | 212 | 0.8 |

Fractions 6–14 are bulked. Fractions 6–14 consist of the compound having the structure:

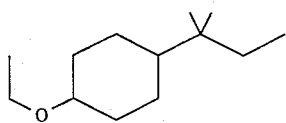

and a small quantity of the compound having the structure:

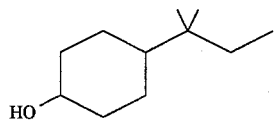

with the ratio of isomers being 48 parts by weight of the compound having the structure:

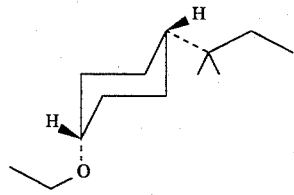

48 parts by weight of the compound having the structure:

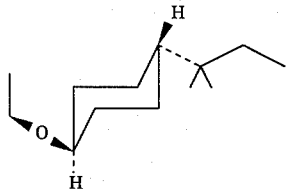

4 parts by weight of the compound having the structure:

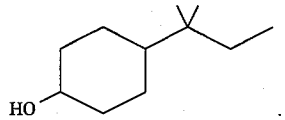

Furthermore, fraction 5 consists of the compound having the structure:

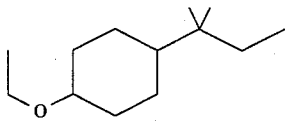

and a small quantity of the compound having the structure:

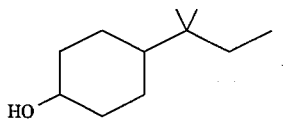

with the ratio of isomers being 85 parts by weight of the compound having the structure:

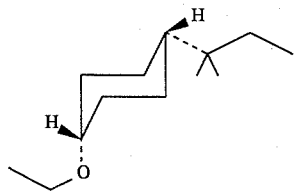

10 parts by weight of the compound having the structure:

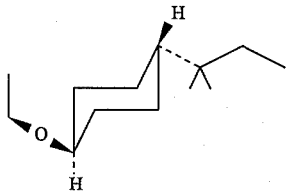

5 parts by weight of the compound having the structure:

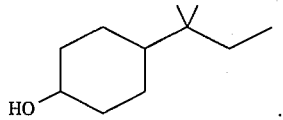

EXAMPLE II

PREPARATION OF ETHYL 4-(1',1'-DIMETHYLPROPYL)CYCLOHEXYL ETHER

Example II(A)(i)

Reaction:

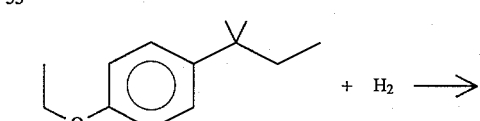

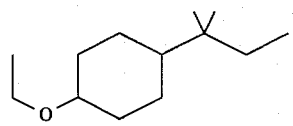

Into a 500 cc autoclave are placed the following materials:

(a) compound having the structure:

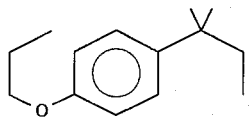

prepared according to Example I(A), 330 grams;

(b) 3% ruthenium on aluminum oxide, 1.1 grams; and (c) isopropyl alcohol, 50 grams.

The autoclave is sealed and pressurized to 600 pounds per square inch and the contents are heated at 115°–120° C. for a period of 5 hours.

At the end of the 5 hour period, the autoclave is cooled and then depressurized and opened. The resulting reaction mass is filtered and fractionally distilled yielding the following fractions:

| Fraction Number | Vapor Temperature (°C.) | Liquid Temperature (°C.) | Vacuum mm/Hg Pressure | Reflux Ratio | Ratio of CIS:TRANS ISOMER |
|---|---|---|---|---|---|
| 1  | 23/30 | 23/102 | 150/30 | 100% |  |
| 2  | 89 | 106 | 3.0 | 4:1 |  |
| 3  | 93 | 107 | 3.0 | 4:1 |  |
| 4  | 93 | 108 | 3.0 | 4:1 |  |
| 5  | 95 | 107 | 3.2 | 1:1 |  |
| 6  | 95 | 108 | 3.0 | 1:1 |  |
| 7  | 96 | 109 | 3.5 | 1:1 |  |
| 8  | 96 | 109 | 3.5 | 1:1 |  |
| 9  | 94 | 107 | 3.0 | 1:1 | 68:32 |
| 10 | 96 | 109 | 3.2 | 1:1 |  |
| 11 | 96 | 109 | 3.2 | 1:1 |  |
| 12 | 97 | 109 | 3.2 | 1:1 |  |
| 13 | 96 | 109 | 3.0 | 1:1 |  |
| 14 | 97 | 109 | 3.2 | 1:1 |  |
| 15 | 97 | 110 | 3.0 | 1:1 |  |
| 16 | 98 | 109 | 3.0 | 1:1 | 40:60 |
| 17 | 98 | 110 | 3.0 | 1:1 |  |
| 18 | 99 | 110 | 3.0 | 1:1 |  |
| 19 | 96 | 110 | 2.0 | 1:1 |  |
| 20 | 98 | 110 | 2.5 | 1:1 |  |
| 21 | 96 | 111 | 2.0 | 1:1 | 96:4 |
| 22 | 93 | 114 | 1.0 | 1:1 |  |
| 23 | 67 | 190 |  |  |  |

Fractions 6–21 are bulked.

Example II(A)(ii)

Reaction:

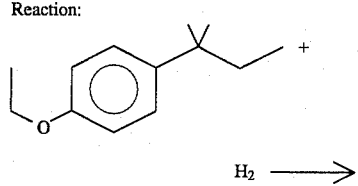

Example II(A)(i) is repeated and the following fractional distillation fractions are obtained:

| Fraction Number | Vapor Temperature (°C.) | Liquid Temperature (°C.) | Vacuum mm/Hg Pressure | Reflux Ratio |
|---|---|---|---|---|
| 1  | 23/33 | 23/105 | 150/40 | 100% |
| 2  | 90 | 115 | 8.0 | 4:1 |
| 3  | 93 | 114 | 8.5 | 4:1 |
| 4  | 100 | 114 | 8.0 | 4:1 |
| 5  | 102 | 113 | 8.0 | 4:1 |
| 6  | 105 | 114 | 8.0 | 4:1 |
| 7  | 105 | 114 | 8.0 | 4:1 |
| 8  | 102 | 112 | 6.0 | 1:1 |
| 9  | 101 | 112 | 5.0 | 1:3 |
| 10 | 101 | 113 | 5.5 | 1:3 |
| 11 | 101 | 114 | 5.5 | 1:3 |
| 12 | 101 | 114 | 5.5 | 1:3 |
| 13 | 102 | 114 | 5.0 | 1:3 |
| 14 | 102 | 114 | 5.0 | 1:3 |
| 15 | 104 | 116 | 5.0 | 1:3 |
| 16 | 105 | 118 | 5.0 | 1:3 |
| 17 | 106 | 118 | 5.0 | 1:3 |
| 18 | 107 | 120 | 5.0 | 1:3 |
| 19 | 110 | 130 | 5.0 | 1:3 |
| 20 | 101 | 200 | <1 | 1:3 |

Fractions 9–18 are bulked.

Example II(A)(iii)

Reaction:

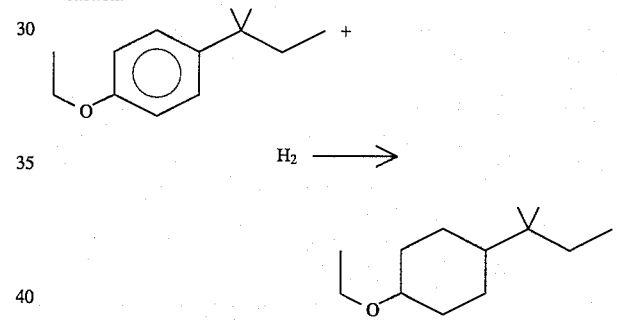

The procedure of Example II(A)(ii) is repeated yielding the following distillation fractions:

| Fraction Number | Vapor Temperature (°C.) | Liquid Temperature (°C.) | Vacuum mm/Hg Pressure | Reflux Ratio | Ratio of CIS:TRANS ISOMER |
|---|---|---|---|---|---|
| 1  | 23/26 | 23/105 | 150/20 | 100% |  |
| 2  | 99 | 114 | 9.0 | 4:1 |  |
| 3  | 100 | 113 | 9.0 | 4:1 |  |
| 4  | 101 | 112 | 7.0 | 1:1 |  |
| 5  | 100 | 110 | 6.0 | 1:1 |  |
| 6  | 99 | 109 | 5.0 | 1:3 | 71:29 |
| 7  | 100 | 110 | 5.0 | 1:3 |  |
| 8  | 99 | 110 | 4.8 | 1:3 |  |
| 9  | 100 | 110 | 4.8 | 1:3 |  |
| 10 | 100 | 110 | 4.8 | 1:3 |  |
| 11 | 101 | 111 | 4.8 | 1:3 |  |
| 12 | 102 | 112 | 4.8 | 1:3 | 57:43 |
| 13 | 103 | 113 | 4.8 | 1:3 |  |
| 14 | 103 | 113 | 4.8 | 1:3 |  |
| 15 | 105 | 113 | 4.8 | 1:3 |  |
| 16 | 106 | 113 | 4.8 | 1:3 |  |
| 17 | 107 | 115 | 5.2 | 1:3 |  |
| 18 | 107 | 115 | 5.1 | 1:3 | 30:70 |
| 19 | 110 | 117 | 5.2 | 1:3 |  |
| 20 | 107 | 115 | 4.5 | 1:3 |  |

-continued

| Fraction Number | Vapor Temperature (°C.) | Liquid Temperature (°C.) | Vacuum mm/Hg Pressure | Reflux Ratio | Ratio of CIS:TRANS ISOMER |
|---|---|---|---|---|---|
| 21 | 106 | 122 | 4.5 | 1:3 | |
| 22 | 78 | 160 | 3.0 | 1:3 | |

Fractions 8–19 are bulked.

Example II(A)(iv)

Separation of isomer having the structure:

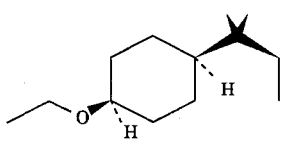

from isomer having the structure:

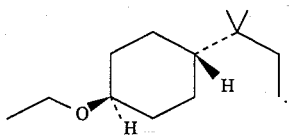

The bulked distillation fractions for Example II(A)(i), Example II(A)(ii) and Example II(A)(iii) are bulked:

Example II(A)(i), bulked fractions 6–21;
Example II(A)(ii), bulked fractions 9–18; and Example II(A)(iii), bulked fractions 8–19.

The resulting bulked fractions redistilled yielding the following fractions:

| Fraction Number | Vapor Temperature (°C.) | Liquid Temperature (°C.) | Vacuum mm/Hg Pressure | Reflux Ratio | Percent Isomer |
|---|---|---|---|---|---|
| 1 | 60 | 95 | 4.5 | 9/1 | |
| 2 | 85 | 96 | 5.5 | 19:1 | |
| 3 | 85 | 97 | 5.75 | 19:1 | |
| 4 | 85 | 98 | 5.75 | 19:1 | |
| 5 | 83 | 97 | 5.5 | 19:1 | |
| 6 | 81 | 97 | 5.5 | 19:1 | |
| 7 | 81 | 97 | 5.5 | 19:1 | |
| 8 | 81 | 97 | 5.5 | 4:1 | |
| 9 | 81 | 97 | 5.5 | 4:1 | 97% cis |
| 10 | 81 | 97 | 5.5 | 4:1 | |
| 11 | 81 | 98 | 5.25 | 4:1 | |
| 12 | 81 | 97 | 5.5 | 4:1 | |
| 13 | 80 | 97 | 5.4 | 4:1 | |
| 14 | 83 | 99 | 5.6 | 4:1 | |
| 15 | 82 | 98 | 5.5 | 4:1 | |
| 16 | 83 | 98 | 5.5 | 4:1 | |
| 17 | 84 | 100 | 5.5 | 4:1 | |
| 18 | 85 | 100 | 5.5 | 4:1 | |
| 19 | 87 | 100 | 5.5 | 4:1 | |
| 20 | 87 | 100 | 5.5 | 4:1 | |
| 21 | 87 | 100 | 5.5 | 9:1 | |
| 22 | 89 | 100 | 5.5 | 9:1 | |
| 23 | 89 | 100 | 5.5 | 9:1 | |
| 24 | 89 | 100 | 5.5 | 9:1 | |
| 25 | 89 | 100.5 | 5.5 | 9:1 | 99% trans |
| 26 | 82 | 98 | 3.2 | 9:1 | |
| 27 | 79 | 96 | 2.8 | 9:1 | |
| 28 | 82 | 101 | 3.5 | 9:1 | |
| 29 | 79 | 106 | 3.5 | 9:1 | |
| 30 | 78 | 130 | 3.0 | 9:1 | |

Example II(B)

Reaction:

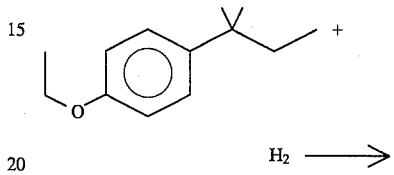

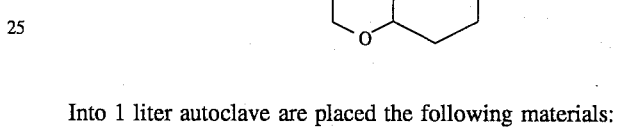

Into 1 liter autoclave are placed the following materials:

(a) the compound having the structure:

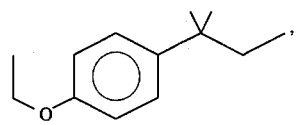

250 grams;

(b) isopropyl alcohol, 250 grams; and (c) 3% ruthenium on aluminum oxide catalyst, 3.0 grams.

The autoclave is closed and pressurized with hydrogen at psig and heated to a temperature of 75°–80° C. The hydrogen feed is continued for a period of 1 hour whereupon a ratio of cis:trans isomer (isomers having the structures:

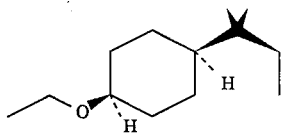

(cis isomer)

and

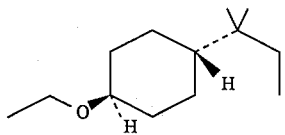

(trans isomer)

is 55:42.

The above reaction is repeated using the same materials but run at 45°–50° C. At the end of the 1 hour, the cis:trans isomer ratio is 64:36.

The products of the above two "runs" are bulked and fractionally distilled yielding the following fractions:

| Fraction Number | Vapor Temperature (°C.) | Liquid Temperature (°C.) | Vacuum mm/Hg Pressure | Reflux Ratio | Ratio of CIS:TRANS ISOMER |
|---|---|---|---|---|---|
| 1 | 23/31 | 23/110 | 150/25 | 100% | |
| 2 | 110 | 112 | 5.5 | 9:1 | |
| 3 | 111 | 113 | 6.0 | 4:1 | 88.5:11.5 |
| 4 | 109 | 114 | 5.5 | 4:1 | |
| 5 | 111 | 115 | 6.0 | 4:1 | 85.5:14.5 |
| 6 | 111 | 114 | 6.0 | 4:1 | |
| 7 | 111 | 115 | 6.0 | 4:1 | 82:18 |
| 8 | 111 | 115 | 6.0 | 4:1 | |
| 9 | 111 | 115 | 5.0 | 4:3 | 73.5:24.5 |
| 10 | 112 | 115 | 5.0 | 4:1 | |
| 11 | 114 | 118 | 5.0 | 4:1 | 52.3:47.7 |
| 12 | 116 | 120 | 5.0 | 4:1 | |
| 13 | 117 | 145 | 5.0 | 4:1 | 13:87 |
| 14 | 105 | 190 | <1 | 4:1 | |

Fractions 6–11 are bulked. The resulting product has a ratio of cis:trans isomer of 2:1.

EXAMPLE III

PREPARATION OF 4-t-AMYLCYCLOHEXANE-1-PROPYL ETHER

Example III(A)

Reactions:

(i)
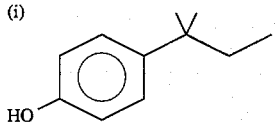 + Na⊕ + OH⊖ ⟶

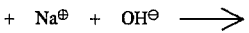 ;

and (ii)
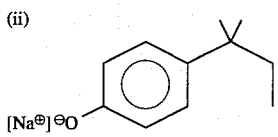 + 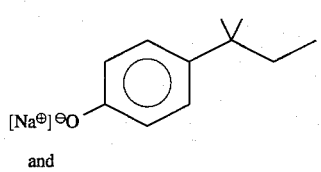 ⟶

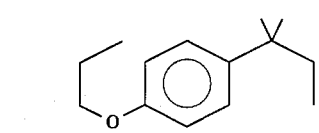

Into a 2 liter reaction vessel equipped with stirrer, thermometer, reflux condenser and heating mantle are placed:
sodium hydroxide, 141 grams;
water, 423 grams; and
ALIQUAT® 336, 19 grams.
The resulting mixture is heated to 68° C.
Over a period of 1 hour, 383 grams of t-amylphenol having the structure:

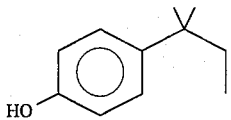

is added to the reaction mass with stirring while maintaining the temperature at 68° C.

Over a period of 2 hours while maintaining the reaction mass at 68° C., n-propylbromide is added to the reaction mass. The reaction mass is maintained at 68° C. with stirring for an additional 10 hour period.

At the end of the 10 hour period, 500 grams of 25% aqueous sodium hydroxide is added to the reaction mass and the resulting reaction mass is heated at 45° C. for a period of hour.

At the end of the 1 hour period, the reaction mass is cooled to room temperature and the reaction mass now exists in two phases: an organic phase and an aqueous phase. The organic phase is admixed with 50 ml of toluene. The organic phase is then dried over anhydrous magnesium sulfate. The resulting product is then admixed with 40 grams of propionic anhydride and the resulting mixture is heated to 100° C. and maintained at 100° C. with stirring for a period of 0.5 hours. The resulting product is then cooled to 60° C. and admixed with ml water. The resulting product now exists in two phases: an organic phase and an aqueous phase. The organic phase is separated from the aqueous phase and the organic phase is washed, consecutively, with an equal volume of saturated aqueous sodium chloride followed by saturated aqueous sodium bicarbonate. The resulting product is dried over anhydrous magnesium sulfate and fractionally distilled yielding the following fractions:

| Fraction Number | Vapor Temperature (°C.) | Liquid Temperature (°C.) | Vacuum mm/Hg Pressure | Reflux Ratio |
|---|---|---|---|---|
| 1 | 90 | 127 | 0.5 | 4:1 |
| 2 | 80 | 128 | 0.5 | 4:1 |
| 3 | 103 | 130 | 1.0 | 4:1 |
| 4 | 102 | 124 | 1.0 | 4:1 |
| 5 | 102 | 128 | .990 | 4:1 |
| 6 | 102 | 127 | 1.0 | 4:1 |
| 7 | 102 | 128 | .966 | 4:1 |
| 8 | 101 | 128 | .978 | 4:1 |
| 9 | 101 | 131 | .954 | 4:1 |
| 10 | 101 | 128 | .960 | 4:1 |
| 11 | 102 | 128 | .984 | 4:1 |
| 12 | 95 | 127 | .66 | 1:1 |
| 13 | 96 | 131 | .7 | 1:1 |
| 14 | 99 | 127 | .79 | 1:1 |
| 15 | 95 | 127 | .67 | 1:1 |
| 16 | 96 | 132 | .68 | 1:1 |
| 17 | 96 | 132 | .625 | 1:1 |
| 18 | 95 | 139 | .67 | 1:1 |
| 19 | 96 | 179 | .685 | 1:1 |

Example III(B)

Reaction:

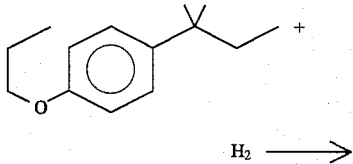

$H_2$ ⟶

49
-continued

Reaction:

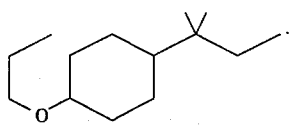

Into a 500 cc autoclave equipped with a hydrogen feed line are placed the following materials:

(i) compound having the structure:

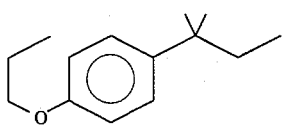

prepared according to Example III(A), bulked distillation fractions 3–18, 296 grams;

(ii) 3% ruthenium on aluminum oxide catalyst, 6.0 grams; and (iii) isopropyl alcohol, 38 grams.

The autoclave is sealed and pressurized with hydrogen to 25 psig and heated to 115°–120° C. The hydrogen feed is continued for a period of 2 hours while maintaining the temperature at 115°–20° C. and the pressure at 600 psig.

At the end of the 2 hour period, the autoclave is cooled and opened and the reaction product is filtered.

The resulting filtrate is fractionallly distilled yielding the following fractions:

| Fraction Number | Vapor Temperature (°C.) | Liquid Temperature (°C.) | Vacuum mm/Hg Pressure | Reflux Ratio |
|---|---|---|---|---|
| 1 | 23/29 | 23/100 | 150/30 | 100% |
| 2 | 112 | 118 | 2 | 4:1 |
| 3 | 112 | 117 | 1 | 4:1 |
| 4 | 112 | 117 | 1 | 4:1 |
| 5 | 112 | 118 | 1.2 | 4:1 |
| 6 | 113 | 119 | 1.2 | 4:1 |
| 7 | 113 | 120 | 1.2 | 4:1 |
| 8 | 116 | 121 | 1.5 | 4:1 |
| 9 | 116 | 121 | 1.5 | 4:1 |
| 10 | 118 | 123 | 1.5 | 4:1 |
| 11 | 123 | 132 | 1.8 | 4:1 |
| 12 | 120 | 185 | <1 | 4:1 |

Fraction 8 has a cis:trans isomer ratio of 47:53 with the cis isomer having the structure:

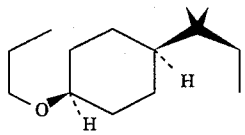

and the trans isomer having the structure:

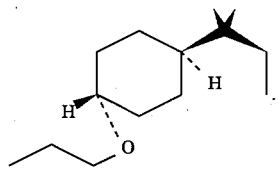

50
EXAMPLE IV

PREPARATION OF t-BUTYL PROPOXYCYCLOHEXANE

Example IV(A)

Reactions:

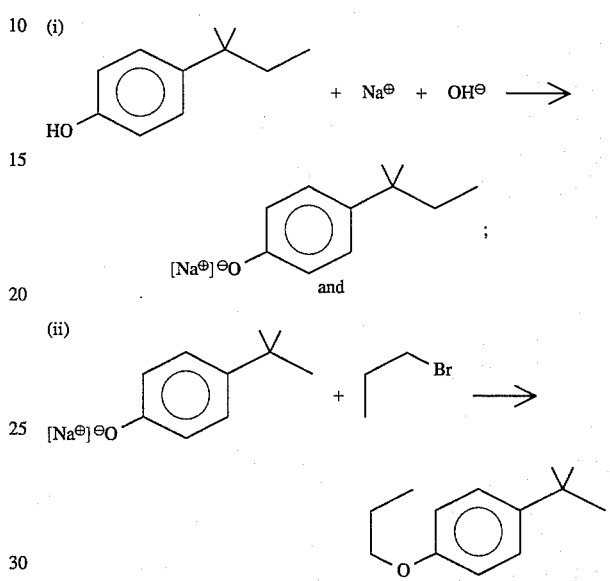

Into a 2 liter reaction vessel equipped with stirrer, thermometer, reflux condenser and heating mantle are placed the following ingredients:

sodium hydroxide, 141 grams;

water, 423 grams; and

ALIQUAT® 336, 18 grams.

The resulting mixture is heated to 75° C.

Over a period of 1 hour, 352 grams of t-butylphenol having the structure:

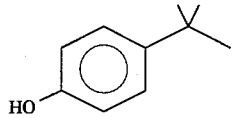

is added to the reaction mass with stirring while maintaining the temperature at 75° C.

Over a period of 2 hours while maintaining the reaction mass at a temperature of 69° C. n-propyl bromide is added to the reaction mass. The reaction mass is maintained at 69° C. with stirring for an additional 10 hours.

At the end of the 10 hour period, 500 grams of 25% aqueous sodium hydroxide is added to the reaction mass and the reaction mass is heated for a period of 1 hour.

At the end of the 1 hour period, the reaction mass is cooled to room temperature and the reaction mass now exists in two phases: an organic phase and an aqueous phase. The organic phase is admixed with 50 ml of toluene. The organic phase is then dried over anhydrous magnesium sulfate. The resulting product is then admixed with 40 grams of propionic anhydride and the resulting mixture is heated to 100° C. and maintained at 100° C. with stirring for a period of 0.5 hours. The resulting product is then cooled to 60° C. and admixed with 100 ml water. The resulting product now exists in two phases: an organic phase and an aqueous phase. The organic phase is separated from the aqueous phase and the organic phase is washed, consecutively, with an equal volume of saturated aqueous sodium chloride followed by saturated aqueous sodium bicarbonate. The resulting product is dried over anhydrous magnesium sulfate and fractionally distilled yielding the following fractions:

| Fraction Number | Vapor Temperature (°C.) | Liquid Temperature (°C.) | Vacuum mm/Hg Pressure | Reflux Ratio |
| --- | --- | --- | --- | --- |
| 1 | 100 | 111 | 0.3/1.34 | 1:1/4:1 |
| 2 | 97 | 113 | 1.32 | 4:1 |
| 3 | 97 | 111 | 1.29 | 4:1 |
| 4 | 97 | 113 | 1.29 | 4:1 |
| 5 | 98 | 111 | 1.33 | 4:1 |
| 6 | 97 | 110 | 1.28 | 4:1 |
| 7 | 97 | 110 | 1.30 | 4:1 |
| 8 | 97 | 110 | 1.30 | 4:1 |
| 9 | 97 | 110 | 1.31 | 4:1 |
| 10 | 98 | 110 | 1.39 | 4:1 |
| 11 | 98 | 110 | 1.38 | 4:1 |
| 12 | 97 | 110 | 1.27 | 4:1 |
| 13 | 97 | 110 | 1.27 | 4:1 |
| 14 | 97 | 110 | 1.27 | 4:1 |
| 15 | 96 | 110 | 1.29 | 1:1 |
| 16 | 46 | 118 | 1.26 | 1:1 |

The resulting product (bulked distillation fractions 6–15) has the structure:

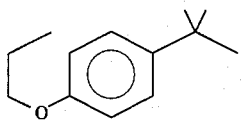

as confirmed by NMR, IR and mass spectral analyses.

Example IV(B)

Reaction:

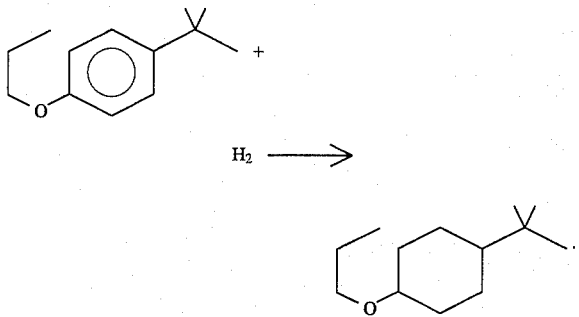

Into a 1 liter autoclave equipped with hydrogen feed line are placed the following materials:

(i) bulked distillation fractions 6–15 of the distillation of the reaction product of Example IV(A), the compound having the structure:

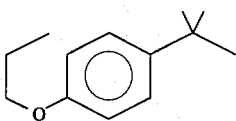

(ii) 3% ruthenium on silicone oxide catalyst, 6.3 grams; and (iii) n-propanol, 100 grams.

The autoclave is sealed and pressurized with hydrogen to 60 psig at a temperature of 160°–165° C. The hydrogen pressurization at 600 psig is continued for a period of 14 hours while maintaining the autoclave temperature at 160°–165° C.

At the end of the 14 hour period, the autoclave is cooled and opened and the reaction mass is filtered and distilled. The distillate contains:

(i) 90% of the compound having the structure:

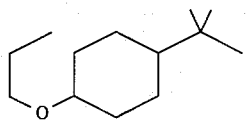

(ii) 3% of the starting material having the structure:

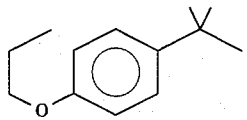

and (iii) 6% of the alcohol having the structure:

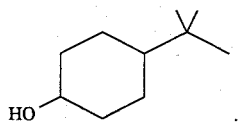

The filtrate is fractionally distilled yielding the following fractions:

| Fraction Number | Vapor Temperature (0° C.) | Liquid Temperature (0° C.) | Vacuum mm/Hg Pressure | Reflux Ratio |
| --- | --- | --- | --- | --- |
| 1 | 23 | 23 | 120 | 100% |
| 2 | 78 | 96 | 1.0 | 9:1 |
| 3 | 94 | 98 | 2.5 | 9:1 |
| 4 | 98 | 104 | 4.0 | 9:1 |
| 5 | 96 | 105 | 3.5 | 9:1 |
| 6 | 97 | 104 | 3.5 | 9:1 |
| 7 | 98 | 106 | 3.0 | 9:1 |
| 8 | 99 | 106 | 3.0 | 9:1 |
| 9 | 101 | 112 | 3.0 | 9:1 |
| 10 | 102 | 120 | 2.0 | 9:1 |
| 11 | 96 | 190 | <1 | 1:1 |

Fraction 8 has a cis:trans isomer ration of 6:1 with the cis isomer having the structure:

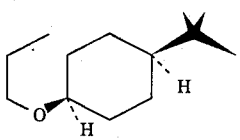

53 and the trans isomer having the structure:

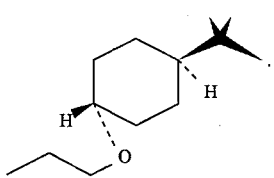

EXAMPLE V

PREPARATION OF 2-METHYL-4-t-AMYLHEXAHYDROANISOLE

Example V(A)

Reaction:

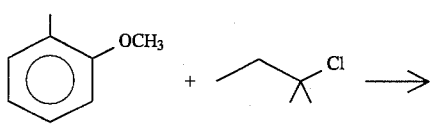

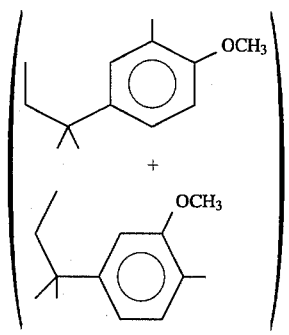

Into a 5 liter reaction vessel equipped with stirrer, thermometer, reflux condenser and cooling coils are placed the following materials:

methylene chloride, 1 liter; and
aluminum chloride anhydrous, 536 grams.

The resulting mixture is cooled to 0° C. and over a period of 0.5 hours, 600 grams of 2-methyl anisole is added to the reaction mass. The 2-methyl anisole has the structure:

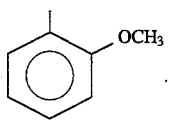

While maintaining the reaction mass at 0°–5° C., over a period of 2 hours, t-amyl chloride is added to the reaction mass with stirring causing evolution of hydrogen chloride gas.

At the end of the 2 hour feeding period for the t-amyl chloride, the reaction mass is quenched onto ice and then washed with an equal volume of 20% aqueous sodium hydroxide. The reaction mass is then fractionally distilled to yield the mixture of meta and para isomers having the structures:

54

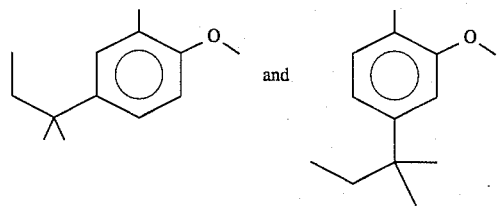

with the meta isomer having the structure:

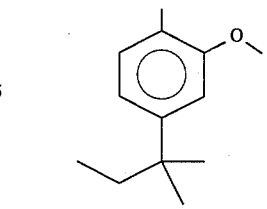

and the para isomer having the structure:

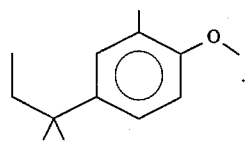

The ratio of the para:meta isomers is 87:13.

Example V(B)

Reaction:

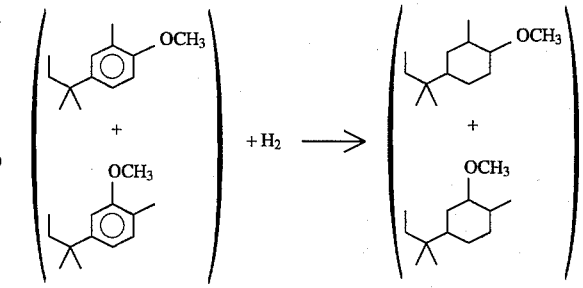

Into a 1 liter autoclave equipped with hydrogen feed line are placed the following materials:

(i) 2-methyl-4-t-amyl anisole mixture of isomers having the structures:

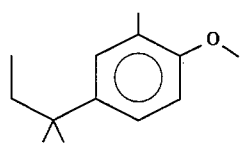

and

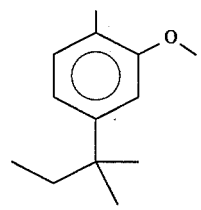

prepared according to Example V(A), 500 grams;

(ii) 3% ruthenium on aluminum oxide catalyst, 10.0 grams; and (iii) isopropyl alcohol, 35 grams.

The autoclave is sealed and pressurized to 600 psig with hydrogen at a temperature of 115°–20° C. Over a period of 4 hours, hydrogen pressurization at 600 psig is continued while maintaining the autoclave temperature at 115°–120° C.

At the end of the 3 hour period, the autoclave is cooled and opened and the contents of the autoclave are filtered. The resulting filtrate contains a mixture of isomers of the compounds having the structures:

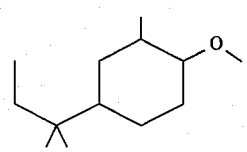

and

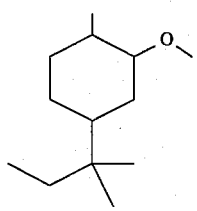

including the isomer having the structure:

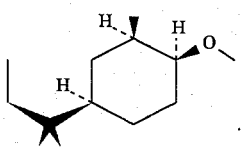

The ratio of para:meta isomers is 87:13 with the para isomer having the structure:

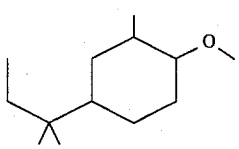

and the meta isomer having the structure:

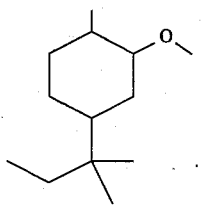

The fractional distillation yields the following fractions:

| Fraction Number | Vapor Temperature (0° C.) | Liquid Temperature (0° C.) | Vacuum mm/Hg Pressure | Reflux Ratio |
| --- | --- | --- | --- | --- |
| 1 | 23/33 | 23/105 | 150/40 | 100% |
| 2 | 96 | 103 | 2.8 | 4:1 |
| 3 | 101 | 107 | 3.0 | 4:1 |
| 4 | 101 | 107 | 3.0 | 4:1 |
| 5 | 101 | 107 | 3.0 | 4:1 |
| 6 | 102 | 107 | 3.0 | 4:1 |
| 7 | 100 | 105 | 2.5 | 4:1 |
| 8 | 101 | 104 | 2.5 | 4:1 |
| 9 | 104 | 102 | 2.5 | 4:1 |
| 10 | 103 | 107 | 2.5 | 4:1 |
| 11 | 105 | 108 | 2.5 | 4:1 |
| 12 | 103 | 108 | 2.5 | 4:1 |
| 13 | 104 | 108 | 2.5 | 4:1 |
| 14 | 106 | 110 | 2.5 | 4:1 |
| 15 | 104 | 110 | 2.5 | 4:1 |
| 16 | 104 | 112 | 2.5 | 4:1 |
| 17 | 81 | 150 | 2.0 | 4:1 |

EXAMPLE VI

PREPARATION OF 2-METHYL-4-t-AMYLHEXAHYDROPHENETOLE

Example VI(A)

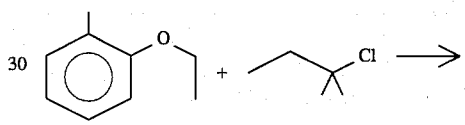

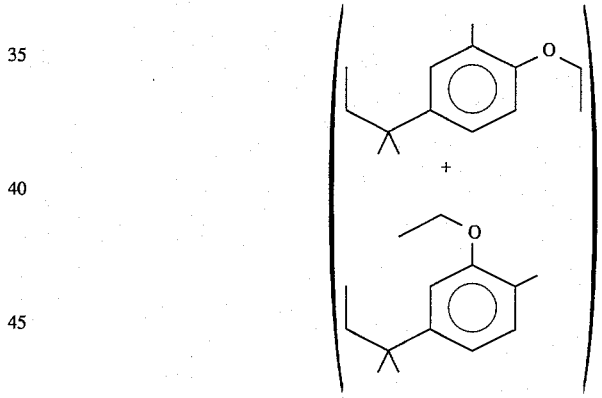

Into a 5 liter reaction vessel equipped with stirrer, thermometer, reflux condenser and cooling coils are placed the following materials:

methylene chloride, 1 liter; and aluminum chloride (anhydrous), 268 grams.

The resulting mixture is cooled to 0° C.

Over a period of 0.5 hours, 2-methyl-phenetole having the structure:

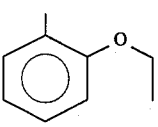

is added to the reaction mass.

Over a period of 2 hours while maintaining the reaction mass at 0°–5° C. t-amyl chloride is added to the reaction mass causing evolution of hydrogen chloride gas.

At the end of the 2 hour t-amyl chloride feeding period, the reaction mass is aged for 0.5 hours and then quenched onto ice. The organic phase is separated from the aqueous phase and the organic phase is then washed with an equal volume of 20% aqueous sodium hydroxide. The organic phase is then separated from the aqueous phase and the organic phase is dried over anhydrous magnesium sulfate and then fractionally distilled yielding the following fractions:

| Fraction Number | Vapor Temperature (°C.) | Liquid Temperature (°C.) | Vacuum mm/Hg Pressure | Reflux Ratio |
| --- | --- | --- | --- | --- |
| 1 | 23/115 | 23/125 | 150/6 | 4:1 |
| 2 | 125 | 127 | 4.0 | 4:1 |
| 3 | 125 | 127 | 4.0 | 4:1 |
| 4 | 126 | 128 | 3.0 | 4:1 |
| 5 | 125 | 126 | 3.0 | 1:1 |
| 6 | 124 | 126 | 3.0 | 1:1 |
| 7 | 126 | 128 | 3.2 | 1:1 |
| 8 | 125 | 127 | 3.0 | 1:1 |
| 9 | 124 | 128 | 3.0 | 1:1 |
| 10 | 126 | 131 | 3.5 | 1:1 |
| 11 | 123 | 133 | 2.5 | 1:1 |
| 12 | 120 | 135 | 1.0 | 1:1 |
| 13 | 102 | 165 | <1 | 100% |

Example VI(B)

Reaction:

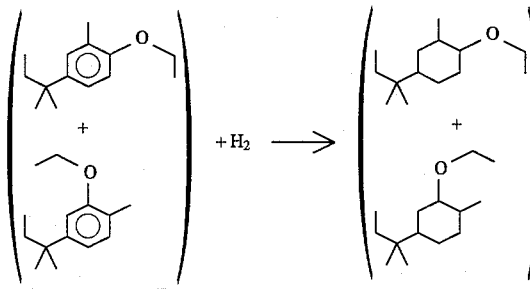

Into a 1 liter autoclave equipped with hydrogen feed line are placed the following materials:

(i) mixture of para and meta isomers having the structures:

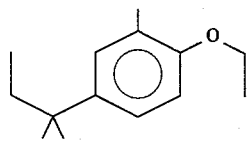

and

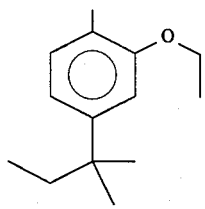

prepared according to Example VI(A), bulked distillation fractions 2–11 (ratio of para:meta isomer equal 92:8), 355 grams;

(ii) 3% ruthenium on aluminum oxide catalyst, 7.1 grams; and (iii) isopropyl alcohol, 36 grams.

The para isomer has the structure:

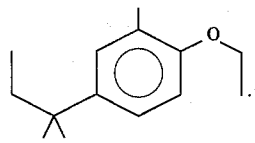

The meta isomer has the structure:

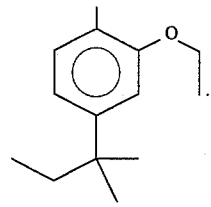

The autoclave is sealed and pressurized with hydrogen to a pressure of 600 psig at a temperature of 115°–120° C.

Over a period of 4.25 hours, the autoclave is continued to be pressurized with hydrogen at 600 psig and at a temperature of 115°–120° C.

At the end of the 4.25 hour period, the autoclave is cooled and then opened and the contents are filtered. The resulting filtrate is fractionally distilled yielding the following fractions:

| Fraction Number | Vapor Temperature (°C.) | Liquid Temperature (°C.) | Vacuum mm/Hg Pressure | Reflux Ratio |
| --- | --- | --- | --- | --- |
| 1 | 23/33 | 23/105 | 150/30 | 100% |
| 2 | 94 | 105 | 1.5 | 4:1 |
| 3 | 103 | 110 | 4.0 | 4:1 |
| 4 | 102 | 109 | 3.0 | 4:1 |
| 5 | 97 | 107 | 1.5 | 4:1 |
| 6 | 96 | 107 | 1.5 | 4:1 |
| 7 | 98 | 106 | 1.5 | 4:1 |
| 8 | 98 | 106 | 1.5 | 4:1 |
| 9 | 101 | 107 | 2.2 | 4:1 |
| 10 | 102 | 108 | 2.5 | 4:1 |
| 11 | 98 | 107 | 1.5 | 4.1 |
| 12 | 102 | 108 | 2.0 | 4:1 |
| 13 | 103 | 108 | 2.0 | 4:1 |
| 14 | 104 | 110 | 2.0 | 4:1 |
| 15 | 101 | 109 | 1.5 | 4:1 |
| 16 | 104 | 114 | 2.0 | 4:1 |
| 17 | 104 | 114 | 2.0 | 4:1 |
| 18 | 103 | 116 | 1.5 | 4:1 |
| 19 | 69 | 160 | 1.0 | 4:1 |

The resulting product contains a mixture of meta and para isomers having the structures:

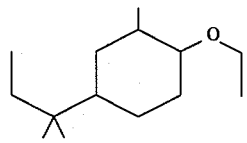

and

The para isomer has the structure:

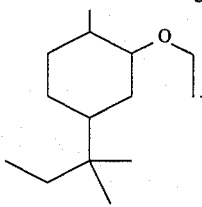

and the meta isomer has the structure:

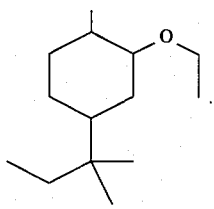

These isomers include a number of cis and trans isomers including that having the structure:

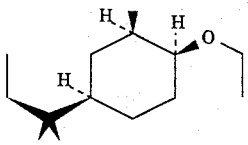

(the cis-cis-cis isomer). The ratio of the para:meta isomers is 92:8.

EXAMPLE VII

PREPARATION OF 2-t-AMYL HEXAHYDROPHENETOLE

Example VII(A)

Reactions:

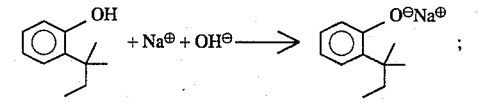 (i)

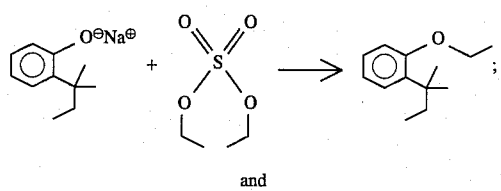 (ii)

and summary reaction:

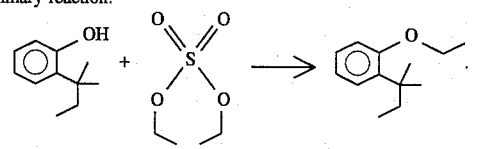 (iii)

Into a 1 liter reaction vessel equipped with stirrer, thermometer, reflux condenser and heating mantle are placed the following ingredients:

sodium hydroxide, 90.2 grams;
water, 270 grams; and
ALIQUAT® 336, 15 grams.

The resulting mixture is heated to 55° C.

Over a period of 1 hour, 300 grams of the compound having the structure:

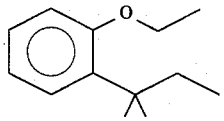

is added to the reaction mass with stirring while maintaining the temperature at 55° C.

Over a period of 40 minutes while maintaining the reaction temperature of 55°–65° C., diethyl sulfate having the structure:

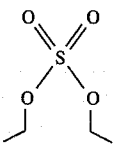

is added to the reaction mass. The reaction mass is maintained at 55°–65° C. with stirring for a period of 3.67 hours. At the end of the 3.67 hour period, a solution of 90 grams of sodium hydroxide in 270 grams of water is admixed with the reaction mass. The reaction mass is then refluxed at 103° C. for a period of 2 hours. The reaction mass now exists in two phases: an organic phase and an aqueous phase. The organic phase is washed with 2 equal volumes of water consecutively. The organic phase is then separated from the aqueous phase and dried over anhydrous magnesium sulfate. The resulting product is then fractionally distilled yielding the following fractions:

| Fraction Number | Vapor Temperature (°C.) | Liquid Temperature (°C.) | Vacuum mm/Hg Pressure | Reflux Ratio |
|---|---|---|---|---|
| 1 | 71 | 86 | 0.9 | 9:1 |
| 2 | 68 | 88 | 0.71 | 9:1 |
| 3 | 73 | 89 | 1.03 | 9:1 |
| 4 | 70 | 88 | 0.95 | 9:1 |
| 5 | 69 | 88 | 0.6 | 1:1 |
| 6 | 70 | 89 | 0.66 | 1:1 |
| 7 | 70 | 90 | 0.68 | 1:1 |
| 8 | 69 | 90 | 0.67 | 1:1 |
| 9 | 69 | 95 | 0.64 | 1:1 |
| 10 | 70 | 120 | 0.65 | 1:1 |
| 11 | 77 | 175 | 0.70 | 1:1 |

Distillation fractions 4–10 are bulked. Bulked distillation fractions 4–10 consists of the compound having the structure:

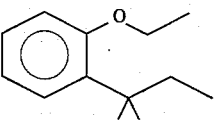

(as confirmed by NMR, IR and mass spectral analyses).

Example VII(B)

Reaction:

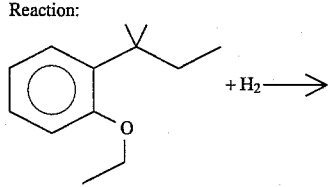  +H$_2$ →

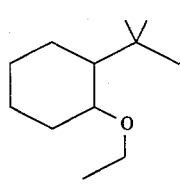

Into a 500 cc autoclave equipped with hydrogen feed line are placed the following materials:

(i) the compound having the structure:

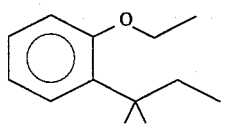

prepared according to Example VII(A), 100 grams;

(ii) 3% ruthenium on aluminum oxide catalyst, 3.1 grams; and (iii) isopropyl alcohol, 19 grams.

The autoclave is sealed and pressurized with hydrogen to a pressure of 600 psig at a temperature of 115°–120° C. The pressurization with hydrogen at 600 psig is continued for a period of 1 hour while maintaining the reaction mass temperature at 115°–120° C.

At the end of the 1 hour period, the autoclave is cooled and opened and the contents are filtered. The resulting product is fractionally distilled yielding the following fractions:

| Fraction Number | Vapor Temperature (°C.) | Liquid Temperature (°C.) | Vacuum mm/Hg Pressure | Reflux Ratio |
|---|---|---|---|---|
| 1 | 23/35 | 23/105 | 150/85 | 100% |
| 2 | 84 | 91 | 2 | 9:1 |
| 3 | 85 | 91 | 2 | 9:1 |
| 4 | 84 | 90 | 2 | 9:1 |
| 5 | 84 | 90 | 2 | 9:1 |
| 6 | 85 | 91 | 2 | 9:1 |
| 7 | 87 | 94 | 2 | 3:1 |
| 8 | 88 | 95 | 3 | 3:1 |
| 9 | 89 | 96 | 2 | 3:1 |
| 10 | 88 | 95 | 2 | 3:1 |
| 11 | 85 | 95 | 1.5 | 3:1 |
| 12 | 85 | 94 | 1.2 | 3:1 |
| 13 | 83 | 110 | 1.5 | 3:1 |
| 14 | 79 | 140 | 1 | 3:1 |

The resulting product has a cis:trans isomer ratio of 90:1 with the cis isomer having the structure:

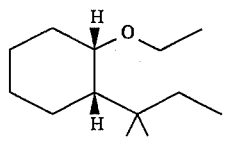

and the trans isomer having the structure:

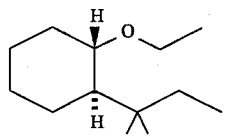

Example VIII

PERFUME FORMULATIONS

The following woody cologne perfume formulations are prepared:

| Ingredients | Parts by Weight | | | |
|---|---|---|---|---|
| | VIII(A) | VIII(B) | VIII(C) | VIII(D) |
| Bergamot oil | 150 | 150 | 150 | 150 |
| Orange oil | 200 | 200 | 200 | 200 |
| Lemon oil | 50 | 50 | 50 | 50 |
| Eugenol | 10 | 10 | 10 | 10 |
| 4-(4-methyl-4-hydroxy amyl-$\Delta^3$-cyclohexene) carboxaldehyde (LYRAL ® Trademark of International Flavors & Fragrances Inc. of New York, New York) | 40 | 40 | 40 | 40 |
| Ylang oil | 2 | 2 | 2 | 2 |
| Petitgrain Paraguay | 10 | 10 | 10 | 10 |
| γ-Methyl ionone | 20 | 20 | 20 | 20 |
| Vetiver Venezuela | 18 | 18 | 18 | 18 |
| 3-α-Methyl-dodecahydro-6,6,9a-trimethylnaptho[2,1-b]furan | 5 | 5 | 5 | 5 |
| Product produced by the reaction of acetic anhydride, polyphosphoric acid and 1,5,9-trimethyl cyclododecatriene-1,5,9 according to the process of Example I of U.S. Letters Pat. No. 3,718,697, the specification for which is incorporated by reference herein. | 50 | 50 | 50 | 50 |
| Octahydro-9,9-dimethyl-1,6- | 50 | 50 | 50 | 50 |

-continued

| Ingredients | Parts by Weight | | | |
|---|---|---|---|---|
| | VIII(A) | VIII(B) | VIII(C) | VIII(D) |
| methanonaphthalene-1-[2H]-ol produced according to Example III of U.S. Letters Pat. No. 3,996,169, the specification for which is incorporated by reference herein. | | | | |
| The compound having the structure: 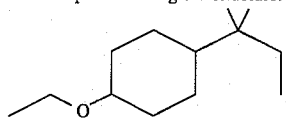 produced according to Example I(B), bulked distillation fractions Nos. 6–14 (50:50 cis:trans isomer mixture). | 12 | 0 | 0 | 0 |
| The compound having the structure: 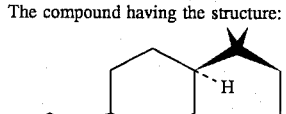 (high amount of cis isomer) prepared according to Example II(A) (iv), distillation fraction No. 9. | 0 | 12 | 0 | 0 |
| The compound having the structure: 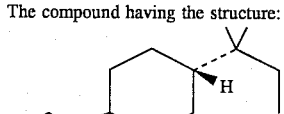 (high amount of trans isomer) prepared according to Example II(A) (iv), distillation fraction No. 25. | 0 | 0 | 12 | 0 |
| The 2:1 cis:trans isomer mixture of the isomers having the structures:  and 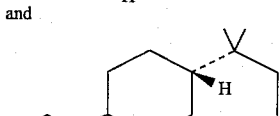 prepared according to Example II(B), bulked distillation fractions Nos. 7–12. | 0 | 0 | 0 | 12 |

The compound having the structure:

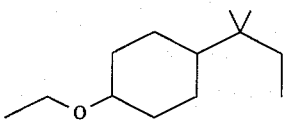

imparts to this woody cologne formulation green (fresh cut grass-like), woody, floral (muguet), balsamic, linden blossom, cucumber and melon-like undertones with green, ozoney, woody and floral (muguet) topnotes. Accordingly, the perfume composition of Example VIII(A) can be described as having:

a woody cologne aroma with green (fresh cut grass-like), woody, floral (muguet), balsamic, linden blossom, cucumber and melon-like undertones with green, ozoney, woody and floral (muguet) topnotes.

The isomer having the structure:

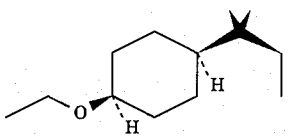

imparts to this woody cologne formulation green, floral and ozoney undertones with green, floral and ozoney topnotes.

Accordingly, the perfume composition of Example VIII(B) can be described as having:

a woody cologne aroma with green, floral and ozoney undertones and green, floral and ozoney topnotes.

The isomer having the structure:

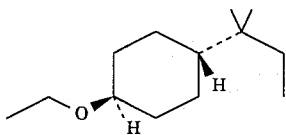

imparts to this woody cologne formulation floral undertones with floral, green and ozoney topnotes. Accordingly, the perfume composition of Example VIII(C) can be described as having:

a woody cologne aroma with floral undertones and floral, green and ozoney topnotes.

The 2:1 cis:trans isomer mixture of compounds having the structures:

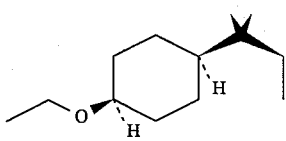

and

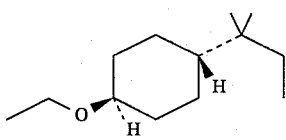

prepared according to Example II(B), distillation fractions 7–12 imparts to this woody cologne formulation waxy, citrusy, orange peel-like, fresh floral and ozoney undertones. Accordingly, the perfume composition of Example VIII(D) can be described as having:

a woody cologne aroma with waxy, citrusy, orange peel-like, fresh floral and ozoney undertones.

Example IX

PERFUME FORMULATIONS

The following woody cologne perfume formulations are prepared:

| Ingredients | Parts by Weight | | | |
| --- | --- | --- | --- | --- |
|  | IX(A) | IX(B) | IX(C) | IX(D) |
| Bergamot oil | 150 | 150 | 150 | 150 |
| Orange oil | 200 | 200 | 200 | 200 |
| Lemon oil | 50 | 50 | 50 | 50 |
| Eugenol | 10 | 10 | 10 | 10 |
| 4-(4-methyl-4-hydroxy amyl-$\Delta^3$-cyclohexene) carboxaldehyde (LYRAL ® Trademark of International Flavors & Fragrances Inc. of New York, New York) | 40 | 40 | 40 | 40 |
| Ylang oil | 2 | 2 | 2 | 2 |
| Petitgrain Paraguay | 10 | 10 | 10 | 10 |
| γ-Methyl ionone | 20 | 20 | 20 | 20 |
| Vetiver Venezuela | 18 | 18 | 18 | 18 |
| 3-α-Methyl-dodecahydro-6,6,9a-trimethylnaptho[2,1-b]furan | 5 | 5 | 5 | 5 |
| Product produced by the reaction of acetic anhydride, polyphosphoric acid and 1,5,9-trimethyl cyclododecatriene-1,5,9 according to the process of Example I of U.S. Letters Patent No. 3,718,697, the specification for which is incorporated by reference herein. | 50 | 50 | 50 | 50 |
| Octahydro-9,9-dimethyl-1,6-methanonaphthalene-1-[2H]-ol produced according to Example III of U.S. Letters Patent No. 3,996,169, the specification for which is incorporated by reference herein. | 50 | 50 | 50 | 50 |
| The compound having the structure: [structure] produced according to Example III(B), distillation fraction 8. | 12 | 0 | 0 | 0 |
| The compound having the structure: [structure] prepared according to Example IV(A). | 0 | 12 | 0 | 0 |
| The compound having the structure: [structure] prepared according to Example IV(B), distillation fraction 8. | 0 | 0 | 12 | 0 |
| The mixture of the isomers having the structures: [structures] | 0 | 0 | 0 | 12 |

67
-continued

| Ingredients | Parts by Weight | | | |
|---|---|---|---|---|
| | IX(A) | IX(B) | IX(C) | IX(D) |
| prepared according to Example V(A). | — | | | |

The compound having the structure:

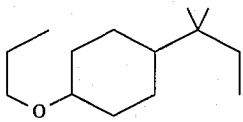

prepared according to Example III(B) imparts to this woody cologne formulation ozoney, green, privet hedge (*Ligustrum vulgare*)-like, floral and fatty undertones. Accordingly, the perfume composition of Example IX(A) can be described as having:

a woody cologne aroma with ozoney, green, privet hedge (*Ligustrum vulgare*)-like, floral and fatty undertones.

The compound having the structure:

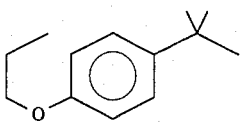

imparts to this woody cologne formulation balsamic, cigar box-like and mahogany undertones with mint topnotes. Accordingly, the perfume composition of Example IX(B) can be described as having:

a woody cologne aroma with balsamic, cigar box-like and mahogany undertones with mint topnotes.

The compound having the structure:

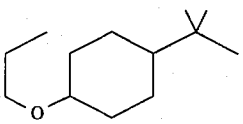

prepared according to Example IV(B), distillation fraction 8 imparts to this woody cologne formulation green, woody, sweet and anise undertones with minty, camphoraceous, piney and patchouli topnotes. Accordingly, the perfume composition of Example IX(C) can be described as having:

a woody cologne aroma with green, woody, sweet and anise undertones with minty, camphoraceous, piney and patchouli topnotes.

The the mixture of para and meta isomers having the structures:

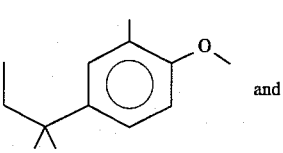 and 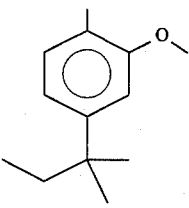

prepared according to Example V(A) imparts to this woody cologne formulation green, leafy, rosy and twiggy undertones with fresh green, rosy and celery leaf-like topnotes.

68

Accordingly, the perfume composition of Example IX(D) can be described as having:

a woody cologne aroma with green, leafy, rosy and twiggy undertones with fresh green, rosy and celery leaf-like topnotes.

Example X

PERFUME FORMULATIONS

The following woody cologne perfume formulations are prepared:

| Ingredients | Parts by Weight | | | |
|---|---|---|---|---|
| | X(A) | X(B) | X(C) | X(D) |
| Bergamot oil | 150 | 150 | 150 | 150 |
| Orange oil | 200 | 200 | 200 | 200 |
| Lemon oil | 50 | 50 | 50 | 50 |
| Eugenol | 10 | 10 | 10 | 10 |
| 4-(4-methyl-4-hydroxy amyl-$\Delta^3$-cyclohexene) carboxaldehyde (LYRAL ® Trademark of International Flavors & Fragrances Inc. of New York, New York) | 40 | 40 | 40 | 40 |
| Ylang oil | 2 | 2 | 2 | 2 |
| Petitgrain Paraguay | 10 | 10 | 10 | 10 |
| γ-Methyl ionone | 20 | 20 | 20 | 20 |
| Vetiver Venezuela | 18 | 18 | 18 | 18 |
| 3-α-Methyl-dodecahydro-6,6,9a-trimethylnaptho[2,1-b]furan | 5 | 5 | 5 | 5 |
| Product produced by the reaction of acetic anhydride, polyphosphoric acid and 1,5,9-trimethyl cyclododecatriene-1,5,9 according to the process of Example I of U.S. Letters Pat. No. 3,718,697, the specification for which is incorporated by reference herein. | 50 | 50 | 50 | 50 |
| Octahydro-9,9-dimethyl-1,6-methanonaphthalene-1-[2H]-ol produced according to Example III of U.S. Letters Pat. No. 3,996,169, the specification for which is incorporated by reference herein. | 50 | 50 | 50 | 50 |
| The mixture of compounds having the structures: | 12 | 0 | 0 | 0 | prepared according to Example V(B).

| | | | | |
|---|---|---|---|---|
| The mixture of compounds having the structures: | 0 | 12 | 0 | 0 |

69
-continued

| Ingredients | Parts by Weight | | | |
|---|---|---|---|---|
| | X(A) | X(B) | X(C) | X(D) |
| 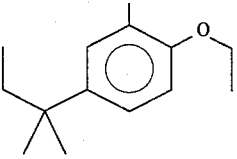 and 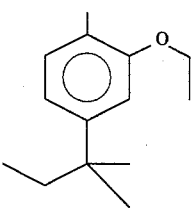 prepared according to Example VI(A), distillation fraction 8. | | | | |
| The mixture of compounds having the structures: | 0 | 0 | 12 | 0 |
| 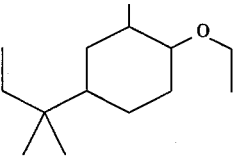 and 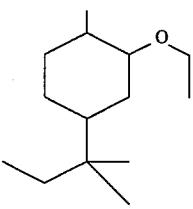 prepared according to Example VI(B), distillation fraction 11. | | | | |
| The mixture of compounds having the structures: | 0 | 0 | 0 | 12 |
| 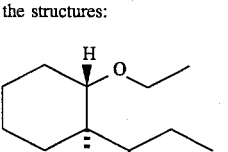 and 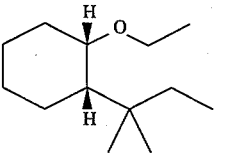 prepared according to Example VII(B), distillation fraction 9. | | | | |

70

The mixtures of compounds having the structures:

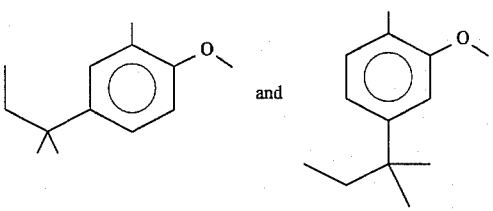

prepared according to Example V(B) imparts to this woody cologne formulation green, ozoney, fatty, woody, floral and amber undertones with green, fatty and ozoney topnotes. Accordingly, the perfume composition of Example X(A) can be described as having:

a woody cologne aroma with green, ozoney, fatty, woody, floral and amber undertones with green, fatty and ozoney topnotes.

The mixtures of compounds having the structures:

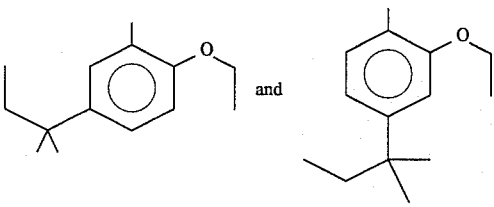

prepared according to Example VI(A), distillation fraction 8 imparts to this woody cologne formulation cedarwood, cigar box-like and fruity undertones. Accordingly, the perfume composition of Example X(B) can be described as having:

a woody cologne aroma with cedarwood, cigar box-like and fruity undertones.

The mixture of compounds having the structures:

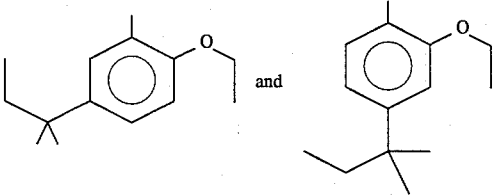

prepared according to Example VI(B), distillation fraction 11 imparts to this woody cologne formulation waxy, fatty, aldehydic, muguet, privet hedge (*Ligustrum vulgare*)-like, dewy and rose undertones with fatty, aldehydic and floral topnotes. Accordingly, the perfume composition of Example X(C) can be described as having:

a woody cologne aroma with waxy, fatty, aldehydic, muguet, privet hedge (*Ligustrum vulgare*)-like, dewy and rose undertones with fatty, aldehydic and floral topnotes.

The the mixture of compounds having the structures:

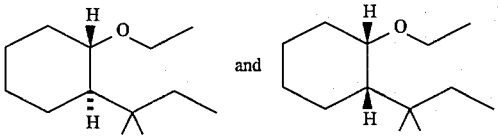

prepared according to Example VII(B), distillation fraction 9 imparts to this woody cologne formulation earthy undertones and green topnotes. Accordingly, the perfume composition of Example X(D) can be described as having:

a woody cologne aroma with earthy undertones and green topnotes.

Example XI

PREPARATION OF COSMETIC POWDER COMPOSITIONS

Cosmetic powder compositions are prepared by mixing in a ball mill 100 grams of talcum powder with 0.25 grams of each of the substances set forth in Table II below. Each of the cosmetic powder compositions has an excellent aroma as described in Table II below:

TABLE II

| Substance | Aroma Description |
|---|---|
| The compound having the structure: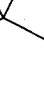prepared according to Example I(B), distillation fractions 6–14 (50:50 cis:trans isomers). | A green (fresh cut grass-like), woody, floral (muguet), balsamic aroma with green, ozoney, woody, floral (muguet) topnotes and linden blossom, cucumber and melon-like undertones. |
| The compound having the structure:prepared according to Example II(A)(iv), distillation fraction 9. | A powerful green, floral and ozoney aroma with green, floral and ozoney topnotes. |
| The compound having the structure: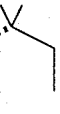prepared according to Example II(A)(iv), distillation fraction 25. | A floral aroma with floral, green and ozoney topnotes. |
| The 2:1 cis:trans isomer mixture having the structures:and | A waxy, citrusy, orange peel-like and fresh floral aroma with ozoney undertones. |

TABLE II-continued

| Substance | Aroma Description |
|---|---|
| prepared according to Example II(B), distillation fractions 7–12. | |
| The compound having the structure: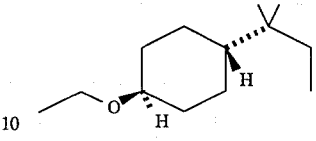prepared according to Example III(B), distillation fraction 8. | An ozoney, green, privet hedge (*Ligustrum vulgare*)-like, floral and fatty aroma with fatty, ozoney and green undertones. |
| The compound having the structure: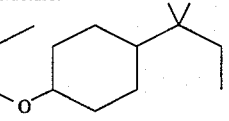prepared according to Example IV(A). | A balsamic, cigar box-like and mahogany aroma with mint topnotes. |
| The structure having the structure: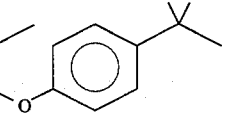prepared according to Example IV(B), distillation fraction 8. | A green, woody and sweet aroma with anise undertones and minty, camphoraceous, piney and patchouli topnotes. |
| The mixture of para and meta isomers having the structures: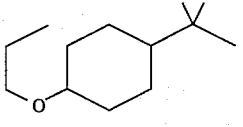and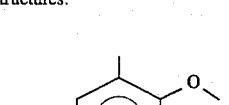prepared according to | A green, leafy, rosy and twiggy aroma with fresh green, rosy and celery leaf-like topnotes. |

TABLE II-continued

| Substance | Aroma Description |
|---|---|
| Example V(A). | |
| The mixture of compounds having the structures: 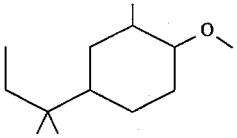 and 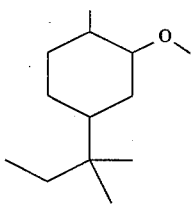 prepared according to Example V(B). | A green, ozoney, fatty, woody, floral and amber aroma with green, fatty and ozoney topnotes. |
| The mixture of compounds having the structures: 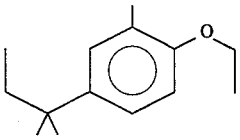 and 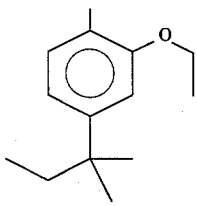 prepared according to Example VI(A), distillation fraction 8. | A cedarwood and cigar box-like aroma with fruity undertones. |
| The mixture of compounds having the structures: 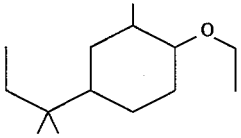 and 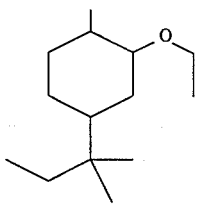 prepared according to | A fatty, waxy, aldehydic, muguet, privet hedge (*Ligustrum vulgare*)-like, dewy and rose aroma with fatty, aldehydic and floral topnotes. |

TABLE II-continued

| Substance | Aroma Description |
|---|---|
| Example VI(B), distillation fraction 11. | |
| The mixture of compounds having the structures: 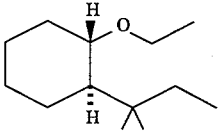 and 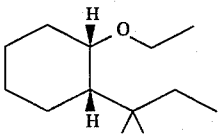 prepared according Example III(B), distillation fraction 9. | An earthy aroma with green topnotes. |
| The perfume composition of Example VIII(A). | A woody cologne aroma with green (fresh cut grass-like), woody, floral (muguet), balsamic, linden blossom, cucumber and melon-like undertones with green, ozoney, woody and floral (muguet) topnotes. |
| The perfume composition of Example VIII(B). | A woody cologne aroma with green, floral and ozoney undertones and green, floral and ozoney topnotes. |
| The perfume composition of VIII(C). | A woody cologne aroma with floral undertones and floral, green and ozoney topnotes. |
| The perfume composition of Example VIII(D). | A woody cologne aroma with waxy, citrusy, orange peel-like, fresh floral and ozoney undertones. |
| The perfume composition of Example IX(A). | A woody cologne aroma with ozoney, green, privet hedge (*Ligustrum vulgare*)-like, floral and fatty undertones. |
| The perfume composition of Example IX(B). | A woody cologne aroma with balsamic, cigar box-like and mahogany undertones with mint topnotes. |
| The perfume composition of Example IX(C). | A woody cologne aroma with green, woody, sweet and anise undertones with minty, camphoraceous, piney and patchouli topnotes. |
| The perfume composition of Example IX(D). | A woody cologne aroma with green, leafy, rosy and twiggy undertones with fresh green, rosy and celery leaf-like topnotes. |
| The perfume composition of Example X(A). | A woody cologne aroma with green, ozoney, fatty, woody, floral and amber undertones with green, fatty and ozoney topnotes. |
| The perfume composition of Example X(B). | A woody cologne aroma with cedarwood, cigar box-like and fruity undertones. |
| The perfume composition of Example X(C). | A woody cologne aroma with waxy, fatty, aldehydic, muguet, privet hedge (*Ligustrum vulgare*)-like, dewy and rose undertones with fatty, aldehydic and floral |

TABLE II-continued

| Substance | Aroma Description |
| --- | --- |
| The perfume composition of Example X(D). | topnotes. A woody cologne aroma with earthy undertones and green topnotes. |

Example XII

PERFUMED LIQUID DETERGENTS

Concentrated liquid detergents (lysine salt of n-dodecylbenzene sulfonic acid as more specifically described in U.S. Pat. No. 3,948,818 issued Apr. 6, 1976 and incorporated by reference herein) with aroma nuances as set forth in Table II of Example XI are prepared containing 0.10%, 0.15%, 0.20%, 0.30% and 0.35% of the substance set forth in Table II of Example XI. They are prepared by adding and homogeneously mixing the appropriate quantity of substance set forth in Table II of Example XI in the liquid detergent. The detergents all possess excellent aromas as set forth in Table II of Example XI, the intensity increasing with greater concentrations of substances as set forth in Table II of Example XI

Example XIII

PREPARATIONS OF COLOGNES AND HANDKERCHIEF PERFUMES

Compositions as set forth in Table II of Example XI are incorporated into colognes at concentrations of 2.0%, 2.5%, 3.0%, 3.5%, 4.0%, 4.5% and 5.0% in 80%, 85%, 90% and 95% aqueous food grade ethanol solutions; and into handkerchief perfumes at concentrations of 15%, 20%, 25% and 30% (in 80%, 85%, 90% and 95% aqueous food grade ethanol solutions). Distinctive and definitive fragrances as set forth in Table II of Example XI are imparted to the colognes and to the handkerchief perfumes at all levels indicated.

Example XIV

PREPARATION OF SOAP COMPOSITIONS

100 Grams of soap chips [per sample] (IVORY®, produced by the Procter & Gamble Company of Cincinnati, Ohio) are each mixed with 1 gram samples of substances as set forth in Table II of Example XI until homogeneous aroma compositions are obtained. In each of the cases, the homogeneous compositions are heated under 8 atmospheres pressure at 180° C. for a period of 3 hours and the resulting liquids are placed into soap molds. The resulting soap cakes, on cooling, manifest aromas as set forth in Table II of Example XI.

Example XV

PREPARATION OF SOLID DETERGENT COMPOSITIONS

Detergents are prepared using the following ingredients according to Example I of Canadian Patent No. 1,007,948 (incorporated by reference herein):

| Ingredient | Percent by Weight |
| --- | --- |
| NEODOL ® 45-11 (a $C_{12}$–$C_{15}$ alcohol ethoxylated with 11 moles of ethylene oxide | 12 |
| Sodium carbonate | 55 |
| Sodium citrate | 20 |
| Sodium sulfate, water brighteners | q.s. |

This detergent is a phosphate-free detergent. Samples of 100 grams each of this detergent are admixed with 0.10, 0.15, 0.20 and 0.25 grams of each of the substances as set forth in Table II of Example XI. Each of the detergent samples has an excellent aroma as indicated in Table II of Example XI.

Example XVI

Utilizing the procedure of Example I at column 15 of U.S. Pat. No. 3,632,396 (the disclosure of which is incorporated herein by reference), non-woven cloth substrates useful as drier-added fabric softening articles of manufacture are prepared wherein the substrate, the substrate coating, the outer coating and their perfuming material are as follows:

1. A water "dissolvable" paper ("Dissolvo Paper");
2. Adogen 448 (m.p. about 140° F.) as the substrate coating; and
3. An outer coating having the following formulation (m.p. about 150° F.):
   57% $C_{20-22}$ HAPS;
   22% isopropyl alcohol;
   20% antistatic agent; and
   1% of one of the substances as set forth in Table II of Example XI.

Fabric softening compositions prepared according to Example I at column 15 of U.S. Pat. No. 3,632,396 having the aroma characteristics as set forth in Table II of Example XI, supra, consist of a substrate coating having a weight of about 3 grams per 100 square inches of substrate; a first coating located directly on the substrate coating consisting of about 1.85 grams per 100 square inches of substrate; and an outer coating coated on the first coating consisting of about 1.4 grams per 100 square inches of substrate. One of the substances of Table II of Example XI is admixed in each case with the outer coating mixture, thereby providing a total aromatized outer coating weight ratio to substrate of about 0.5:1 by weight of the substrate. The aroma characteristics are imparted in a pleasant manner to the head space in a dryer on operation thereof in each case using said drier-added fabric softener non-woven fabrics and these aroma characteristics are described in Table II of Example XI, supra.

Example XVII

HAIR SPRAY FORMULATIONS

The following hair spray formulation is prepared by first dissolving PVP/VA E-735 copolymer manufactured by the GAF Corporation of 140 West 51st Street, New York, N.Y. in 91.62 grams of 95% of food grade ethanol. 8.0 Grams of the polymer is dissolved in the alcohol. The following ingredients are added to the PVP/VA alcoholic solution:

| Ingredient | Percent by Weight |
| --- | --- |
| Dioctyl sebacate | 0.05 |
| Benzyl alcohol | 0.10 |
| Dow corning 473 fluid (prepared by the Dow Corning Corporation) | 0.10 |
| TWEEN ® 20 surfactant (prepared by ICI America Corporation) | 0.03 |
| One of the perfumery substances as set forth in Table II of Example XI, supra | 0.10 |

The perfuming substances as set forth in Table II of Example XI add aroma characteristics as set forth in Table II of Example XI which are rather intense and aesthetically pleasing to the users of the soft-feel, good-hold pump hair sprays.

Example XVIII

CONDITIONING SHAMPOOS

Monamid CMA (prepared by the Mona Industries Company) (3.0 weight percent) is melted with 2.0 weight percent coconut fatty acid (prepared by the Procter & Gamble Company of Cincinnati, Ohio; 1.0 weight percent ethylene glycol distearate (prepared by the Armak Corporation) and triethanolamine (a product of the Union Carbide Corporation) (35.0 weight percent). The resulting mixture is heated to 60° C. and mixed until a clear solution is obtained (at 60° C.). This material is "COMPOSITION A".

GAFQUAT® 755N polymer (manufactured by the GAF Corporation of 140 West 51st Street, New York, N.Y.) (5.0 weight percent) is admixed with 0.1 weight percent sodium sulfite and 1.4 weight percent polyethylene glycol 6000 distearate produced by the Armak Corporation. This material is "COMPOSITION B".

The resulting "COMPOSITION A" and "COMPOSITION B" are than mixed in a 50:50 weight ratio of A:B and cooled to 45° C. and 0.3 weight percent of perfuming substance as set forth in Table II of Example V is added to the mixture. The resulting mixture is cooled to 40° C. and blending is carried out for an additional one hour in each case. At the end of this blending period, the resulting material has a pleasant fragrance as indicated in Table II of Example XI.

What is claimed is:

1. An alkyl-substituted-$C_1$–$C_3$ alkoxy-$C_6$-cycloaliphatic compound defined according to the structure:

$$R_3'{-}O{-}Z'{-}\underset{R_2'}{\overset{}{C}}{-}R_1'$$

wherein Z' represents meta or para cyclohexylene or meta or para phenylene and wherein $R_1'$ and $R_2'$ are each the same or different hydrogen or methyl; and wherein $R_3'$ represents $C_1C_3$ alkyl; and wherein the moiety:

$(R_3'{-}O{-})$ is ortho with respect to $R_2$ and para or meta with respect to the moiety:

$({-}\underset{}{\overset{}{C}}{-}R_1')$ with the proviso that the sum of the number of carbon atoms in $R_1+R_2+R_3$ is 4.

2. An alkyl-substituted-$C_1$–$C_3$ alkoxy-$C_6$-cycloaliphatic compound of claim 1 being an isomer having the structure:

3. An alkyl-substituted-$C_1$–$C_3$ alkoxy-$C_6$-cycloaliphatic compound of claim 1 being an isomer having the structure:

4. An alkyl-substituted-$C_1$–$C_3$ alkoxy-$C_6$-cycloaliphatic compound of claim 1 which is a mixture of cis and trans isomers having the structures:

in substantially equal proportion.

5. An alkyl-substituted-$C_1$–$C_3$ alkoxy-$C_6$-cycloaliphatic compound of claim 1 having the structure:

6. An alkyl-substituted-$C_1$–$C_3$ alkoxy-$C_6$-cycloaliphatic compound of claim 1 which is a mixture of cis and trans isomers having the structures:

7. An alkyl-substituted-$C_1$–$C_3$ alkoxy-$C_6$-cycloaliPhatic compound of claim 1 which is a mixture of compounds having the structures:

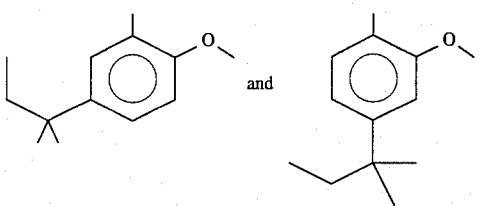

8. An alkyl-substituted-$C_1$-$C_3$ alkoxy-$C_6$-cycloaliphatic compound of claim 1 which is a mixture of isomers having the structures:

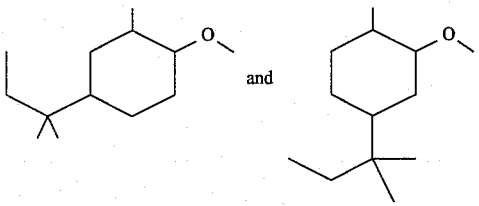

9. An alkyl-substituted-$C_1$-$C_3$ alkoxy-$C_6$-cycloaliphatic compound of claim 1 which is a mixture of isomers having the structures:

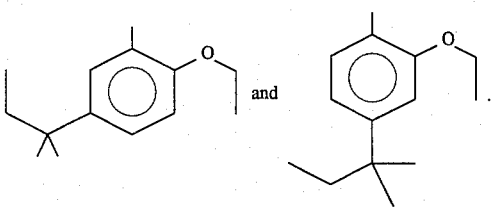

10. An alkyl-substituted-$C_1$-$C_3$ alkoxy-$C_6$-cycloaliphatic compound of claim 1 having the structure:

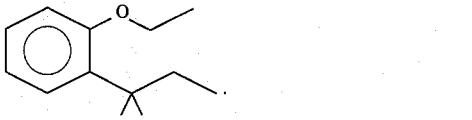

11. An alkyl-substituted-$C_1$-$C_3$ alkoxy-$C_6$-cycloaliphatic compound of claim 1 which is a mixture of isomers having the structures:

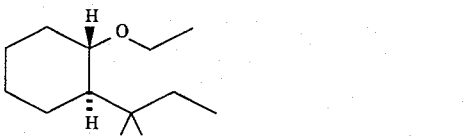

and

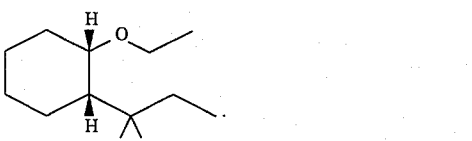

12. A process for augmenting, enhancing or imparting an aroma to a consumable material selected from the group consisting of perfume compositions, perfumed articles and colognes comprising the step of intimately admixing with said consumable material an aroma imparting, augmenting or enhancing quantity of at least one compound defined according the structure:

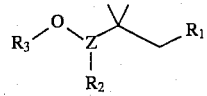

wherein Z represents meta or para cyclohexylene or meta or para phenylene and wherein $R_1$ and $R_2$ are the same or different hydrogen or methyl; and wherein $R_3$ represents $C_1C_3$ alkyl; and wherein the moiety:

is ortho with respect to $R_2$ and para or meta with respect to the moiety:

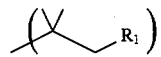

with the proviso that the sum of the number of carbon atoms in $R_1+R_2+R_3$ is 3 or 4.

13. The process of claim 12 wherein the consumable material is a perfume composition.

14. The process of claim 12 wherein the consumable material is a perfumed article.

15. The process of claim 12 wherein the consumable material is a perfumed polymer.

16. The process of claim 12 wherein the consumable material is a cologne.

17. The process of claim 12 wherein the compound admixed with the perfumed article has the structure:

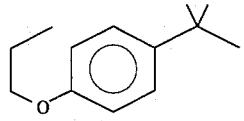

18. The process of claims 12 wherein the compound admixed with the perfumed article is a mixture of cis and trans isomers having the structures:

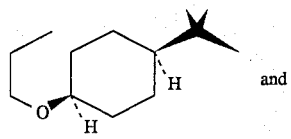

and

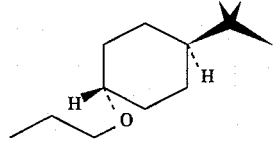

* * * * *